United States Patent
Yamada et al.

(10) Patent No.: US 11,324,219 B2
(45) Date of Patent: May 10, 2022

(54) AMIDE COMPOUND OR SALT THEREOF, AGRICULTURAL AND HORTICULTURAL MICROBICIDE COMPRISING THE COMPOUND AND THE SALT, AND METHOD FOR USING THE AGRICULTURAL AND HORTICULTURAL MICROBICIDE

(71) Applicant: Nihon Nohyaku Co., Ltd., Tokyo (JP)

(72) Inventors: Keiichi Yamada, Osaka (JP); Yutaka Abe, Osaka (JP); Yutaka Kato, Osaka (JP); Ayuko Nakauchi, Osaka (JP); Yuki Saito, Osaka (JP); Shunsuke Fuchi, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 16/976,436

(22) PCT Filed: Mar. 1, 2019

(86) PCT No.: PCT/JP2019/007970
§ 371 (c)(1),
(2) Date: Aug. 27, 2020

(87) PCT Pub. No.: WO2019/168140
PCT Pub. Date: Sep. 6, 2019

(65) Prior Publication Data
US 2021/0000111 A1    Jan. 7, 2021

(30) Foreign Application Priority Data

Mar. 2, 2018 (JP) .............................. JP2018-037047
Aug. 6, 2018 (JP) .............................. JP2018-147495

(51) Int. Cl.
| | | |
|---|---|---|
| C07D 207/34 | (2006.01) | |
| A01N 43/10 | (2006.01) | |
| A01N 43/08 | (2006.01) | |
| A01N 43/36 | (2006.01) | |
| A01N 43/40 | (2006.01) | |
| C07D 307/66 | (2006.01) | |
| C07D 307/68 | (2006.01) | |
| C07D 333/36 | (2006.01) | |
| C07D 409/04 | (2006.01) | |

(52) U.S. Cl.
CPC ............. *A01N 43/10* (2013.01); *A01N 43/08* (2013.01); *A01N 43/36* (2013.01); *A01N 43/40* (2013.01); *C07D 207/34* (2013.01); *C07D 307/66* (2013.01); *C07D 307/68* (2013.01); *C07D 333/36* (2013.01); *C07D 409/04* (2013.01)

(58) Field of Classification Search
None
See application file for complete search history.

(56) References Cited

U.S. PATENT DOCUMENTS

| | | |
|---|---|---|
| 6,699,818 B1 | 3/2004 | Walter et al. |
| 2004/0171490 A1 | 9/2004 | Walter et al. |
| 2006/0172891 A1 | 8/2006 | Gewehr et al. |
| 2008/0064874 A1 | 3/2008 | Dunkel et al. |
| 2015/0307462 A1 | 10/2015 | Koehn et al. |
| 2016/0366884 A1 | 12/2016 | Yonemura et al. |
| 2017/0332635 A1 | 11/2017 | Yonemura et al. |

FOREIGN PATENT DOCUMENTS

| | | | |
|---|---|---|---|
| EP | 3296291 A1 | 3/2018 | |
| JP | 2003-519212 A | 6/2003 | |
| JP | 2006-521316 A | 9/2006 | |
| JP | 2007-520504 A | 7/2007 | |
| JP | 2016-506385 A | 3/2016 | |
| WO | WO 2007/125749 A1 | 11/2007 | |
| WO | WO 2007/128410 A1 | 11/2007 | |
| WO | WO 2015/072463 A1 | 5/2015 | |
| WO | WO 2015/117912 | * 8/2015 | ........... C07D 207/00 |
| WO | WO 2015/117912 A1 | 8/2015 | |
| WO | WO 2015/144652 A2 | 10/2015 | |

OTHER PUBLICATIONS

CAS RN 1094658-52-2 (entered in STN on Jan. 21, 2009) (Year: 2009).*
CAS RN 1838941-62-0 (entered into STN on Dec. 30, 2015) (Year: 2015).*
STN International, "2-Thiophenecarboxylicacid, 3-[[[2, 4-dimethyl-6-(methylthio)-5-pyrimidinyl]carbonyl]amino]-" Jan. 21, 2009, CAS Registry No. 1094658-52-2.
International Search Report for PCT/JP2019/007970 dated May 7, 2019.

(Continued)

*Primary Examiner* — Craig D Ricci
(74) *Attorney, Agent, or Firm* — Knobbe Martens Olson & Bear LLP

(57) ABSTRACT

An amide compound represented by the general formula [I]:

[Chem. 1]

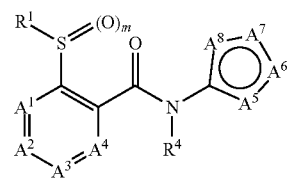

[I]

or a salt thereof, an agricultural and horticultural microbicide comprising the compound or the salt as an active ingredient, and a method for using the agricultural and horticultural microbicide.

10 Claims, No Drawings

(56) References Cited

OTHER PUBLICATIONS

International Preliminary Report on Patentability for PCT/JP2019/007970 dated Sep. 8, 2020.
Supplementary European Search Report for EP 19761174 dated Jul. 14, 2021.

* cited by examiner

AMIDE COMPOUND OR SALT THEREOF, AGRICULTURAL AND HORTICULTURAL MICROBICIDE COMPRISING THE COMPOUND AND THE SALT, AND METHOD FOR USING THE AGRICULTURAL AND HORTICULTURAL MICROBICIDE

CROSS REFERENCE TO RELATED APPLICATIONS

This application is a U.S. National Phase Application of PCT International Application Number PCT/JP2019/007970, filed on Mar. 1, 2019, designating the United States of America and published in the Japanese language, which is an International Application of and claims the benefit of priority to Japanese Patent Application No. 2018-037047, filed on Mar. 2, 2018, and Japanese Patent Application No. 2018-147495, filed on Aug. 6, 2018. The disclosures of the above-referenced applications are hereby expressly incorporated by reference in their entireties.

TECHNICAL FIELD

The present invention relates to an amide compound or a salt thereof, an agricultural and horticultural microbicide comprising the compound or the salt as an active ingredient, and a method for using the agricultural and horticultural microbicide.

BACKGROUND ART

Various compounds have been examined for their potential as agricultural and horticultural microbicides, and among them, certain kinds of amide compounds have been reported to be useful insecticides and microbicides (for example, see Patent Literature 1).

The literature, however, does not disclose the amide compound of the present invention.

CITATION LIST

Patent Literature

Patent Literature 1: WO 2015/072463

SUMMARY OF INVENTION

Technical Problem

In crop production in the fields of agriculture, horticulture and the like, the damage caused by various diseases etc. is still immense, and diseases resistant to existing microbicides have emerged. Under such circumstances, the development of novel agricultural and horticultural microbicides is desired. In addition, laborsaving and automated application is a recent trend in these fields, and from this viewpoint, there is a need for the development of microbicides having properties suitable for various application methods, such as seed treatment, small-volume application, and topical application. That is, there is a need for microbicides having moderate environmental and thermal stability and adequate translocation and diffusibility throughout crop plants or the vicinity thereof. Meanwhile, in the context of a growing demand for sustainable agriculture, agrochemical toxicity and impact on surrounding living organisms and surrounding environment are assessed from various viewpoints, and there is a need for microbicides having safety from various aspects, moderate persistence, biodegradability, environmental degradability, etc.

Solution to Problem

The present inventors conducted extensive research to solve the above-described problems. As a result, the present inventors found that an amide compound represented by the general formula [I] or a salt thereof is highly effective for controlling agricultural and horticultural diseases. The present inventors conducted further research and thus found that the amide compound or a salt thereof is suitable for use in various agrochemical applications and excellent in physicochemical and biochemical properties. Based on these findings, the present invention has been completed.

That is, the present invention relates to the following.

[1] An amide compound represented by the following formula [I]

[Chem. 1]

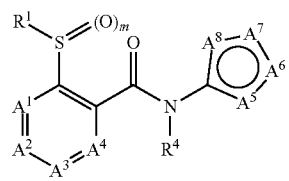

[I]

{wherein
R$^1$ represents (a1) a (C$_1$-C$_6$) alkyl group,
m represents an integer of 0, 1, or 2,
A$^1$, A$^3$, and A$^4$ may be the same or different and each represent a nitrogen atom or C—R$^2$,
R$^2$ represents
(b1) a hydrogen atom;
(b2) a halogen atom;
(b3) a (C$_1$-C$_6$) alkyl group;
(b4) a (C$_3$-C$_6$) cycloalkyl group; or
(b5) a halo (C$_1$-C$_6$) alkyl group,
A$^2$ represents C—R$^3$,
R$^3$ represents
(c1) a halogen atom;
(c2) a (C$_1$-C$_6$) alkyl group;
(c3) a (C$_3$-C$_6$) cycloalkyl group;
(c4) a halo (C$_1$-C$_6$) alkyl group;
(c5) a (C$_1$-C$_6$) alkoxy group;
(c6) a halo (C$_1$-C$_6$) alkoxy group;
(c7) a (C$_1$-C$_6$) alkylthio group;
(c8) a halo (C$_1$-C$_6$) alkylthio group;
(c9) a cyano (C$_1$-C$_6$) alkyl group;
(c10) a cyano (C$_3$-C$_6$) cycloalkyl group;
(c11) a (C$_3$-C$_6$) cycloalkyl (C$_1$-C$_6$) alkyl group;
(c12) a (C$_1$-C$_6$) alkoxy (C$_1$-C$_6$) alkyl group;
(c13) a (C$_1$-C$_6$) alkoxycarbonyl (C$_1$-C$_6$) alkyl group;
(c14) a (C$_1$-C$_6$) alkylcarbonyl group;
(c15) a halo (C$_1$-C$_6$) alkylcarbonyl group;
(c16) a (C$_3$-C$_6$) cycloalkylcarbonyl group;
(c17) a (C$_1$-C$_6$) alkoxycarbonyl group;
(c18) a (C$_1$-C$_6$) alkylthio (C$_1$-C$_6$) alkyl group;
(c19) a (C$_1$-C$_6$) alkylsulfinyl (C$_1$-C$_6$) alkyl group;
(c20) a (C$_1$-C$_6$) alkylsulfonyl (C$_1$-C$_6$) alkyl group;
(c21) a (C$_2$-C$_6$) alkenyl group;
(c22) a (C$_2$-C$_6$) alkynyl group;

(c23) a ($C_1$-$C_6$) alkylsulfinyl group;
(c24) a halo ($C_1$-$C_6$) alkylsulfinyl group;
(c25) a ($C_1$-$C_6$) alkylsulfonyl group;
(c26) a halo ($C_1$-$C_6$) alkylsulfonyl group;
(c27) an R'(R") aminocarbonyl group wherein R' and R" may be the same or different and each represent one group selected from a hydrogen atom, a ($C_1$-$C_6$) alkyl group, and a halo ($C_1$-$C_6$) alkyl group;
(c28) an R" carbonyl (R') amino group wherein R' and R" are as defined above; or
(c29) a group represented by the structural formula (R')C=N—OR" wherein R' and R" are as defined above,
$R^4$ represents
(d1) a hydrogen atom;
(d2) a ($C_1$-$C_6$) alkyl group;
(d3) a halo ($C_1$-$C_6$) alkyl group;
(d4) a cyano ($C_1$-$C_6$) alkyl group;
(d5) a ($C_3$-$C_6$) cycloalkyl group;
(d6) a ($C_3$-$C_6$) cycloalkyl ($C_1$-$C_6$) alkyl group;
(d7) a ($C_1$-$C_6$) alkoxy ($C_1$-$C_6$) alkyl group;
(d8) a ($C_1$-$C_6$) alkoxycarbonyl ($C_1$-$C_6$) alkyl group;
(d9) a ($C_1$-$C_6$) alkylcarbonyl group;
(d10) a halo ($C_1$-$C_6$) alkylcarbonyl group;
(d11) a ($C_3$-$C_6$) cycloalkylcarbonyl group;
(d12) a ($C_1$-$C_6$) alkoxycarbonyl group;
(d13) a ($C_1$-$C_6$) alkylthio ($C_1$-$C_6$) alkyl group;
(d14) a ($C_1$-$C_6$) alkylsulfinyl ($C_1$-$C_6$) alkyl group;
(d15) a ($C_1$-$C_6$) alkylsulfonyl ($C_1$-$C_6$) alkyl group;
(d16) a tri-($C_1$-$C_3$) alkylsilyl ($C_1$-$C_6$) alkyl group;
(d17) a ($C_2$-$C_6$) alkenyl group;
(d18) a ($C_2$-$C_6$) alkynyl group;
(d19) a ($C_1$-$C_6$) alkylsulfonyl group; or
(d20) a halo ($C_1$-$C_6$) alkylsulfonyl group,
$A^5$ represents an oxygen atom, a sulfur atom, N—$R^5$, or a C—$R^5$ group,
$A^6$ represents an oxygen atom, a sulfur atom, N—$R^6$, or a C—$R^6$ group,
with the proviso that, when either $A^5$ or $A^6$ represents an oxygen atom, a sulfur atom, N—$R^5$, or C—$R^6$, the other does not represent an oxygen atom, a sulfur atom, N—$R^5$ or C—$R^6$ at the same time, or $A^5$ and $A^6$ do not represent the same substituent,
$A^7$ represents a C—$R^7$ group,
$A^8$ represents a C—$R^8$ group,
$R^5$ represents
(e1) a hydrogen atom;
(e2) a halogen atom;
(e3) a ($C_1$-$C_6$) alkyl group;
(e4) a halo ($C_1$-$C_6$) alkyl group;
(e5) a ($C_1$-$C_6$) alkoxy group;
(e6) a halo ($C_1$-$C_6$) alkoxy group;
(e7) a ($C_1$-$C_6$) alkylthio group;
(e8) a halo ($C_1$-$C_6$) alkylthio group;
(e9) a cyano ($C_1$-$C_6$) alkyl group;
(e10) a ($C_3$-$C_6$) cycloalkyl group;
(e11) a ($C_3$-$C_6$) cycloalkyl ($C_1$-$C_6$) alkyl group;
(e12) a ($C_1$-$C_6$) alkoxy ($C_1$-$C_6$) alkyl group;
(e13) a ($C_1$-$C_6$) alkoxycarbonyl ($C_1$-$C_6$) alkyl group;
(e14) a ($C_1$-$C_6$) alkylcarbonyl group;
(e15) a halo ($C_1$-$C_6$) alkylcarbonyl group;
(e16) a ($C_3$-$C_6$) cycloalkylcarbonyl group;
(e17) a carboxyl group;
(e18) a ($C_1$-$C_6$) alkoxycarbonyl group;
(e19) a benzyloxycarbonyl group;
(e20) a substituted benzyloxycarbonyl group having, on the ring, 1 to 5 substituents selected from a halogen atom, a nitro group, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_2$-$C_6$) alkenyl group, a halo ($C_2$-$C_6$) alkenyl group, a ($C_2$-$C_6$) alkynyl group, a ($C_3$-$C_6$) cycloalkyl group, a ($C_2$-$C_6$) alkenyloxy group, a halo ($C_2$-$C_6$) alkenyloxy group, a ($C_1$-$C_6$) alkylthio group, a halo ($C_1$-$C_6$) alkylthio group, a ($C_1$-$C_6$) alkylsulfonyloxy group, a halo ($C_1$-$C_6$) alkylsulfonyloxy group, a ($C_1$-$C_6$) alkylsulfinyl group, a halo ($C_1$-$C_6$) alkylsulfinyl group, a ($C_1$-$C_6$) alkylsulfonyl group, a halo ($C_1$-$C_6$) alkylsulfonyl group, a ($C_2$-$C_6$) alkenylthio group, a halo ($C_2$-$C_6$) alkenylthio group, a ($C_2$-$C_6$) alkenylsulfinyl group, a halo ($C_2$-$C_6$) alkenylsulfinyl group, a ($C_2$-$C_6$) alkenylsulfonyl group, a halo ($C_2$-$C_6$) alkenylsulfonyl group, a mono-($C_1$-$C_6$) alkylamino group, a di-($C_1$-$C_6$) alkylamino group (wherein the alkyl groups may be the same or different), a ($C_1$-$C_6$) alkylsulfonylamino group, a halo ($C_1$-$C_6$) alkylsulfonylamino group, a ($C_1$-$C_6$) alkylcarbonyl group, a halo ($C_1$-$C_6$) alkylcarbonyl group, a ($C_1$-$C_6$) alkyloxycarbonyl group, and a phenyl group, wherein, when the number of the substituents is more than one, these substituents may be the same or different;
(e21) a ($C_1$-$C_6$) alkylthio ($C_1$-$C_6$) alkyl group;
(e22) a ($C_1$-$C_6$) alkylsulfinyl ($C_1$-$C_6$) alkyl group;
(e23) a ($C_1$-$C_6$) alkylsulfonyl ($C_1$-$C_6$) alkyl group;
(e24) a ($C_2$-$C_6$) alkenyl group;
(e25) a ($C_2$-$C_6$) alkynyl group;
(e26) a ($C_1$-$C_6$) alkylsulfinyl group;
(e27) a halo ($C_1$-$C_6$) alkylsulfinyl group;
(e28) a ($C_1$-$C_6$) alkylsulfonyl group;
(e29) a halo ($C_1$-$C_6$) alkylsulfonyl group;
(e30) a phenyl group;
(e31) a substituted phenyl group having, on the ring, 1 to 5 substituents selected from a halogen atom, a nitro group, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_2$-$C_6$) alkenyl group, a halo ($C_2$-$C_6$) alkenyl group, a ($C_2$-$C_6$) alkynyl group, a ($C_3$-$C_6$) cycloalkyl group, a ($C_2$-$C_6$) alkenyloxy group, a halo ($C_2$-$C_6$) alkenyloxy group, a ($C_1$-$C_6$) alkylthio group, a halo ($C_1$-$C_6$) alkylthio group, a ($C_1$-$C_6$) alkylsulfonyloxy group, a halo ($C_1$-$C_6$) alkylsulfonyloxy group, a ($C_1$-$C_6$) alkylsulfinyl group, a halo ($C_1$-$C_6$) alkylsulfinyl group, a ($C_1$-$C_6$) alkylsulfonyl group, a halo ($C_1$-$C_6$) alkylsulfonyl group, a ($C_2$-$C_6$) alkenylthio group, a halo ($C_2$-$C_6$) alkenylthio group, a ($C_2$-$C_6$) alkenylsulfinyl group, a halo ($C_2$-$C_6$) alkenylsulfinyl group, a ($C_2$-$C_6$) alkenylsulfonyl group, a halo ($C_2$-$C_6$) alkenylsulfonyl group, a mono-($C_1$-$C_6$) alkylamino group, a di-($C_1$-$C_6$) alkylamino group (wherein the alkyl groups may be the same or different), a ($C_1$-$C_6$) alkylsulfonylamino group, a halo ($C_1$-$C_6$) alkylsulfonylamino group, a ($C_1$-$C_6$) alkylcarbonyl group, a halo ($C_1$-$C_6$) alkylcarbonyl group, a ($C_1$-$C_6$) alkyloxycarbonyl group, and a phenyl group, wherein, when the number of the substituents is more than one, these substituents may be the same or different;
(e32) a heterocyclic group; or
(e33) a heterocyclic group having, on the ring, 1 to 3 substituents selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group, and a halo ($C_1$-$C_6$) alkylsulfonyl group,
wherein, when the number of the substituents is more than one, these substituents may be the same or different,
$R^6$ represents
(f1) a hydrogen atom;
(f2) a halogen atom;

(f3) a ($C_1$-$C_6$) alkyl group;
(f4) a halo ($C_1$-$C_6$) alkyl group;
(f5) a ($C_1$-$C_6$) alkoxy group;
(f6) a halo ($C_1$-$C_6$) alkoxy group;
(f7) a ($C_1$-$C_6$) alkylthio group;
(f8) a halo ($C_1$-$C_6$) alkylthio group;
(f9) a cyano ($C_1$-$C_6$) alkyl group;
(f10) a ($C_3$-$C_6$) cycloalkyl group;
(f11) a ($C_3$-$C_6$) cycloalkyl ($C_1$-$C_6$) alkyl group;
(f12) a ($C_1$-$C_6$) alkoxy ($C_1$-$C_6$) alkyl group;
(f13) a ($C_1$-$C_6$) alkoxycarbonyl ($C_1$-$C_6$) alkyl group;
(f14) a ($C_1$-$C_6$) alkylcarbonyl group;
(f15) a halo ($C_1$-$C_6$) alkylcarbonyl group;
(f16) a ($C_3$-$C_6$) cycloalkylcarbonyl group;
(f17) a ($C_1$-$C_6$) alkoxycarbonyl group;
(f18) a ($C_1$-$C_6$) alkylthio ($C_1$-$C_6$) alkyl group;
(f19) a ($C_1$-$C_6$) alkylsulfinyl ($C_1$-$C_6$) alkyl group;
(f20) a ($C_1$-$C_6$) alkylsulfonyl ($C_1$-$C_6$) alkyl group;
(f21) a ($C_2$-$C_6$) alkenyl group;
(f22) a ($C_2$-$C_6$) alkynyl group;
(f23) a ($C_1$-$C_6$) alkylsulfinyl group;
(f24) a halo ($C_1$-$C_6$) alkylsulfinyl group;
(f25) a ($C_1$-$C_6$) alkylsulfonyl group;
(f26) a halo ($C_1$-$C_6$) alkylsulfonyl group;
(f27) a phenyl group; or
(f28) a substituted phenyl group having, on the ring, 1 to 5 substituents selected from a halogen atom, a nitro group, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_2$-$C_6$) alkenyl group, a halo ($C_2$-$C_6$) alkenyl group, a ($C_2$-$C_6$) alkynyl group, a ($C_3$-$C_6$) cycloalkyl group, a ($C_2$-$C_6$) alkenyloxy group, a halo ($C_2$-$C_6$) alkenyloxy group, a ($C_1$-$C_6$) alkylthio group, a halo ($C_1$-$C_6$) alkylthio group, a ($C_1$-$C_6$) alkylsulfonyloxy group, a halo ($C_1$-$C_6$) alkylsulfonyloxy group, a ($C_1$-$C_6$) alkylsulfinyl group, a halo ($C_1$-$C_6$) alkylsulfinyl group, a ($C_1$-$C_6$) alkylsulfonyl group, a halo ($C_1$-$C_6$) alkylsulfonyl group, a ($C_2$-$C_6$) alkenylthio group, a halo ($C_2$-$C_6$) alkenylthio group, a ($C_2$-$C_6$) alkenylsulfinyl group, a halo ($C_2$-$C_6$) alkenylsulfinyl group, a ($C_2$-$C_6$) alkenylsulfonyl group, a halo ($C_2$-$C_6$) alkenylsulfonyl group, a mono-($C_1$-$C_6$) alkylamino group, a di-($C_1$-$C_6$) alkylamino group (wherein the alkyl groups may be the same or different), a ($C_1$-$C_6$) alkylsulfonylamino group, a halo ($C_1$-$C_6$) alkylsulfonylamino group, a ($C_1$-$C_6$) alkylcarbonyl group, a halo ($C_1$-$C_6$) alkylcarbonyl group, a ($C_1$-$C_6$) alkyloxycarbonyl group, and a phenyl group,
wherein, when the number of the substituents is more than one, these substituents may be the same or different,
$R^7$ represents
(g1) a hydrogen atom;
(g2) a halogen atom;
(g3) a ($C_1$-$C_6$) alkyl group;
(g4) a halo ($C_1$-$C_6$) alkyl group;
(g5) a ($C_1$-$C_6$) alkoxy group;
(g6) a halo ($C_1$-$C_6$) alkoxy group;
(g7) a ($C_1$-$C_6$) alkylthio group;
(g8) a halo ($C_1$-$C_6$) alkylthio group;
(g9) a cyano ($C_1$-$C_6$) alkyl group;
(g10) a ($C_3$-$C_6$) cycloalkyl group;
(g11) a ($C_3$-$C_6$) cycloalkyl ($C_1$-$C_6$) alkyl group;
(g12) a ($C_1$-$C_6$) alkoxy ($C_1$-$C_6$) alkyl group;
(g13) a ($C_1$-$C_6$) alkoxycarbonyl ($C_1$-$C_6$) alkyl group;
(g14) a ($C_1$-$C_6$) alkylcarbonyl group;
(g15) a halo ($C_1$-$C_6$) alkylcarbonyl group;
(g16) a ($C_3$-$C_6$) cycloalkylcarbonyl group;
(g17) a ($C_1$-$C_6$) alkoxycarbonyl group;
(g18) a ($C_1$-$C_6$) alkylthio ($C_1$-$C_6$) alkyl group;
(g19) a ($C_1$-$C_6$) alkylsulfinyl ($C_1$-$C_6$) alkyl group;
(g20) a ($C_1$-$C_6$) alkylsulfonyl ($C_1$-$C_6$) alkyl group;
(g21) a ($C_2$-$C_6$) alkenyl group;
(g22) a ($C_2$-$C_6$) alkynyl group;
(g23) a ($C_1$-$C_6$) alkylsulfinyl group;
(g24) a halo ($C_1$-$C_6$) alkylsulfinyl group;
(g25) a ($C_1$-$C_6$) alkylsulfonyl group;
(g26) a halo ($C_1$-$C_6$) alkylsulfonyl group;
(g27) a phenyl group;
(g28) a substituted phenyl group having, on the ring, 1 to 5 substituents selected from a halogen atom, a nitro group, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_2$-$C_6$) alkenyl group, a halo ($C_2$-$C_6$) alkenyl group, a ($C_2$-$C_6$) alkynyl group, a ($C_3$-$C_6$) cycloalkyl group, a ($C_2$-$C_6$) alkenyloxy group, a halo ($C_2$-$C_6$) alkenyloxy group, a ($C_1$-$C_6$) alkylthio group, a halo ($C_1$-$C_6$) alkylthio group, a ($C_1$-$C_6$) alkylsulfonyloxy group, a halo ($C_1$-$C_6$) alkylsulfonyloxy group, a ($C_1$-$C_6$) alkylsulfinyl group, a halo ($C_1$-$C_6$) alkylsulfinyl group, a ($C_1$-$C_6$) alkylsulfonyl group, a halo ($C_1$-$C_6$) alkylsulfonyl group, a ($C_2$-$C_6$) alkenylthio group, a halo ($C_2$-$C_6$) alkenylthio group, a ($C_2$-$C_6$) alkenylsulfinyl group, a halo ($C_2$-$C_6$) alkenylsulfinyl group, a ($C_2$-$C_6$) alkenylsulfonyl group, a halo ($C_2$-$C_6$) alkenylsulfonyl group, a mono-($C_1$-$C_6$) alkylamino group, a di-($C_1$-$C_6$) alkylamino group (wherein the alkyl groups may be the same or different), a ($C_1$-$C_6$) alkylsulfonylamino group, a halo ($C_1$-$C_6$) alkylsulfonylamino group, a ($C_1$-$C_6$) alkylcarbonyl group, a halo ($C_1$-$C_6$) alkylcarbonyl group, a ($C_1$-$C_6$) alkyloxycarbonyl group, and a phenyl group,
wherein, when the number of the substituents is more than one, these substituents may be the same or different;
(g29) a heterocyclic group; or
(g30) a heterocyclic group having, on the ring, 1 to 3 substituents selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group, and a halo ($C_1$-$C_6$) alkylsulfonyl group,
wherein, when the number of the substituents is more than one, these substituents may be the same or different, and
$R^8$ represents
(h1) a hydrogen atom;
(h2) a halogen atom;
(h3) a ($C_1$-$C_6$) alkyl group;
(h4) a halo ($C_1$-$C_6$) alkyl group;
(h5) a ($C_1$-$C_6$) alkoxy group;
(h6) a halo ($C_1$-$C_6$) alkoxy group;
(h7) a ($C_1$-$C_6$) alkylthio group;
(h8) a halo ($C_1$-$C_6$) alkylthio group;
(h9) a cyano ($C_1$-$C_6$) alkyl group;
(h10) a ($C_3$-$C_6$) cycloalkyl group;
(h11) a ($C_3$-$C_6$) cycloalkyl ($C_1$-$C_6$) alkyl group;
(h12) a ($C_1$-$C_6$) alkoxy ($C_1$-$C_6$) alkyl group;
(h13) a ($C_1$-$C_6$) alkoxycarbonyl ($C_1$-$C_6$) alkyl group;
(h14) a ($C_1$-$C_6$) alkylcarbonyl group;
(h15) a halo ($C_1$-$C_6$) alkylcarbonyl group;
(h16) a ($C_3$-$C_6$) cycloalkylcarbonyl group;
(h17) a ($C_1$-$C_6$) alkoxycarbonyl group;
(h18) a ($C_1$-$C_6$) alkylthio ($C_1$-$C_6$) alkyl group;
(h19) a ($C_1$-$C_6$) alkylsulfinyl ($C_1$-$C_6$) alkyl group;
(h20) a ($C_1$-$C_6$) alkylsulfonyl ($C_1$-$C_6$) alkyl group;
(h21) a ($C_2$-$C_6$) alkenyl group;
(h22) a ($C_2$-$C_6$) alkynyl group;
(h23) a ($C_1$-$C_6$) alkylsulfinyl group;

(h24) a halo ($C_1$-$C_6$) alkylsulfinyl group;
(h25) a ($C_1$-$C_6$) alkylsulfonyl group; or
(h26) a halo ($C_1$-$C_6$) alkylsulfonyl group},
or a salt thereof.

[2] The amide compound or the salt according to the above [1], wherein $A^1$, $A^3$, and $A^4$ each represent C—$R^2$,
  $R^2$ represents (b1) a hydrogen atom,
  $A^2$ represents C—$R^3$, and
  $R^3$ represents (c1) a halogen atom or (c4) a halo ($C_1$-$C_6$) alkyl group.

[3] The amide compound or the salt according to the above [1] or [2], wherein $R^3$ represents
(c2) a ($C_1$-$C_6$) alkyl group or
(c4) a halo ($C_1$-$C_3$) alkyl group, and
  $R^4$ represents
(d1) a hydrogen atom;
(d2) a ($C_1$-$C_6$) alkyl group;
(d7) a ($C_1$-$C_6$) alkoxy ($C_1$-$C_6$) alkyl group;
(d9) a ($C_1$-$C_6$) alkylcarbonyl group;
(d10) a halo ($C_1$-$C_6$) alkylcarbonyl group;
(d11) a ($C_3$-$C_6$) cycloalkylcarbonyl group;
(d12) a ($C_1$-$C_6$) alkoxycarbonyl group;
(d17) a ($C_2$-$C_6$) alkenyl group;
(d18) a ($C_2$-$C_6$) alkynyl group;
(d19) a ($C_1$-$C_6$) alkylsulfonyl group; or
(d20) a halo ($C_1$-$C_6$) alkylsulfonyl group.

[4] The amide compound or the salt according to any one of the above [1] to [3], wherein
  $A^1$, $A^3$, and $A^4$ each represent C—$R^2$,
  $R^2$ represents (b1) a hydrogen atom,
  $R^3$ represents (c4) a halo ($C_1$-$C_3$) alkyl group,
  $R^4$ represents
(d2) a ($C_1$-$C_6$) alkyl group;
(d9) a ($C_1$-$C_6$) alkylcarbonyl group;
(d10) a halo ($C_1$-$C_6$) alkylcarbonyl group; or
(d11) a ($C_3$-$C_6$) cycloalkylcarbonyl group,
  $A^5$ represents an oxygen atom, a sulfur atom, or a C—$R^5$ group,
  $A^6$ represents an oxygen atom, a sulfur atom, or a C—$R^6$ group,
with the proviso that, when either $A^5$ or $A^6$ represents an oxygen atom or a sulfur atom, the other does not represent an oxygen atom or a sulfur atom at the same time, or $A^5$ and $A^6$ do not represent the same substituent,
  $A^7$ represents a C—$R^7$ group,
  $A^8$ represents a C—$R^8$ group,
  $R^5$ represents
(e2) a halogen atom;
(e3) a ($C_1$-$C_6$) alkyl group;
(e4) a halo ($C_1$-$C_6$) alkyl group;
(e10) a ($C_3$-$C_6$) cycloalkyl group;
(e14) a ($C_1$-$C_6$) alkylcarbonyl group;
(e15) a halo ($C_1$-$C_6$) alkylcarbonyl group;
(e16) a ($C_3$-$C_6$) cycloalkylcarbonyl group;
(e17) a carboxyl group;
(e18) a ($C_1$-$C_6$) alkoxycarbonyl group; or
(e24) a ($C_2$-$C_6$) alkenyl group,
  $R^6$ represents
(f3) a ($C_1$-$C_6$) alkyl group or
(f4) a halo ($C_1$-$C_6$) alkyl group,
  $R^7$ represents
(g1) a hydrogen atom;
(g2) a halogen atom;
(g3) a ($C_1$-$C_6$) alkyl group;
(g4) a halo ($C_1$-$C_6$) alkyl group;
(g5) a ($C_1$-$C_6$) alkoxy group;
(g6) a halo ($C_1$-$C_6$) alkoxy group;
(g7) a ($C_1$-$C_6$) alkylthio group;
(g8) a halo ($C_1$-$C_6$) alkylthio group;
(g10) a ($C_3$-$C_6$) cycloalkyl group;
(g14) a ($C_1$-$C_6$) alkylcarbonyl group;
(g15) a halo ($C_1$-$C_6$) alkylcarbonyl group;
(g16) a ($C_3$-$C_6$) cycloalkylcarbonyl group; or
(g17) a ($C_1$-$C_6$) alkoxycarbonyl group, and
  $R^8$ represents
(h1) a hydrogen atom;
(h2) a halogen atom;
(h3) a ($C_1$-$C_6$) alkyl group;
(h4) a halo ($C_1$-$C_6$) alkyl group;
(h5) a ($C_1$-$C_6$) alkoxy group;
(h6) a halo ($C_1$-$C_6$) alkoxy group;
(h7) a ($C_1$-$C_6$) alkylthio group;
(h8) a halo ($C_1$-$C_6$) alkylthio group;
(h10) a ($C_3$-$C_6$) cycloalkyl group;
(h14) a ($C_1$-$C_6$) alkylcarbonyl group;
(h15) a halo ($C_1$-$C_6$) alkylcarbonyl group;
(h16) a ($C_3$-$C_6$) cycloalkylcarbonyl group; or
(h17) a ($C_1$-$C_6$) alkoxycarbonyl group.

[5] The amide compound or the salt according to any one of the above [1] to [4], wherein
  $A^5$ represents a C—$R^5$ group,
  $A^6$ represents an oxygen atom or a sulfur atom,
  $R^5$ represents
(e2) a halogen atom;
(e3) a ($C_1$-$C_6$) alkyl group;
(e4) a halo ($C_1$-$C_6$) alkyl group;
(e10) a ($C_3$-$C_6$) cycloalkyl group;
(e17) a carboxyl group;
(e18) a ($C_1$-$C_3$) alkoxycarbonyl group; or
(e24) a ($C_2$-$C_6$) alkenyl group,
  $R^6$ represents
(f3) a ($C_1$-$C_3$) alkyl group or
(f4) a halo ($C_1$-$C_3$) alkyl group,
  $R^7$ represents
(g1) a hydrogen atom;
(g3) a ($C_1$-$C_6$) alkyl group; or
(g4) a halo ($C_1$-$C_6$) alkyl group, and
  $R^8$ represents (h1) a hydrogen atom.

[6] The amide compound or the salt according to any one of the above [1] to [4], wherein
  $A^5$ represents an oxygen atom or a sulfur atom,
  $A^6$ represents a C—$R^6$ group,
  $R^5$ represents
(e3) a ($C_1$-$C_6$) alkyl group or
(e4) a halo ($C_1$-$C_6$) alkyl group,
  $R^6$ represents
(f3) a ($C_1$-$C_3$) alkyl group or
(f4) a halo ($C_1$-$C_3$) alkyl group,
  $R^7$ represents
(g1) a hydrogen atom;
(g2) a halogen atom;
(g3) a ($C_1$-$C_6$) alkyl group; or
(g4) a halo ($C_1$-$C_6$) alkyl group, and
  $R^8$ represents
(h2) a halogen atom;
(h3) a ($C_1$-$C_6$) alkyl group;
(h4) a halo ($C_1$-$C_6$) alkyl group;
(h5) a ($C_1$-$C_6$) alkoxy group;
(h6) a halo ($C_1$-$C_6$) alkoxy group;
(h7) a ($C_1$-$C_6$) alkylthio group;
(h8) a halo ($C_1$-$C_6$) alkylthio group; or
(h17) a ($C_1$-$C_6$) alkoxycarbonyl group.

[7] The amide compound or the salt according to any one of the above [1] to [6], wherein the halogen atom of the haloalkyl group is fluorine.

[8] An agricultural and horticultural microbicide comprising the amide compound or the salt according to any one of the above [1] to [7] as an active ingredient.

[9] Use of the amide compound or the salt according to any one of the above [1] to [7] as an agricultural and horticultural microbicide.

[10] A method for using an agricultural and horticultural microbicide, the method comprising treating plants or soil with the active ingredient of the agricultural and horticultural microbicide according to the above [8].

[11] A method for controlling an agricultural and horticultural disease, the method comprising treating plants or soil with an effective amount of the agricultural and horticultural microbicide according to the above [8].

[12] The method according to the above [11], wherein the agricultural and horticultural disease is powdery mildew.

Advantageous Effects of Invention

The amide compound of the present invention or a salt thereof is highly effective as an agricultural and horticultural microbicide. In particular, the amide compound of the present invention or a salt thereof is highly effective against powdery mildew of barley and wheat. In addition, the amide compound of the present invention or a salt thereof produces an effect even in the vicinity of the application site, which effect is uniformly distributed and long-lasting.

DESCRIPTION OF EMBODIMENTS

In the definitions of the general formula [I] representing the amide compound of the present invention or a salt thereof, "halo" refers to a "halogen atom" and represents a chlorine atom, a bromine atom, an iodine atom or a fluorine atom.

The alkyl group herein may be a "($C_1$-$C_{10}$) alkyl group" and is preferably a "($C_1$-$C_6$) alkyl group". The "($C_1$-$C_{10}$) alkyl group" or the "($C_1$-$C_6$) alkyl group" refers to a straight-chain or branched-chain alkyl group of 1 to 10 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, an 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group, a n-octyl group, a n-decyl group, or the like. The "($C_2$-$C_6$) alkenyl group" refers to a straight-chain or branched-chain alkenyl group of 2 to 6 carbon atoms, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a 3,3-dimethyl-1-butenyl group, or the like. The "($C_2$-$C_6$) alkynyl group" refers to a straight-chain or branched-chain alkynyl group of 2 to 6 carbon atoms, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, a 3,3-dimethyl-1-butynyl group, or the like.

The "($C_3$-$C_6$) cycloalkyl group" refers to a cyclic alkyl group of 3 to 6 carbon atoms, for example, a cyclopropyl group, a cyclobutyl group, a cyclopentyl group, a cyclohexyl group, or the like. The "($C_1$-$C_6$) alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, an 1-ethylpropyloxy group, a 1-methylbutyloxy group, a n-hexyloxy group, an isohexyloxy group, a 1,1,2-trimethylpropyloxy group, or the like.

The "($C_1$-$C_6$) alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, an 1-ethylpropylthio group, a 1-methylbutylthio group, a n-hexylthio group, an isohexylthio group, a 1,1,2-trimethylpropylthio group, or the like. The "($C_1$-$C_6$) alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, an 1-ethylpropylsulfinyl group, a 1-methylbutylsulfinyl group, a n-hexylsulfinyl group, an isohexylsulfinyl group, a 1,1,2-trimethylpropylsulfinyl group, or the like. The "($C_1$-$C_6$) alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, an 1-ethylpropylsulfonyl group, a 1-methylbutylsulfonyl group, a n-hexylsulfonyl group, an isohexylsulfonyl group, a 1,1,2-trimethylpropylsulfonyl group, or the like.

The above-mentioned "($C_1$-$C_6$) alkyl group", "($C_3$-$C_6$) cycloalkyl group", "($C_1$-$C_6$) alkoxy group", "($C_1$-$C_6$) alkylthio group", "($C_1$-$C_6$) alkylsulfinyl group", and "($C_1$-$C_6$) alkylsulfonyl group" may be substituted with one or more halogen atoms at a substitutable position(s), and in the case where any of the above-listed groups is substituted with two or more halogen atoms, the halogen atoms may be the same or different.

The above-mentioned "groups substituted with one or more halogen atoms at a substitutable position(s)" are expressed as a "halo ($C_1$-$C_6$) alkyl group", a "halo ($C_3$-$C_6$) cycloalkyl group", a "halo ($C_1$-$C_6$) alkoxy group", a "halo ($C_1$-$C_6$) alkylthio group", a "halo ($C_1$-$C_6$) alkylsulfinyl group", and a "halo ($C_1$-$C_6$) alkylsulfonyl group".

Examples of the "halo ($C_1$-$C_6$) alkyl group" include a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the "halo $(C_1-C_6)$ alkoxy group" include a difluoromethoxy group, a trifluoromethoxy group, a 2,2,2-trifluoroethoxy group, a 2,2,2-trichloroethoxy group, a 2,2,3,3-tetrafluoropropoxy group, and a 2,2,3,3,4,4,4-hexafluorobutoxy group.

Examples of the "cyano $(C_1-C_6)$ alkyl group" include a cyanomethyl group, a 1-cyanoethyl group, a 2-cyanoethyl group, a 3-cyanopropyl group, a 2-cyanopropyl group, a 1-cyanopropyl group, a 1-cyano-1-methylethyl group, a 2-cyanobutyl group, and a 2-cyanohexyl group.

The expressions "$(C_1-C_6)$", "$(C_2-C_6)$", "$(C_3-C_6)$", etc. each refer to the range of the number of carbon atoms in each group. The same definition holds true for groups in which two or more of the above-mentioned groups are coupled together, and for example, the "$(C_1-C_6)$ alkoxy $(C_1-C_6)$ alkyl group" means that a straight-chain or branched-chain alkoxy group of 1 to 6 carbon atoms is bound to a straight-chain or branched-chain alkyl group of 1 to 6 carbon atoms.

The "aryl group" refers to a group derived from an aromatic hydrocarbon. Examples of the "alkylaryl group" include a phenyl group, a toluyl group, a xylyl group, a naphthyl group, an anthracenyl group, a phenanthrenyl group, an indacenyl group, and a pentalenyl group.

The "heterocyclic group" and the "heterocyclic ring" refer to, for example, a 5- or 6-membered monocyclic aromatic heterocyclic group or a 4- or 6-membered monocyclic non-aromatic heterocyclic group each of which contains, as ring atoms, one or more carbon atoms and 1 to 4 heteroatoms selected from an oxygen atom, a sulfur atom and a nitrogen atom.

Examples of the aromatic heterocyclic group include monocyclic aromatic heterocyclic groups such as furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl, and triazinyl.

Examples of the "non-aromatic heterocyclic group" include monocyclic non-aromatic heterocyclic groups such as oxetanyl, thietanyl, azetidinyl, pyrrolidinyl, piperidinyl, morpholinyl, thiomorpholinyl, piperazinyl, hexamethyleneiminyl, oxazolidinyl, thiazolidinyl, imidazolidinyl, oxazolinyl, thiazolinyl, isoxazolinyl, imidazolinyl, dioxolyl, dioxolanyl, dihydrooxadiazolyl, 2-oxo-pyrrolidin-1-yl, 2-oxo-1,3-oxazolidin-5-yl, 5-oxo-1,2,4-oxadiazolin-3-yl, 1,3-dioxolan-2-yl, 1,3-dioxan-2-yl, 1,3-dioxepan-2-yl, pyranyl, tetrahydropyranyl, thiopyranyl, tetrahydrothiopyranyl, 1-oxide tetrahydrothiopyranyl, 1,1-dioxide tetrahydrothiopyranyl, tetrahydrofuranyl, dioxanyl, pyrazolidinyl, pyrazolinyl, tetrahydropyrimidinyl, dihydrotriazolyl, and tetrahydrotriazolyl.

Examples of the salt of the amide compound represented by the general formula [I] of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The amide compound represented by the general formula [I] of the present invention and a salt thereof can have one or more chiral centers in the structural formula and can exist as two or more kinds of optical isomers or diastereomers. All the optical isomers and mixtures of the isomers at any ratio are also included in the present invention. Further, the compound represented by the general formula [I] of the present invention and a salt thereof can exist as two kinds of geometric isomers due to a carbon-carbon double bond in the structural formula. All the geometric isomers and mixtures of the isomers at any ratio are also included in the present invention.

In the formula [I], the heterocyclic ring represented by

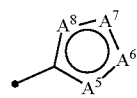

[Chem. 2]

(wherein $A^5$, $A^6$, $A^7$, and $A^8$ are as defined above)
is exemplified by the following heterocyclic rings:

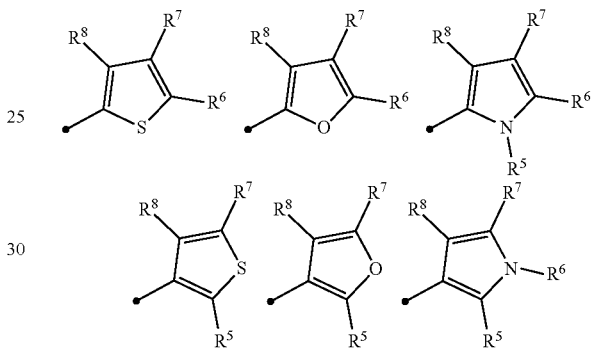

[Chem. 3]

(wherein $R^5$, $R^6$, $R^7$, and $R^8$ are as defined above)

In preferable embodiments for use as a microbicide, the amide compound represented by the general formula [I] of the present invention or a salt thereof is defined as follows.

$R^1$ is preferably a $(C_1-C_6)$ alkyl group, more preferably a $(C_2-C_4)$ alkyl group, and most preferably an ethyl group.

m is preferably 0 or 2, and more preferably 2.

$R^3$ is preferably a halogen atom or a halo $(C_1-C_6)$ alkyl group, more preferably a halo $(C_1-C_6)$ alkyl group, still more preferably a fluoro $(C_1-C_3)$ alkyl group, and most preferably a trifluoromethyl group.

$R^4$ is preferably a $(C_1-C_6)$ alkyl group, a $(C_1-C_3)$ alkylcarbonyl group, or a $(C_3-C_6)$ cycloalkylcarbonyl group, more preferably a $(C_1-C_3)$ alkylcarbonyl group, and most preferably an acetyl group.

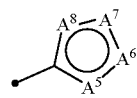

[Chem. 4]

The above partial structure in the formula [I] is preferably an optionally substituted pyrrole ring, an optionally substituted thiazole ring, an optionally substituted furan ring, or an optionally substituted thiophene ring. A more preferable embodiment is an optionally substituted furan ring, and another more preferable embodiment is an optionally substituted thiophene ring.

The above partial structure in the formula [I] is particularly preferably a structure represented by the formula shown below, in which $A^6$ is a sulfur atom or an oxygen atom

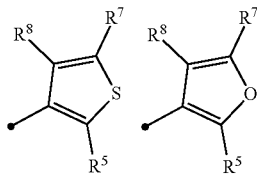
[Chem. 5]

(wherein
$R^5$ represents
(e2) a halogen atom;
(e3) a $(C_1-C_6)$ alkyl group;
(e4) a halo $(C_1-C_6)$ alkyl group;
(e10) a $(C_3-C_6)$ cycloalkyl group;
(e17) a carboxyl group;
(e18) a $(C_1-C_6)$ alkoxycarbonyl group; or
(e24) a $(C_2-C_6)$ alkenyl group,
$R^7$ represents
(g1) a hydrogen atom;
(g3) a $(C_1-C_6)$ alkyl group; or
(g4) a halo $(C_1-C_6)$ alkyl group, and
$R^8$ represents a hydrogen atom).

The above partial structure in the formula [I] is most preferably a structure represented by the following formula:

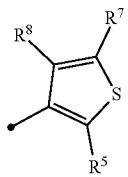
[Chem. 6]

(wherein
$R^5$ represents
(e2) a halogen atom;
(e3) a $(C_1-C_6)$ alkyl group;
(e4) a halo $(C_1-C_6)$ alkyl group;
(e10) a $(C_3-C_6)$ cycloalkyl group;
(e17) a carboxyl group;
(e18) a $(C_1-C_6)$ alkoxycarbonyl group; or
(e24) a $(C_2-C_6)$ alkenyl group,
$R^7$ represents
(g1) a hydrogen atom;
(g3) a $(C_1-C_6)$ alkyl group; or
(g4) a halo $(C_1-C_6)$ alkyl group, and
$R^8$ represents a hydrogen atom).

Another most preferable structure is as follows:

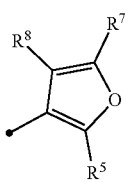
[Chem. 7]

(wherein
$R^5$ represents
(e2) a halogen atom;
(e3) a $(C_1-C_6)$ alkyl group;
(e4) a halo $(C_1-C_6)$ alkyl group;
(e10) a $(C_3-C_6)$ cycloalkyl group;
(e17) a carboxyl group;
(e18) a $(C_1-C_6)$ alkoxycarbonyl group; or
(e24) a $(C_2-C_6)$ alkenyl group,
$R^7$ represents
(g1) a hydrogen atom;
(g3) a $(C_1-C_6)$ alkyl group; or
(g4) a halo $(C_1-C_6)$ alkyl group, and
$R^8$ represents a hydrogen atom).

Another most preferable structure is as follows:

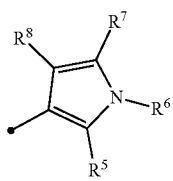
[Chem. 8]

(wherein
$R^5$ represents
(e2) a halogen atom;
(e3) a $(C_1-C_6)$ alkyl group;
(e4) a halo $(C_1-C_6)$ alkyl group;
(e10) a $(C_3-C_6)$ cycloalkyl group;
(e17) a carboxyl group;
(e18) a $(C_1-C_6)$ alkoxycarbonyl group; or
(e24) a $(C_2-C_6)$ alkenyl group,
$R^6$ represents
(f3) a $(C_1-C_3)$ alkyl group or
(f4) a halo $(C_1-C_3)$ alkyl group,
$R^7$ represents
(g1) a hydrogen atom;
(g3) a $(C_1-C_6)$ alkyl group; or
(g4) a halo $(C_1-C_6)$ alkyl group, and
$R^8$ represents a hydrogen atom).

When $A^6$ is an oxygen atom, a sulfur atom, or $N-R^6$ (wherein $R^6$ represents a $(C_1-C_6)$ alkyl group or a halo $(C_1-C_6)$ alkyl group),
$R^5$ is preferably
(e2) a halogen atom;
(e3) a $(C_1-C_6)$ alkyl group;
(e4) a halo $(C_1-C_6)$ alkyl group;
(e17) a carboxyl group;
(e10) a $(C_3-C_6)$ cycloalkyl group;
(e18) a $(C_1-C_6)$ alkoxycarbonyl group; or
(e24) a $(C_2-C_6)$ alkenyl group,
particularly preferably a fluorine atom, a chlorine atom, a bromine atom, an isopropyl group, a t-butyl group, a carboxyl group, a methoxycarbonyl group, an ethoxycarbonyl group, or a vinyl group, and
more preferably a bromine atom or a methoxycarbonyl group,
$R^7$ is preferably
(g1) a hydrogen atom;
(g3) a $(C_1-C_6)$ alkyl group; or
a perfluoro $(C_1-C_6)$ alkyl group,
and more preferably a hydrogen atom, a t-butyl group, a trifluoromethyl group, a pentafluoroethyl group, or a heptafluoroisopropyl group, and $R^8$ is preferably
(h1) a hydrogen atom;
(h2) a halogen atom;
(h5) a $(C_1-C_6)$ alkoxy group; or
(h17) a $(C_1-C_6)$ alkoxycarbonyl group, and
more preferably a hydrogen atom.

Another particularly preferable embodiment is as follows:

[Chem. 9]

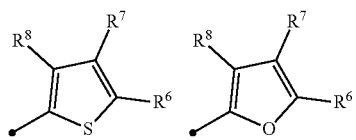

(wherein
$R^6$ represents
(f3) a $(C_1-C_6)$ alkyl group; or
(f4) a halo $(C_1-C_6)$ alkyl group,
$R^7$ represents
(g1) a hydrogen atom;
(g2) a halogen atom;
(g3) a $(C_1-C_6)$ alkyl group; or
(g4) a halo $(C_1-C_6)$ alkyl group, and
$R^8$ represents
(h2) a halogen atom;
(h3) a $(C_1-C_6)$ alkyl group;
(h4) a halo $(C_1-C_6)$ alkyl group;
(h5) a $(C_1-C_6)$ alkoxy group;
(h6) a halo $(C_1-C_6)$ alkoxy group;
(h7) a $(C_1-C_6)$ alkylthio group;
(h8) a halo $(C_1-C_6)$ alkylthio group; or
(h17) a $(C_1-C_6)$ alkoxycarbonyl group).

In this embodiment, a more preferable compound is represented by the above formula in which
$R^6$ is (f4) a halo $(C_1-C_3)$ alkyl group,
$R^7$ is (g1) a hydrogen atom, and
$R^8$ is
(h2) a halogen atom;
(h3) a $(C_1-C_6)$ alkyl group;
(h4) a halo $(C_1-C_6)$ alkyl group;
(h5) a $(C_1-C_6)$ alkoxy group; or
(h17) a $(C_1-C_6)$ alkoxycarbonyl group.

The amide compound represented by the general formula [I] of the present invention or a salt thereof can be produced according to, for example, the production methods described below, which are non-limiting examples.

Production Method 1

[Chem. 10]

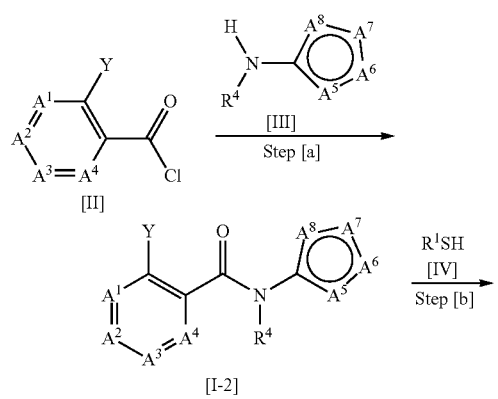

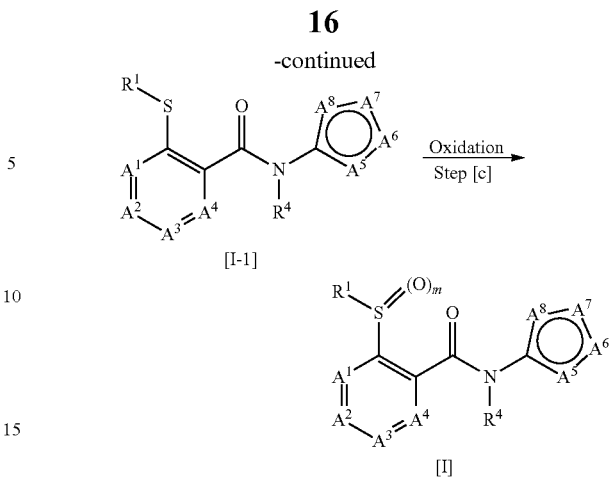

(In the formula, $R^1$, $R^4$, $A^1$, $A^2$, $A^3$, $A^4$, $A^5$, $A^6$, $A^7$, $A^8$, and m are as defined above, and Y represents a halogen atom.)

Production Method at Step [a]

The amide compound represented by the general formula [I-2] can be produced by reacting the carboxylic chloride represented by the general formula [II] with the amine compound represented by the general formula [III] in the presence of a base and an inert solvent. Since this reaction is an equimolar reaction of the compounds, they are basically used in equimolar amounts, but either of them may be used in an excess amount.

$R^4$ may be derived from a hydrogen atom by the usual alkylation, alkylcarbonylation, etc. after the reaction. Alternatively, $R^4$ may be protected with a modifying group prior to the reaction, followed by deprotection and subsequent alkylation or alkylcarbonylation, etc. That is, this reaction may be performed according to a known method or a method known per se.

The base used in this reaction may be an inorganic base or an organic base. Examples of the inorganic base include alkali metal hydroxides such as sodium hydroxide and potassium hydroxide; alkali metal hydrides such as sodium hydride and potassium hydride; alkali metal alkoxides such as sodium ethoxide and potassium t-butoxide; and carbonates such as sodium carbonate, potassium carbonate, and sodium hydrogen carbonate. Examples of the organic base include triethylamine, pyridine, and DBU. The amount of the base used is an equimolar or excess molar amount relative to the carboxylic chloride represented by the general formula [II].

The inert solvent used in this reaction may be any solvent that does not markedly inhibit the reaction, and examples include aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; straight-chain or cyclic ethers such as diethyl ether, dioxane and tetrahydrofuran; esters such as ethyl acetate; amides such as dimethylformamide and dimethylacetamide; and others such as dimethyl sulfoxide, 1,3-dimethyl-2-imidazolidinone, acetone and methyl ethyl ketone. One of these inert solvents may be used alone, and also two or more of them may be used as a mixture.

This reaction may be performed under the atmosphere of an inert gas such as nitrogen gas and argon gas. The reaction temperature may be in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of interest. Alternatively, the isolated product may be subjected to the next step without purification.

Production Method at Step [b]

The amide compound represented by the general formula [I-1] can be produced by reacting the amide compound represented by the general formula [I-2] with the thiol compound represented by the general formula [IV] in the presence of a base in an inert solvent.

Since this reaction is an equimolar reaction of the compounds, they are basically used in equimolar amounts, but either of them may be used in an excess amount.

Examples of the base that can be used in this reaction include inorganic basic salts such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually in the range of about 1- to 5-fold molar equivalents relative to the amide compound represented by the general formula [I-2]. Commercially available products of sodium methanethiolate or sodium ethanethiolate can also be used as the base, and in this case, compound [IV] does not have to be used.

The inert solvent used in this reaction may be any solvent that does not markedly inhibit the reaction, and examples include alcohols such as methanol, ethanol, propanol, butanol and 2-propanol; straight-chain or cyclic ethers such as diethyl ether, tetrahydrofuran and dioxane; aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; and polar solvents such as N,N-dimethylformamide, N,N-dimethylacetamide, dimethyl sulfoxide and 1,3-dimethyl-2-imidazolidinone. One of these inert solvents may be used alone, and also two or more of them may be used as a mixture.

This reaction may be performed under the atmosphere of an inert gas such as nitrogen gas and argon gas. The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest. Alternatively, the isolated product may be subjected to the next step without purification.

Production method at step [c]

The amide compound represented by the general formula [I] can be produced by reacting the amide compound represented by the general formula [I-1] with an oxidizing agent in an inert solvent. Examples of the oxidizing agent used in this reaction include peroxides such as a hydrogen peroxide solution, perbenzoic acid and m-chloroperoxybenzoic acid. The amount of the oxidizing agent used is appropriately selected from the range of 0.8- to 5-fold molar equivalents relative to the amide compound represented by the general formula [I-1], and is preferably in the range of 1- to 2-fold molar equivalents.

The inert solvent used in this reaction may be any solvent that does not markedly inhibit the reaction, and examples include straight-chain or cyclic ethers such as diethyl ether, tetrahydrofuran and dioxane; aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. One of these inert solvents may be used alone, and also two or more of them may be used as a mixture.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest.

The starting material or the intermediates of the present invention can be produced according to, for example, the following methods. These compounds can be produced by known methods or methods known per se.

Production Method of Intermediate [III]

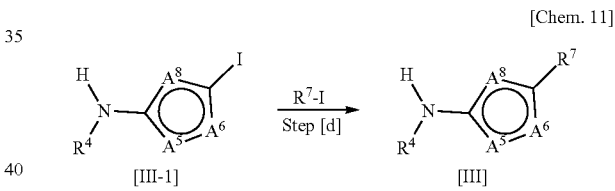

[Chem. 11]

(In the formula, $R^4$, $R^7$, $A^5$, $A^6$, and $A^8$ are as defined above.)

Production Method at Step [d]

The compound represented by the general formula [III] can be produced from the corresponding iodinated compound [III-1] according to the method described in JP-A 11-302233 or WO 2013/018928.

Production Method of Intermediate [II-1]

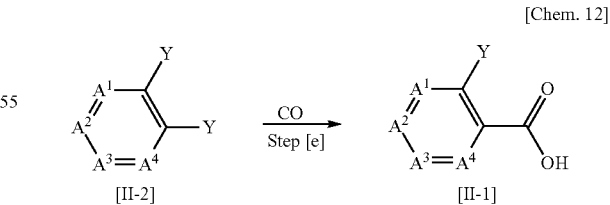

[Chem. 12]

(In the formula, $A^1$, $A^2$, $A^3$, and $A^4$ are as defined above, and Y represents a halogen atom.)

Production Method at Step [e]

The compound represented by the general formula [II-1] can be synthesized from the corresponding halogenated compound [II-2] according to the method described in JP-A 2005-272338. The compound represented by the general formula [II-1] can be converted to the carboxylic chloride [II] according to the usual method.
Production Method 2

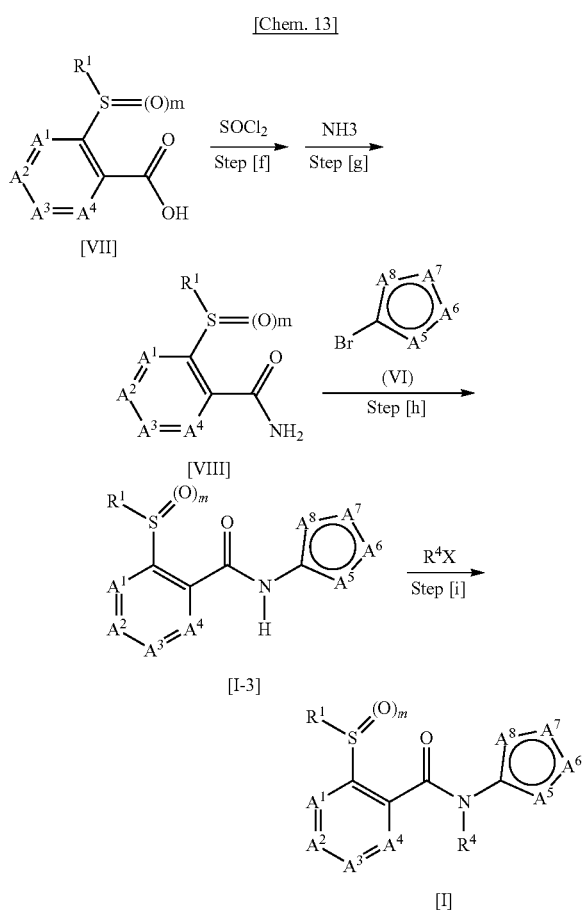

(In the formula, $R^1$, $R^4$, $A^1$, $A^2$, $A^3$, $A^4$, $A^5$, $A^6$, $A^7$, $A^1$, and m are as defined above, and X represents a leaving group.)

X preferably represents a substituent such as halogen, tosyl, mesyl, or trifluoromethanesulfonate, but is not limited thereto.

Production Method at Step [f]

The carboxylic acid compound of the general formula [VII] can be converted to a carboxylic halide. Examples of the agent for halogenation include thionyl chloride, sulfuryl chloride, oxalyl chloride, phosphoryl chloride, and phosphoryl bromide. In the case where a solvent is used for the reaction, the solvent is, for example, a halogenated aliphatic hydrocarbon, such as chloroform or dichloromethane, or a halogenated aromatic hydrocarbon, such as chlorobenzene or dichlorobenzene. The reaction temperature is, for example, 0° C. to the reflux temperature.

Production Method at Step [g]

The carboxylic amide represented by the general formula [VIII] can be produced by reacting the carboxylic halide obtained at step [f] with ammonia in the presence of a base and an inert solvent. Since this reaction is an equimolar reaction of the compounds, they are basically used in equimolar amounts, but either of them may be used in an excess amount. Usually, ammonia is used in an excess amount.

The base used in this reaction may be an inorganic base or an organic base. Examples of the inorganic base include alkali metal hydroxides such as sodium hydroxide and potassium hydroxide; alkali metal hydrides such as sodium hydride and potassium hydride; alkali metal alkoxides such as sodium ethoxide and potassium t-butoxide; and carbonates such as sodium carbonate, potassium carbonate, and sodium hydrogen carbonate. Examples of the organic base include triethylamine, pyridine, and DBU. The amount of the base used is an equimolar or excess molar amount relative to the carboxylic halide.

The inert solvent used in this reaction may be any solvent that does not markedly inhibit the reaction, and examples include aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; straight-chain or cyclic ethers such as diethyl ether, dioxane and tetrahydrofuran; esters such as ethyl acetate; amides such as dimethylformamide and dimethylacetamide; and others such as dimethyl sulfoxide, 1,3-dimethyl-2-imidazolidinone, acetone, methyl ethyl ketone, and water. One of these inert solvents may be used alone, and also two or more of them may be used as a mixture.

This reaction may be performed under the atmosphere of an inert gas such as nitrogen gas and argon gas. The reaction temperature may be in the range of room temperature to the boiling point of the inert solvent used. The reaction time varies with the reaction scale and the reaction temperature, but is basically in the range of a few minutes to 48 hours. After the reaction is completed, the compound of interest is isolated from the post-reaction mixture by the usual method. As needed, recrystallization, column chromatography, etc. can be employed for the purification of the compound of interest. Alternatively, the isolated product may be subjected to the next step without purification.

Production Method at Step [h]

The compound of the general formula [I-3] can be produced by, for example, Buchwald coupling of the carboxylic amide of the general formula [VIII] with the halogenated (brominated) 5-membered ring compound of the general formula [VI] in the presence of a base and a catalyst. Here, the bromide is used as a representative, but other halides may be used. The solvent used in this reaction may be any solvent that does not markedly inhibit the reaction, and examples include inert solvents such as aromatic hydrocarbons such as toluene and xylene; and straight-chain or cyclic ethers such as 1,4-dioxane, tetrahydrofuran, and cyclopentyl methyl ether.

Examples of the base used in this reaction include cesium carbonate, sodium bis(trimethylsilyl)amide, and tert-butoxide. Examples of the catalyst include a combination of tris(dibenzylidene-acetone)dipalladium(0) and Xantphos (4,5-bis(diphenylphosphino)-9,9-dimethylxanthene).

Production Method at Step [i]

The amide compound represented by the general formula [I] can be produced by reacting the amide compound represented by the general formula [I-3] with the compound represented by the general formula $R^4X$ in the presence of a base and an inert solvent.

The compounds represented by, for example, the general formulae [I-4] and [I-5] described later, can also be produced by the same production methods as those for the compounds of the above general formulae [I-3] and [I]. More specific descriptions are given in Examples below, but the production method according to the present invention is not limited thereto.

Examples of the base used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; alkali metal alkoxides such as sodium methoxide, sodium ethoxide and potassium tert-butoxide; alkyllithiums such as methyllithium and n-butyllithium; and organic bases such as triethylamine, pyridine, and diazabicycloundecen (DBU). The amount of the base used is an equimolar or excess molar amount relative to the amide compound represented by the general formula [I-3].

Since this reaction is an equimolar reaction of the compounds, they are basically used in equimolar amounts, but either of them may be used in an excess amount.

The inert solvent used in this reaction may be any solvent that does not markedly inhibit the reaction, and examples include straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide and 1,3-dimethyl-2-imidazolidinone. One of these solvents may be used alone, and also two or more of them may be used as a mixture.

This reaction may be performed under the atmosphere of an inert gas such as nitrogen gas and argon gas. The reaction temperature may be in the range of room temperature to the boiling point of the inert solvent used. The reaction time varies with the reaction scale and the reaction temperature, but is basically in the range of a few minutes to 48 hours. After the reaction is completed, the compound of interest is isolated from the post-reaction mixture by the usual method. As needed, recrystallization, column chromatography, etc. can be employed for the purification of the compound of interest.

The agricultural and horticultural microbicide comprising the amide compound represented by the general formula [I] of the present invention or a salt thereof as an active ingredient is suitable for controlling diseases which may infest cereals, fruit trees, vegetables, other crops, and ornamental flowering plants.

The target diseases include filamentous fungal diseases, bacterial diseases, and viral diseases. Examples of the filamentous fungal diseases include diseases caused by fungi-imperfecti including the genera *Botrytis, Helminthosporium, Fusarium, Septoria, Cercospora, Pseudocercosporella, Rhynchosporium, Pyricularia* and *Alternaria*; diseases caused by basidiomycetes including the genera *Hemilelia, Rhizoctonia, Ustilago, Typhula* and *Puccinia*; diseases caused by ascomycota including the genera *Venturia, Podosphaera, Leptosphaeria, Blumeria, Erysiphe, Microdochium, Sclerotinia, Gaeumannomyces, Monilinia* and *Unsinula*; and diseases caused by other fungi including the genera *Ascochyta, Phoma, Pythium, Corticium* and *Pyrenophora*.

Specific examples of the filamentous fungal diseases include rice blast (*Pyricularia oryzae, Magnaporthe grisea*), rice sheath blight (*Rhizoctonia solani*), rice brown spot (*Cochiobolus miyabeanus*), rice seedling blight (*Rhizopus chinensis, Pythium graminicola, Fusarium graminicola, Fusarium roseum, Mucor* sp., *Phoma* sp., *Tricoderma* sp.), rice bakanae disease (*Gibberella fujikuroi*), powdery mildew of barley, wheat, etc. (*Blumeria graminis, Blumeria graminis hordei*), powdery mildew of cucumbers etc. (*Sphaerotheca fuliginea*), powdery mildew of eggplants etc. (*Erysiphe cichoracoarum*), powdery mildew of other host plants, eyespot of barley, wheat, etc. (*Pseudocercosporella herpotrichoides*), smut of wheat etc. (*Urocystis tritici*), snow mold of barley, wheat, etc. (*Microdochium nivalis, Pythium iwayamai, Typhla ishikariensis, Typhla incarnata, Sclerotinia borealis*), fusarium ear blight of barley, wheat, etc. (*Fusarium graminearum, Fusarium avenaceum, Fusarium culmorum, Microdochium nivalis*), rust of barley, wheat, etc. (*Puccinia recondita, Puccinia striiformis, Puccinia graminis*), take-all of barley, wheat, etc. (*Gaeumannomyces graminis*), oat crown rust (*Puccinia coronata*), rust of other plants, gray mold of cucumbers, strawberries, etc. (*Botrytis cinerea*), sclerotinia rot of tomatoes, cabbages, etc. (*Sclerotinia sclerotiorum*), late blight of potatoes, tomatoes, etc. (*Phytophthora infestans*), late blight of other plants, cucumber downy mildew (*Pseudoperonospora cubensis*), grape downy mildew (*Plasmopara viticola*), downy mildew of various plants, apple scab (*Venturia inaequalis*), apple alternaria blotch (*Alternaria mali*), pear black spot (*Alternaria kikuchiana*), citrus melanose (*Diaporthe citri*), citrus scab (*Elsinoe fawcetti*), sugarbeet leaf spot (*Cercospora beticola*), peanut brown leaf spot (*Cercospora arachidicola*), peanut late leaf spot (*Cercospora personata*), leaf blotch of wheat (*Septoria tritici*), wheat glume blotch (*Leptosphaeria nodorum*), barley net blotch (*Pyrenophora teres*), barley stripe (*Pyrenophora graminea*), barley scald (*Rhynchosporium secalis*), wheat loose smut (*Ustilago nuda*), wheat stinking smut (*Tilletia caries*), brown patch of turfgrass (*Rhizoctonia solani*) and dollar spot of turfgrass (*Sclerotinia homoeocarpa*).

Specific examples of the bacterial diseases include diseases caused by *Pseudomonas* spp. such as cucumber bacterial spot (*Pseudomonas syringae* pv. *Lachrymans*), tomato bacterial wilt disease (*Pseudomonas syringae* pv. *Lachrymans*) and bacterial grain rot of rice (*Pseudomonas glumae*); diseases caused by *Xanthomonas* spp. such as cabbage black rot (*Xanthomonas campestris*), rice bacterial leaf blight (*Xanthomonas oryzae*) and citrus canker (*Xanthomonas citri*); and diseases caused by *Erwinia* spp. such as cabbage soft rot (*Erwinia carotovora*).

Specific examples of the viral diseases include tobacco mosaic disease (tobacco mosaic virus).

In particular, the agricultural and horticultural microbicide comprising the amide compound represented by the general formula [I] of the present invention or a salt thereof as an active ingredient is highly effective against filamentous fungal diseases, particularly, powdery mildew of barley, wheat, etc. (*Blumeria graminis*), powdery mildew of cucumbers etc. (*Sphaerotheca fuliginea*), powdery mildew of eggplants etc. (*Erysiphe cichoracoarum*) and powdery mildew of other host plants and is preferably used against these diseases.

The agricultural and horticultural microbicide comprising the amide compound represented by the general formula [I] of the present invention or a salt thereof as an active ingredient can be used as an insecticide as well as a microbicide. The agricultural and horticultural microbicide can be used alone, or in combination with or as a mixture with other agrochemicals to control pests which may damage paddy rice, fruit trees, vegetables, other crops, and ornamental flowering plants, including agricultural and forest pests, horticultural pests, stored grain pests, sanitary pests, nematodes, etc. Specific examples of the pests, nematodes, etc. include the following: the species of the order Lepidoptera such as *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis,*

*Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura, Eucosma aporema, Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana,*

*Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina* sp., *Carposina niponensis, Conogethes punctiferalis, Synanthedon* sp., *Lyonetia clerkella, Papilio helenus, Colias erate poliographus, Phalera flavescens,* the species of the family Pieridae such as *Pieris brassicae* and *Pieris rapae crucivora, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis;* the species of the order Hemiptera such as *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum,*

*Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda,*

*Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatella, Eurydema pulchrum, Cletus trigonus, Clovia punctata, Empoasca* sp., *Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli,*

*Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii;* the species of the order Coleoptera such as *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata,*

*Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis;* the species of the order Diptera such as *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans*, the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella;* the species of the order Hymenoptera such as *Pristomyrmex pungens*, the species of the family Bethylidae, *Monomorium pharaonis, Pheidole noda, Athalia rosae, Dryocosmus kuriphilus, Formica fusca japonica, Vespinae* spp. (wasps), *Athalia infumata infumata, Arge pagana, Athalia japonica, Acromyrmex* spp., *Solenopsis* spp., *Arge mali* and *Ochetellus glaber;* the species of the order Orthoptera such as *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma;* the species of the order Thysanoptera such as *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Frankliniella occidentalis, Thrips palmi, Frankliniella lilivora* and *Liothrips vaneeckei;* the species of the order Acari such as *Tetranychus truncatus, Tetranychus viennensis, Tetranychus kanzawai, Acaphylla theavagrans, Polyphagotarsonemus latus, Aculops lycopersici, Tetranychus urticae, Eriophyes chibaensis, Brevipalpus* spp., *Tyrophagus similis, Panonychus citri, Brevipalpus phoenicis, Phyllocoptruta citri, Aculus schlechtendali, Panonychus ulmi, Rhyzoglyphus robini* and *Sancassania* spp.;

the species of the order Isoptera such as *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus;* the species of the order Blattodea such as *Periplaneta fuliginosa, Blattella germanica, Blatta orientalis, Periplaneta brunnea, Blattella lituricollis, Periplaneta japonica* and *Periplaneta americana;* the species of the phylum Nematoda such as *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans;* and the species of the phylum Mollusca such as *Pomacea canaliculata, Achatina fulica, Meghimatium bilineatum, Lehmannina valentiana, Limax flavus* and *Acusta despecta sieboldiana.*

In addition, the agricultural and horticultural microbicide of the present invention has a strong insecticidal effect on *Tuta absoluta* as well.

The agricultural and horticultural microbicide comprising the amide compound represented by the general formula [I] of the present invention or a salt thereof as an active ingredient has a remarkable control effect on the above-described diseases which damage lowland crops, field crops, fruit trees, vegetables, other crops, ornamental flowering plants, etc. The desired effect can be obtained when the agricultural and horticultural microbicide is applied to nursery facilities for seedlings, paddy fields, fields, fruit trees, vegetables, other crops, ornamental flowering plants, etc. and their seeds, paddy water, foliage, cultivation media such as soil, or the like around the expected time of disease infestation, i.e., before the infestation or upon the confirmation of the infestation. In addition, the application of the agricultural and horticultural microbicide utilizes so-called penetration and translocation. That is, nursery soil, soil in transplanting holes, plant foot, irrigation water, cultivation water in hydroponics, or the like is treated with the agricultural and horticultural microbicide to allow crops, ornamental flowering plants, etc. to absorb the compound of the present invention through the roots via soil or otherwise.

The useful plants to which the agricultural and horticultural microbicide of the present invention can be applied include, but are not particularly limited to, for example, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., chrysanthemum, rose, carnation, orchid, tulip, lily, etc.), garden trees (e.g., ginkgo trees, cherry trees, Japanese aucuba, etc.) and forest trees (e.g., *Abies sachalinensis, Picea jezoensis*, pine, yellow cedar, Japanese cedar, hinoki cypress, eucalyptus, etc.). Preferably, the useful plant to which the agricultural and horticultural microbicide of the present invention can be applied is cereals.

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural microbicide of the present invention can be applied to these plants as well.

Further, exemplary toxins expressed in genetically modified plants include insecticidal proteins derived from *Bacillus cereus* or *Bacillus popilliae*; *Bacillus thuringiensis*-derived δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode-derived insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: 6-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining domains derived from these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural microbicide of the present invention can be used in combination or used systematically.

In order to control various diseases, the agricultural and horticultural microbicide of the present invention, with or without appropriate dilution or suspension in water etc., is applied to plants potentially infested with diseases in an amount effective for the control of the diseases. For example, in order to control diseases that may infest crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural microbicide of the present invention, with or without appropriate dilution or suspension in water etc., can be applied to sites potentially infested with plant diseases in an amount effective for the control of the diseases. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural microbicide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; application of a dust, a wettable powder, a water-dispersible granule, a granule or the like to planting holes before seeding or planting; and application of a dust, a wettable powder, a water-dispersible granule, a granule or the like to planting rows or the like.

To nursery boxes for paddy rice, for example, a dust, a water-dispersible granule, a granule or the like can be applied, although the suitable formulation may vary depending on the application time, in other words, depending on the cultivation stage such as seeding time, greening period and planting time. A formulation such as a dust, a water-dispersible granule, a granule or the like may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer or the like, may be applied onto soil or injected into soil. In addition, a solution of an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural microbicide of the present invention is commonly used as a formulation convenient for application, which is prepared in the usual method for preparing agrochemical formulations.

That is, the amide compound represented by the general formula [I] of the present invention or a salt thereof and an appropriate carrier, and if needed an adjuvant, are blended in an appropriate ratio, and through the step of dissolution, separation, suspension, mixing, impregnation, adsorption and/or adhesion, can be formulated into an appropriate form for application, such as a suspension concentrate, an emulsifiable concentrate, a soluble concentrate, a wettable powder, a water-dispersible granule, a granule, a dust, a tablet and a pack.

The agricultural and horticultural microbicidal composition of the present invention can optionally contain an additive usually used for agrochemical formulations in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. These additives may be used alone or in a combination of two or more kinds.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic high-dispersion silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). These solid carriers may be used alone or in a combination of two or more kinds.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; straight-chain or cyclic ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide, N-alkyl pyrrolidinone and N-methylpyrrolidone; nitriles, such as acetonitrile; sulfur compounds, such as dimethyl sulfoxide; vegetable oils, such as soybean oil, rapeseed oil, cotton seed oil and castor oil; and water. These liquid carriers may be used alone or in a combination of two or more kinds.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether (e.g., polyoxyethylene nonylphenyl ether), polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. These surfactants may be used alone or in a combination of two or more kinds.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The content of the active ingredient compound in the agricultural and horticultural microbicide of the present invention can be adjusted as needed, and for example, is appropriately selected from the range of 0.01 to 90 parts by weight in 100 parts by weight of the agricultural and horticultural microbicide. For example, in the case where the agricultural and horticultural microbicide is a dust, a granule, an emulsifiable concentrate or a wettable powder, it is suitable that the content of the active ingredient compound is 0.01 to 50 parts by weight (0.01 to 50% by weight relative to the total weight of the agricultural and horticultural microbicide).

The application rate of the agricultural and horticultural microbicide of the present invention may vary with various factors, for example, the purpose, the status of the target disease, the growing conditions of crops, the tendency of disease infestation, the weather, the environmental conditions, the dosage form, the application method, the application site, the application time, etc., but for example, the application amount of the active ingredient compound per 10 ares is appropriately selected from the range of 0.001 g to 10 kg, and preferably 0.01 g to 1 kg depending on the purpose.

Furthermore, for the expansion of the range of target pests and diseases and the appropriate application time for control of pests and diseases, or for dose reduction, the agricultural and horticultural microbicide of the present invention can be used after mixed with other agricultural or horticultural insecticides, acaricides, nematicides, microbicides, biopesticides and/or the like. Further, the agricultural and horticultural microbicide can be used after mixed with herbicides, plant growth regulators, fertilizers and/or the like depending on its application.

Examples of such additional agricultural and horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai, Bacillus thuringiensis israelensis, Bacillus thuringiensis japonensis, Bacillus thuringiensis kurstaki* and *Bacillus thuringiensis tenebrionis*, BPMC (2-(1-methylpropyl)phenyl N-methylcarbamate), Bt toxin-derived insecticidal compounds, chlorfenson (CPCBS), dichlorodiisopropyl ether (DCIP), 1,3-dichloropropene (D-D), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, phenisobromolate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur, nicotine-sulfate, isocycloseram, dimpropyridaz, and flupyrimin.

Examples of the agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-aluminum, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, inorganic microbicides such as basic copper chloride, basic copper sulfate and silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate, copper sulfate pentahydrate, ipflufenoquin, pyridachlometyl, fluoxapiprolin, pronitridine, florylpicoxamid, and metyltetraprole.

Further, examples of the herbicides include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chloethoxyfen, clomeprop, chlorazifop, chlorazine, chloranocryl, chloramben, cloransulam, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, propamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monofamquat, iodosulfuron, iodosulfuron-methyl-sodium, iodobonil, iodomethane, lactofen, linuron, rimsulfuron, lenacil, rhodethanil, calcium peroxide, methyl bromide, cyclopyranil, and tetflupyrolimet.

Examples of the biopesticides include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor*, avirulent *Erwinia carotovora* and *Bacillus subtilis*; and biopesticides used as a herbicide, such as *Xanthomonas campestris*. A combined use of the agricultural and horticultural microbicide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*;

and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples. THF, DMF, DMSO, LDA, MTBE, Teoc, and TBAF stand for tetrahydrofuran, dimethylformamide, dimethyl sulfoxide, lithium diisopropylamide, methyl tert-butyl ether, 2-(trimethylsilyl)ethoxycarbonyl, and tetrabutylammonium fluoride, respectively, and mmol stands for millimole. The values (%) described in the parentheses following the quantities of the products yielded in the Reference Examples and Examples shown below represent yields.

EXAMPLES

Example 1

Production of Compound Numbers 1-23 (A7 in the Reaction Scheme Shown Below) and 1-25 (A8 in the Same Reaction Scheme)

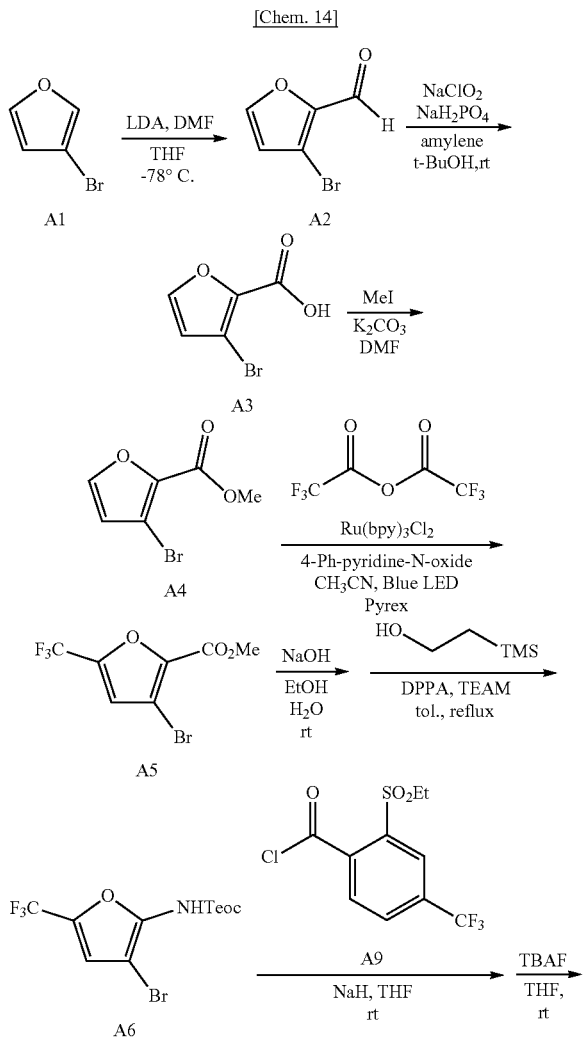

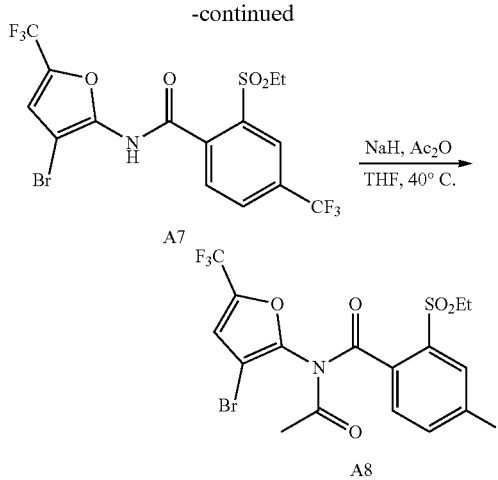

Reference Example 1-1

Production of methyl 3-bromofuran-2-carboxylate (A4)

Anhydrous THF (50 mL) and 3-bromofuran (A1) (5.0 g, 34.0 mmol) were added to a 300-mL three-necked flask under an argon atmosphere, and the mixture was cooled to −78° C. with stirring. To this, a solution of LDA (1 M in THF/hexane) (51 mL, 51.0 mmol) was slowly added dropwise at −78° C., and the mixture was stirred at −78° C. for 30 minutes. Subsequently, anhydrous DMF (3.7 g, 51.0 mmol) was slowly added dropwise at −78° C., and the mixture was stirred at −78° C. for 10 minutes. After the completion of the reaction, 1 N hydrochloric acid was slowly added dropwise, and ethyl acetate extraction was performed. The organic layer was washed with a saturated aqueous sodium chloride solution, dried over anhydrous sodium sulfate, and filtered. The solvent in the filtrate was evaporated off in vacuo to give 5.5 g of a crude product of 3-bromo-2-furyl aldehyde (A2).

5.5 g of the crude product of A2 obtained in the previous step, NaH$_2$PO$_4$ (12.2 g, 102 mmol), and amylene (11.9 g, 170 mmol) were dissolved in tert-butanol (200 mL). To this, an aqueous solution (20 mL) of NaClO$_2$ (9.1 g, 102 mmol, 80% purity) was slowly added dropwise under ice cooling, and the mixture was stirred at room temperature for 3 hours. After the completion of the reaction, the reaction mixture was basified with a 1 N aqueous sodium hydroxide solution and washed with MTBE. This was rendered acidic again with 1 N hydrochloric acid, and ethyl acetate extraction was performed. The organic layer was washed with a saturated aqueous sodium chloride solution, dried over anhydrous sodium sulfate, and filtered. The solvent in the filtrate was evaporated off in vacuo to give 6.5 g of a crude product of 3-bromo-2-furancarboxylic acid (A3).

6.5 g of the crude product of A3 obtained in the previous step, potassium carbonate (7.0 g, 51.0 mmol), and methyl iodide (7.2 g, 51.0 mmol) were dissolved in DMF (100 mL), and the mixture was stirred at room temperature for 5 hours. After the completion of the reaction, water was added, and ethyl acetate extraction was performed. The organic layer was washed successively with dilute hydrochloric acid and a saturated aqueous sodium chloride solution, dried over anhydrous sodium sulfate, and filtered. The solvent in the filtrate was evaporated off in vacuo. The residue was subjected to silica gel column chromatography to give 3.3 g (49%, (3 steps)) of methyl 3-bromofuran-2-carboxylate (A4).

Reference Example 1-2

Production of methyl 3-bromo-5-trifluoromethyl-2-furancarboxylate (A5)

A4 (0.60 g, 2.9 mmol), tris(2,2'-bipyridyl)ruthenium(II) dichloride (Ru(bpy)$_3$Cl$_2$) hexahydrate (21 mg, 0.029 mmol), and 4-phenylpyridine-N-oxide (1.0 g, 5.9 mmol) were added to a 50-mL three-necked flask manufactured by Pyrex (registered trademark). To this, anhydrous acetonitrile (8 mL) was added under an argon atmosphere. Subsequently, trifluoroacetic anhydride (1.35 g, 6.45 mmol) was slowly added, and the mixture was subjected to photoirradiation using a blue LED lamp (Twin LED Light, manufactured by RelyOn Ltd., 425 nm, 2W×2) for 6 hours. After the completion of the reaction, the solvent was evaporated off in vacuo. The residue was subjected to silica gel column chromatography to give 0.27 g (34%) of methyl 3-bromo-5-trifluoromethyl-2-furancarboxylate (A5).

Reference Example 1-3

Production of 3-bromo-5-trifluoromethyl-2-{2-(trimethylsilyl) ethoxycarbonylamino}furan (A6)

A5 (0.27 g, 1.0 mmol) and sodium hydroxide (60 mg, 1.5 mmol) were dissolved in ethanol (10 mL) and water (2 mL), and the mixture was stirred at room temperature for 5 hours. After the completion of the reaction, water was added, and the mixture was washed with MTBE. This was rendered acidic again with 1 N hydrochloric acid, and ethyl acetate extraction was performed. The organic layer was washed with a saturated aqueous sodium chloride solution, dried over anhydrous sodium sulfate, and filtered. The solvent in the filtrate was evaporated off in vacuo.

The crude product obtained in the previous step, DPPA (diphenylphosphoryl azide: 0.33 g, 1.2 mmol), triethylamine (0.12 g, 1.2 mmol), and 2-(trimethylsilyl)ethanol (0.47 g, 4.0 mmol) were dissolved in toluene (20 mL), and the mixture was heated under reflux for 6 hours. After the completion of the reaction, the solvent was evaporated off in vacuo. The residue was subjected to silica gel column chromatography to give 0.20 g (56% (2 steps)) of 3-bromo-5-trifluoromethyl-2-{2-(trimethylsilyl) ethoxycarbonylamino} furan (A6).

Example 1-4

Production of N-[3-bromo-5-(trifluoromethyl)furan-2-yl]-2-(ethylsulfonyl)-4-(trifluoromethyl)benzamide (A7, Compound Number 1-23)

A6 (0.20 g, 0.53 mmol) was dissolved in anhydrous THF (5 mL), and sodium hydride (34 mg, 0.84 mmol) was slowly added. The mixture was stirred at room temperature for 30 minutes. To this, a toluene solution of A9 (0.67 mmol), which was prepared separately, was added, and the mixture was stirred at room temperature for 5 hours. After the completion of the reaction, water was added, and ethyl acetate extraction was performed. The organic layer was washed with a saturated aqueous sodium chloride solution, dried over anhydrous sodium sulfate, and filtered. The solvent in the filtrate was evaporated off in vacuo.

The crude product (A6) obtained in the previous step was dissolved in THF (10 mL), and a THF solution of TBAF (1 M, 3 mL) was slowly added. The mixture was stirred at room temperature for 10 minutes. After the completion of the reaction, the solvent was evaporated off in vacuo. The residue was subjected to silica gel column chromatography to give 0.22 g (66%, (2 steps)) of N-[3-bromo-5-(trifluoromethyl)furan-2-yl]-2-(ethylsulfonyl)-4-(trifluoromethyl)benzamide (A7).
Melting point: 160 to 162° C.

Example 1-5

Production of N-acetyl-N-[3-bromo-5-(trifluoromethyl)furan-2-yl]-2-(ethylsulfonyl)-4-(trifluoromethyl)benzamide (A8, Compound Number 1-25)

A7 (0.20 g, 0.41 mmol) was dissolved in anhydrous THF (3 mL), and 60% sodium hydride (0.062 g, 0.61 mmol) was added. The mixture was heated at 40° C. with stirring for 10 minutes. To this, acetic anhydride (0.060 g, 0.61 mmol) was added, and the mixture was stirred at 40° C. for 1 hour. After the completion of the reaction, the reaction mixture was slowly added to 10 mL of 1 N hydrochloric acid, and ethyl acetate extraction was performed. The organic layer was washed with a saturated aqueous sodium chloride solution. The organic layer was dried over anhydrous sodium sulfate, and the solvent was evaporated off. The residue was subjected to silica gel column chromatography to give 0.20 g (91%) of N-acetyl-N-[3-bromo-5-(trifluoromethyl)furan-2-yl]-2-(ethylsulfonyl)-4-(trifluoromethyl)benzamide (A8).

Example 2

Production of Compound Numbers 2-29 (B3 in the Reaction Scheme Shown Below), 2-30 (B4 in the Same Reaction Scheme), and 2-32 (B5 in the Same Reaction Scheme)

[Chem. 15]

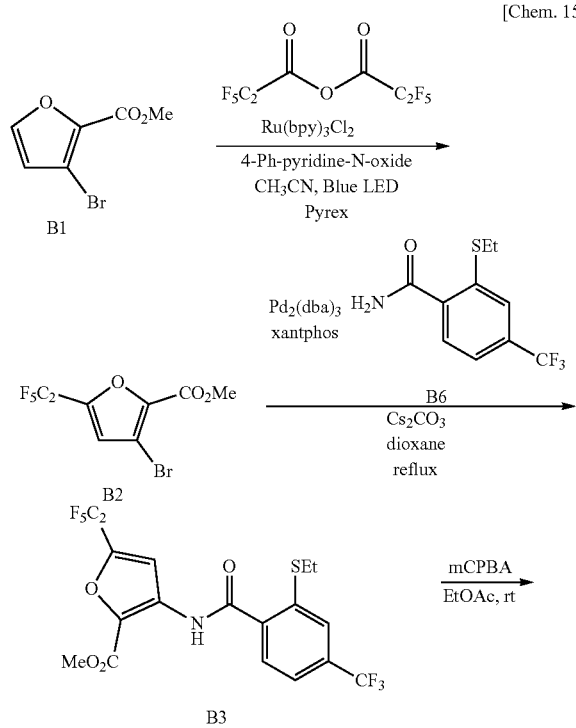

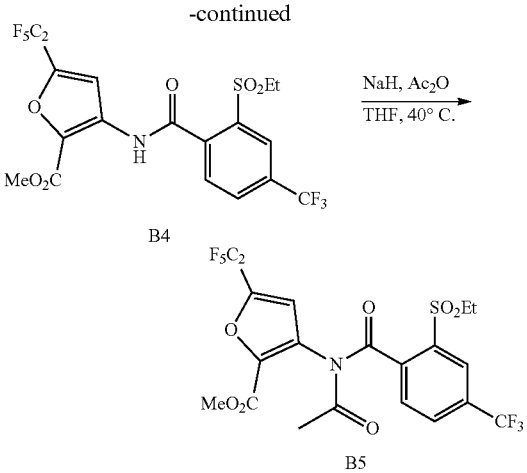

Reference Example 2-1

Production of methyl 3-bromo-5-pentafluoroethyl-2-furancarboxylate (B2)

Methyl 3-bromofuran-2-carboxylate (B1) (0.30 g, 1.46 mmol), tris(2,2'-bipyridyl)ruthenium(II) dichloride (Ru(bpy)$_3$Cl$_2$) hexahydrate (55 mg, 0.073 mmol), and 4-phenylpyridine-N-oxide (1.0 g, 5.8 mmol) were added to a 50-mL three-necked flask manufactured by Pyrex (registered trademark). To this, anhydrous acetonitrile (8 mL) was added under an argon atmosphere. Subsequently, pentafluoropropionic anhydride (1.81 g, 5.84 mmol) was slowly added, and the mixture was subjected to photoirradiation using a blue LED lamp (Twin LED Light, manufactured by RelyOn Ltd., 425 nm, 2W×2) for 6 hours. After the completion of the reaction, the solvent was evaporated off in vacuo. The residue was subjected to silica gel column chromatography to give 0.23 g (50%) of methyl 3-bromo-5-pentafluoroethyl-2-furancarboxylate (B2).

Example 2-2

Production of N-[2-methoxycarbonyl-5-(pentafluoroethyl)furan-3-yl]-2-(ethylthio)-4-(trifluoromethyl)benzamide (B3, Compound Number 2-29)

B2 (0.23 g, 0.72 mmol) and 2-ethylthio-4-trifluoromethyl benzamide (B6) (0.25 g, 0.88 mmol) were dissolved in 1,4-dioxane (20 mL). To this, Xantphos (0.17 g, 0.29 mmol), cesium carbonate (0.47 g, 1.4 mmol), and tris(dibenzylideneacetone)palladium(0) (0.066 g, 0.072 mmol) were successively added, and the mixture was heated at 100° C. with stirring under an argon atmosphere for 7 hours. The reaction mixture was allowed to come to room temperature and then filtered through Celite. The solvent in the filtrate was evaporated off in vacuo. The residue was subjected to silica gel column chromatography to give 0.26 g (74%) of N-[2-methoxycarbonyl-5-(pentafluoroethyl)furan-3-yl]-2-(ethylthio)-4-(trifluoromethyl)benzamide (B3).

Example 2-3

Production of N-[2-methoxycarbonyl-5-(pentafluoroethyl)furan-3-yl]-2-(ethylsulfonyl)-4-(trifluoromethyl)benzamide (B4, Compound Number 2-30)

B3 (0.26 g, 0.53 mmol) was dissolved in ethyl acetate (10 mL), and 65% m-chloroperoxybenzoic acid (0.23 g, 1.32 mmol) was slowly added. The mixture was stirred at room temperature for 7 hours, and a saturated aqueous sodium thiosulfate solution was added. This was diluted with ethyl acetate and washed successively with a saturated aqueous sodium hydrogen carbonate solution and a saturated aqueous sodium chloride solution. The organic layer was dried over anhydrous sodium sulfate, and the solvent was evaporated off in vacuo. The residue was subjected to silica gel column chromatography to give 0.15 g (54%) of N-[2-methoxycarbonyl-5-(pentafluoroethyl)furan-3-yl]-2-(ethylsulfonyl)-4-(trifluoromethyl)benzamide (B4).

Production of N-acetyl-N-[2-methoxycarbonyl-5-(pentafluoroethyl)furan-3-yl]-2-(ethylsulfonyl)-4-(trifluoromethyl)benzamide (B5, Compound Number 2-32)

The same procedure as described above for the production of A8 was performed using B4 (0.20 g, 0.37 mmol) to give 0.37 g (75%) of N-acetyl-N-[2-methoxycarbonyl-5-(pentafluoroethyl)furan-3-yl]-2-(ethylsulfonyl)-4-(trifluoromethyl)benzamide (B5).

Example 3

Production of Compound Numbers 2-9 (C3 in the Reaction Scheme Shown Below), 2-10 (C4 in the Same Reaction Scheme), and 2-12 (C5 in the Same Reaction Scheme)

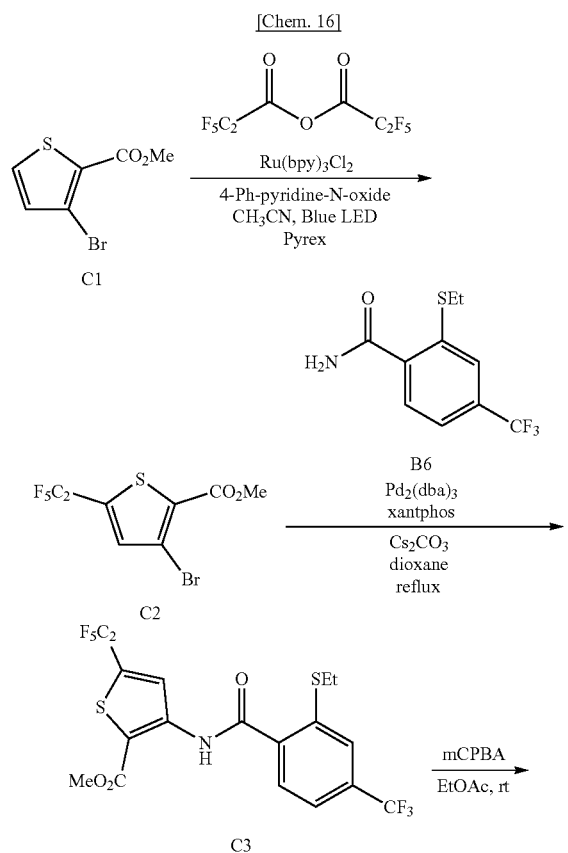

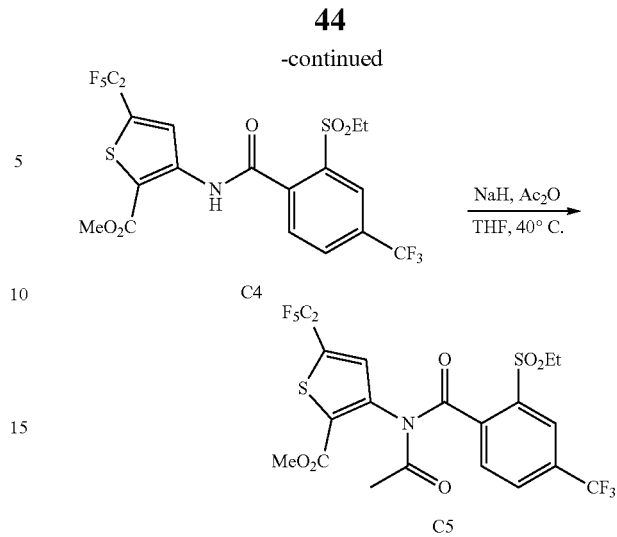

Example 3

Methyl 3-bromothiophene-2-carboxylate (CAS RN (CAS registered trademark): 26137-08-6) is commercially available. The amide compound can be produced by the same reaction as described in Example 2. The same procedure as described in Example 2 was performed to give N-[2-methoxycarbonyl-5-(pentafluoroethyl)thiophen-3-yl]-2-(ethylthio)-4-(trifluoromethyl)benzamide (C3, compound number 2-9), N-[2-methoxycarbonyl-5-(pentafluoroethyl)thiophen-3-yl]-2-(ethylsulfonyl)-4-(trifluoromethyl)benzamide (C4, compound number 2-10), and N-acetyl-N-[2-methoxycarbonyl-5-(pentafluoroethyl)thiophen-3-yl]-2-(ethylsulfonyl)-4-(trifluoromethyl)benzamide (C5, compound number 2-12).

Example 4

Production of Compound Numbers 2-6 (D5 in the Reaction Scheme Shown Below) and 2-8 (D6 in the Same Reaction Scheme)

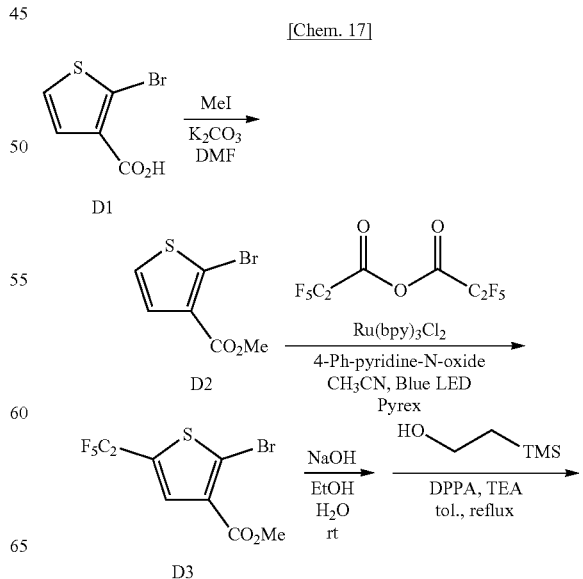

-continued

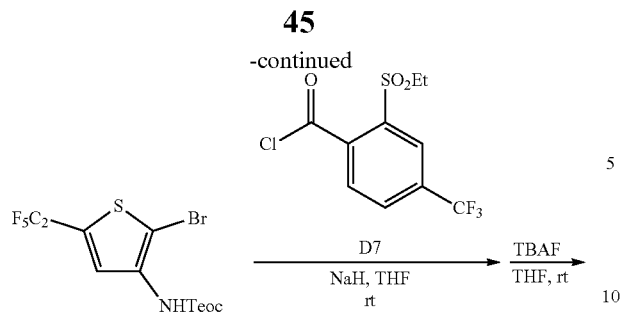

Example 4-1

The same procedure as described in Example 1 was performed using 2-bromo-3-thiophene carboxylic acid as a starting material to give N-[2-bromo-5-(pentafluoroethyl)thiophen-3-yl]-2-(ethylsulfonyl)-4-(trifluoromethyl)benzamide (D5, compound number 2-6) and N-acetyl-N-[2-bromo-5-(pentafluoroethyl)thiophen-3-yl]-2-(ethylsulfonyl)-4-(trifluoromethyl)benzamide (D6, compound number 2-8).

Example 5

Production of Compound Numbers 2-14 (E1) and 2-16 (E2)

[Chem. 18]

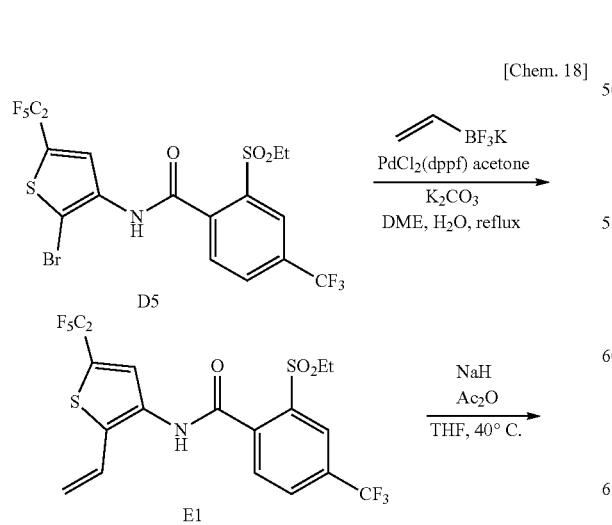

-continued

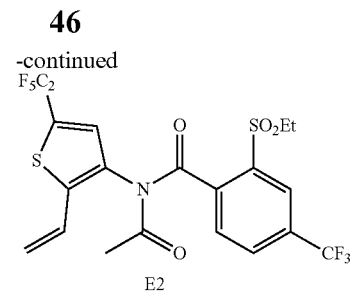

Example 5-1

Production of N-[2-vinyl-5-(pentafluoroethyl)thiophen-3-yl]-2-(ethylsulfonyl)-4-(trifluoromethyl)benzamide (E1, Compound Number 2-14)

D5 (0.12 g, 0.21 mmol), potassium vinyltrifluoroborate (44 mg, 0.26 g), potassium carbonate (58 mg, 0.42 mmol), and a [1,1'-bis(diphenylphosphino)ferrocene]palladium(II) dichloride acetone adduct (16 mg, 0.021 mmol) were dissolved in a mixture of dimethoxyethane (5 mL) and water (1 mL). The mixture was heated under reflux under an argon atmosphere for 7 hours. The reaction mixture was allowed to come to room temperature and then filtered through Celite. The solvent in the filtrate was evaporated off in vacuo. The residue was subjected to silica gel column chromatography to give 0.10 g (72%) of N-[2-vinyl-5-(pentafluoroethyl)thiophen-3-yl]-2-(ethylsulfonyl)-4-(trifluoromethyl)benzamide (E1).

Example 5-2

Production of N-acetyl-N-[2-vinyl-5-(pentafluoroethyl)thiophen-3-yl]-2-(ethylsulfonyl)-4-(trifluoromethyl)benzamide (E2, Compound Number 2-16)

The same procedure as described for the production of A8 in Example 1 was performed to give N-acetyl-N-[2-vinyl-5-(pentafluoroethyl)thiophen-3-yl]-2-(ethylsulfonyl)-4-(trifluoromethyl)benzamide (E2).

Example 6

Production of Compound Numbers 2-18 (F1 in the Reaction Scheme Shown Below) and 2-20 (F2 in the Same Reaction Scheme)

[Chem. 19]

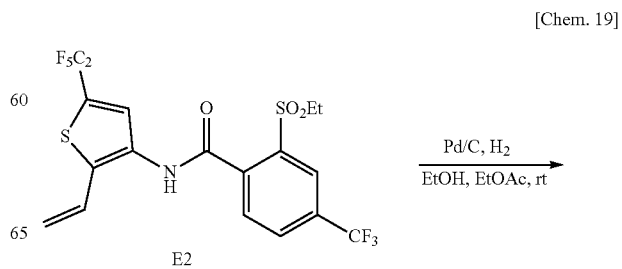

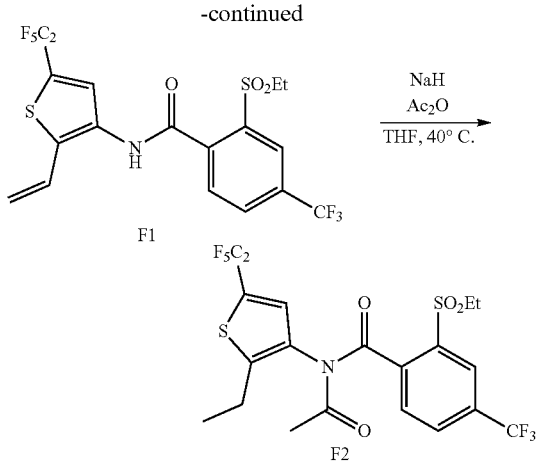

Example 6-1

Production of N-[2-ethyl-5-(pentafluoroethyl)thiophen-3-yl]-2-(ethylsulfonyl)-4-(trifluoromethyl)benzamide (F1, Compound Number 2-18)

E2 (0.10 g, 0.20 mmol) and 10% palladium carbon (10 mg) were dissolved in ethanol (10 mL) and ethyl acetate (5 mL), and the mixture was stirred under 3 atm hydrogen pressure for 18 hours. The reaction mixture was allowed to come to room temperature and then filtered through Celite. The solvent in the filtrate was evaporated off in vacuo. The residue was subjected to silica gel column chromatography to give 90 mg (88%) of N-[2-ethyl-5-(pentafluoroethyl) thiophen-3-yl]-2-(ethylsulfonyl)-4-(trifluoromethyl)benzamide (F1).

Example 6-2

Production of N-acetyl-N-[2-ethyl-5-(pentafluoroethyl)thiophen-3-yl]-2-(ethylsulfonyl)-4-(trifluoromethyl)benzamide (F2, Compound Number 2-20)

The same procedure as described for the production of A8 in Example 1 was performed to give N-acetyl-N-[2-ethyl-5-(pentafluoroethyl)thiophen-3-yl]-2-(ethylsulfonyl)-4-(trifluoromethyl)benzamide (F2).

Example 7

Production of Compound Numbers 2-38 (G5 in the Reaction Scheme Shown Below) and 2-40 (G6 in the Same Reaction Scheme)

[Chem. 20]

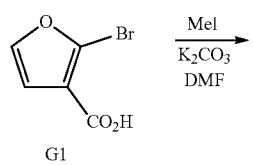

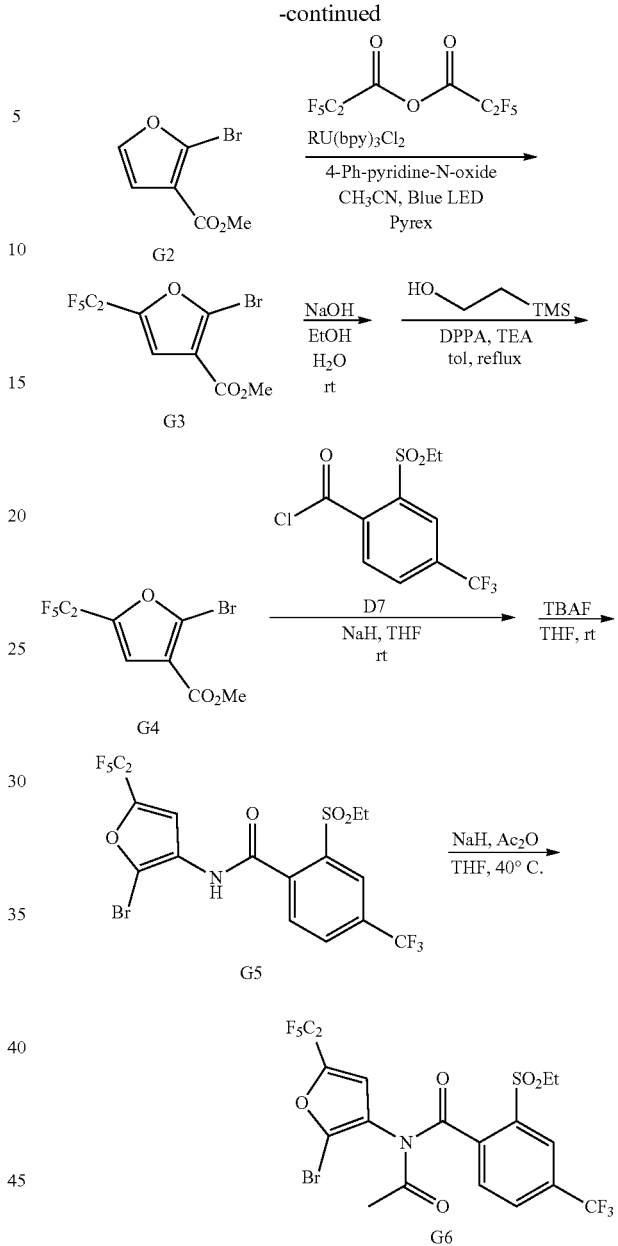

Example 7-1

Production of N-[2-bromo-5-(pentafluoroethyl) furan-3-yl]-2-(ethylsulfonyl)-4-(trifluoromethyl) benzamide (G5, Compound Number 2-38) and N-acetyl-N-[2-bromo-5-(pentafluoroethyl)furan-3-yl]-2-(ethylsulfonyl)-4-(trifluoromethyl)benzamide (G6, Compound 2-40)

The same procedure as described in Example 1 was performed to give N-[2-bromo-5-(pentafluoroethyl)furan-3-yl]-2-(ethylsulfonyl)-4-(trifluoromethyl)benzamide (G5, compound number 2-38) and N-acetyl-N-[2-bromo-5-(pentafluoroethyl)furan-3-yl]-2-(ethylsulfonyl)-4-(trifluoromethyl)benzamide (G6, compound 2-40)

Example 8

Production of Compound Number 2-42 (I2 in the Reaction Scheme Shown Below)

[Chem. 21]

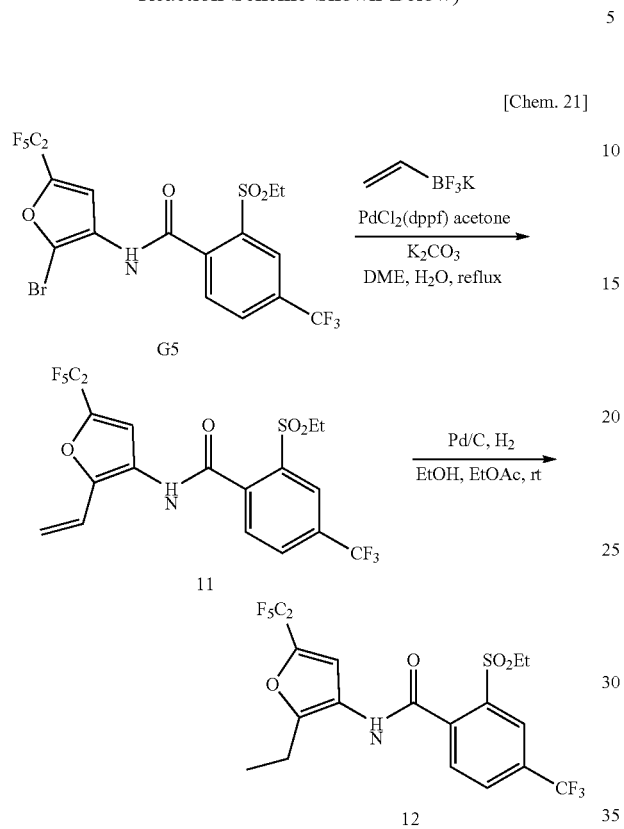

Example 8-1

Production of N-[2-ethyl-5-(pentafluoroethyl)furan-3-yl]-2-(ethylsulfonyl)-4-(trifluoromethyl)benzamide (I2, Compound Number 2-42)

The same procedure as described in Example 6 was performed to give N-[2-ethyl-5-(pentafluoroethyl)furan-3-yl]-2-(ethylsulfonyl)-4-(trifluoromethyl)benzamide (I2, compound number 2-42)

Example 9

Production of Compound Numbers 2-45 (J3 in the Reaction Scheme Shown Below), 2-46 (J4 in the Same Reaction Scheme), and 2-48 (J5 in the Same Reaction Scheme)

[Chem. 22]

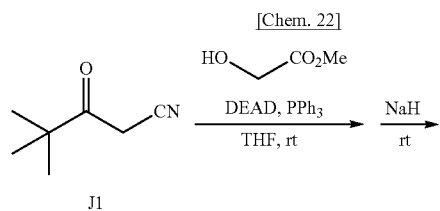

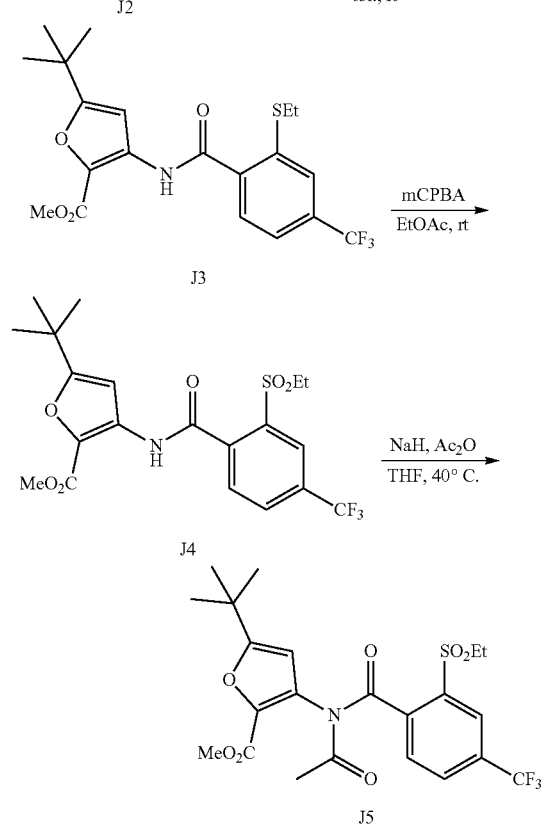

Example 9-1

Production of 3-amino-5-tert-butylfuran-2-carboxylic Acid Methyl Ester (J2)

The same synthesis procedure as described in literature (Organic Letters, 2000, Vol. 2, No. 14, 2061-2063.) was performed using pivaloyl acetonitrile (J) (1.0 g, 8.0 mmol) to give 0.59 g (yield: 44) of 3-amino-5-tert-butylfuran-2-carboxylic acid methyl ester (J2)

Example 9-2

Production of N-[2-methoxycarbonyl-5-(tert-butyl) furan-3-yl]-2-(ethylthio)-4-(trifluoromethyl)benzamide (J3, Compound Number 2-45)

The same synthesis procedure as described in literature (WO 2016/182021) was performed using J2 (0.59 g, 3.0 mmol) to give 0.36 g (yield: 280) of N-[2-methoxycarbonyl-5-(tert-butyl)furan-3-yl]-2-(ethylthio)-4-(trifluoromethyl) benzamide (J3, compound number 2-45).

Example 9-3

Production of N-[2-methoxycarbonyl-5-(tert-butyl)furan-3-yl]-2-(ethylsulfonyl)-4-(trifluoromethyl)benzamide (J4, Compound Number 2-46)

The same procedure as described above for the synthesis of B4 in Example 2 was performed using J3 (0.30 g, 0.70 mmol) as a starting material to give 0.25 g (yield: 78%) of N-[2-methoxycarbonyl-5-(tert-butyl)furan-3-yl]-2-(ethylsulfonyl)-4-(trifluoromethyl)benzamide (J4).

Example 9-4

Production of N-acetyl-N-[2-methoxycarbonyl-5-(tert-butyl)furan-3-yl]-2-(ethylsulfonyl)-4-(trifluoromethyl)benzamide (J5, Compound Number 2-48)

The same procedure as described above for the synthesis of A8 in Example 1 was performed using J4 (0.20 g, 0.43 mmol) as a starting material to give 0.15 g (yield: 69%) of N-acetyl-N-[2-methoxycarbonyl-5-(tert-butyl)furan-3-yl]-2-(ethylsulfonyl)-4-(trifluoromethyl)benzamide (J5).

Specific examples of the compound of the present invention are shown below. In the following tables (Tables 1-1, 2-1 to 2-3, 3-1, 4-1 to 4-5, and 5-1 to 5-3), H stands for a hydrogen atom, Me stands for a methyl group, Et stands for an ethyl group, n-Pr stands for a n-propyl group, i-Pr stands for an isopropyl group, cy-Pr stands for a cyclopropyl group, i-Bu stands for an isobutyl group, n-Bu stands for a n-butyl group, sec-Bu stands for a sec-butyl group, tert-Bu or t-Bu stands for a tert-butyl group, Pen stands for a pentyl group, Hex stands for a hexyl group, Ac stands for an acetyl group, Propargyl stands for a propargyl group, Hep stands for a heptyl group, Bn stands for a benzyl group, Thiophene stands for a thiophene group, and Allyl stands for an allyl group. TMS stands for a trimethylsilyl group. Shown in the column of "Physical property value" is a melting point (° C.), a refractive index $n_D$ (measurement temperature; ° C.), or "NMR". NMR data are shown in appended tables 1 to 3 (Tables 6 to 8).

Specific examples of the compound represented by the following general formula [I-4] are shown in the following table.

[Chem. 23]

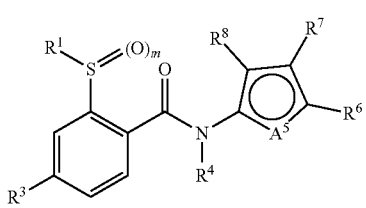

[I-4]

In the formula [I-4] above, $R^3$ represents $CF_3$ and $R^1$ represents Et.

TABLE 1-1

| Compound No. | $R^4$ | $A^5$ | $R^6$ | $R^7$ | $R^8$ | m | Physical property value |
|---|---|---|---|---|---|---|---|
| 1-1 | H | S | $CF_3$ | H | OEt | 0 | |
| 1-2 | H | S | $CF_3$ | H | OEt | 2 | 202-203 |

TABLE 1-1-continued

| Compound No. | $R^4$ | $A^5$ | $R^6$ | $R^7$ | $R^8$ | m | Physical property value |
|---|---|---|---|---|---|---|---|
| 1-3 | Ac | S | $CF_3$ | H | OEt | 0 | |
| 1-4 | Ac | S | $CF_3$ | H | OEt | 2 | 130-131 |
| 1-5 | H | S | $CF_3$ | H | On-Pr | 0 | 92-93 |
| 1-6 | H | S | $CF_3$ | H | On-Pr | 2 | 218-220 |
| 1-7 | Ac | S | $CF_3$ | H | On-Pr | 0 | |
| 1-8 | Ac | S | $CF_3$ | H | On-Pr | 2 | 1.4915 (27.8) |
| 1-9 | H | S | $CF_3$ | H | Oi-Pr | 0 | 89-90 |
| 1-10 | H | S | $CF_3$ | H | Oi-Pr | 2 | 215-217 |
| 1-11 | Ac | S | $CF_3$ | H | Oi-Pr | 0 | |
| 1-12 | Ac | S | $CF_3$ | H | Oi-Pr | 2 | 1.487 (25.8) |
| 1-13 | H | S | $CF_3$ | H | $CO_2Me$ | 0 | |
| 1-14 | H | S | $CF_3$ | H | $CO_2Me$ | 2 | 182-183 |
| 1-15 | Ac | S | $CF_3$ | H | $CO_2Me$ | 0 | |
| 1-16 | Ac | S | $CF_3$ | H | $CO_2Me$ | 2 | NMR |
| 1-17 | H | S | $i-C_3F_7$ | H | $CO_2Me$ | 0 | 137-138 |
| 1-18 | H | S | $i-C_3F_7$ | H | $CO_2Me$ | 2 | |
| 1-19 | Ac | S | $i-C_3F_7$ | H | $CO_2Me$ | 0 | |
| 1-20 | Ac | S | $i-C_3F_7$ | H | $CO_2Me$ | 2 | |
| 1-21 | $CO_2CH_2CH_2TMS$ | S | $CF_3$ | H | Oi-Pr | 0 | 1.494 (25.9) |
| 1-22 | H | O | $CF_3$ | H | Br | 0 | |
| 1-23 | H | O | $CF_3$ | H | Br | 2 | 160-162 |
| 1-24 | Ac | O | $CF_3$ | H | Br | 0 | |
| 1-25 | Ac | O | $CF_3$ | H | Br | 2 | NMR |

Specific examples of the compound represented by the following general formula [I-5] are shown in the following table.

[Chem. 24]

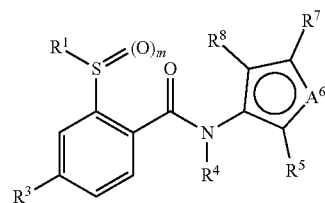

[I-5]

In the formula [I-5] above, $R^3$ represents $CF_3$ and $R^1$ represents Et.

TABLE 2-1

| Compound No. | $R^4$ | $R^5$ | $A^6$ | $R^7$ | $R^8$ | m | Physical property value |
|---|---|---|---|---|---|---|---|
| 2-1 | H | $CO_2Me$ | S | $CF_3$ | H | 0 | |
| 2-2 | H | $CO_2Me$ | S | $CF_3$ | H | 2 | 171-173 |
| 2-3 | Ac | $CO_2Me$ | S | $CF_3$ | H | 0 | |
| 2-4 | Ac | $CO_2Me$ | S | $CF_3$ | H | 2 | |
| 2-5 | H | Br | S | $CF_2CF_3$ | H | 0 | |
| 2-6 | H | Br | S | $CF_2CF_3$ | H | 2 | 148-150 |
| 2-7 | Ac | Br | S | $CF_2CF_3$ | H | 0 | |
| 2-8 | Ac | Br | S | $CF_2CF_3$ | H | 2 | NMR |
| 2-9 | H | $CO_2Me$ | S | $CF_2CF_3$ | H | 0 | |
| 2-10 | H | $CO_2Me$ | S | $CF_2CF_3$ | H | 2 | 164-166 |
| 2-11 | Ac | $CO_2Me$ | S | $CF_2CF_3$ | H | 0 | |
| 2-12 | Ac | $CO_2Me$ | S | $CF_2CF_3$ | H | 2 | NMR |
| 2-13 | H | vinyl | S | $CF_2CF_3$ | H | 0 | |
| 2-14 | H | vinyl | S | $CF_2CF_3$ | H | 2 | 169-170 |
| 2-15 | Ac | vinyl | S | $CF_2CF_3$ | H | 0 | |
| 2-16 | Ac | vinyl | S | $CF_2CF_3$ | H | 2 | |
| 2-17 | H | Et | S | $CF_2CF_3$ | H | 0 | |
| 2-18 | H | Et | S | $CF_2CF_3$ | H | 2 | 163-165 |

TABLE 2-1-continued

| Compound No. | $R^4$ | $R^5$ | $A^6$ | $R^7$ | $R^8$ | m | Physical property value |
|---|---|---|---|---|---|---|---|
| 2-19 | Ac | Et | S | $CF_2CF_3$ | H | 0 | |
| 2-20 | Ac | Et | S | $CF_2CF_3$ | H | 2 | NMR |
| 2-21 | H | $i\text{-}C_3F_7$ | S | $i\text{-}C_3F_7$ | H | 0 | |
| 2-22 | H | $i\text{-}C_3F_7$ | S | $i\text{-}C_3F_7$ | H | 2 | NMR |
| 2-23 | Ac | $i\text{-}C_3F_7$ | S | $i\text{-}C_3F_7$ | H | 0 | |
| 2-24 | Ac | $i\text{-}C_3F_7$ | S | $i\text{-}C_3F_7$ | H | 2 | |
| 2-25 | H | $CO_2Me$ | O | $CF_3$ | H | 0 | |

TABLE 2-2

| Compound No. | $R^4$ | $R^5$ | $A^6$ | $R^7$ | $R^8$ | m | Physical property value |
|---|---|---|---|---|---|---|---|
| 2-26 | H | $CO_2Me$ | O | $CF_3$ | H | 2 | 156-158 |
| 2-27 | Ac | $CO_2Me$ | O | $CF_3$ | H | 0 | |
| 2-28 | Ac | $CO_2Me$ | O | $CF_3$ | H | 2 | |
| 2-29 | H | $CO_2Me$ | O | $CF_2CF_3$ | H | 0 | |
| 2-30 | H | $CO_2Me$ | O | $CF_2CF_3$ | H | 2 | 157-160 |
| 2-31 | Ac | $CO_2Me$ | O | $CF_2CF_3$ | H | 0 | |
| 2-32 | Ac | $CO_2Me$ | O | $CF_2CF_3$ | H | 2 | 124-125 |
| 2-33 | H | $CO_2H$ | O | $CF_2CF_3$ | H | 0 | |
| 2-34 | H | $CO_2H$ | O | $CF_2CF_3$ | H | 2 | 236-238 |
| 2-35 | Ac | $CO_2H$ | O | $CF_2CF_3$ | H | 0 | |
| 2-36 | Ac | $CO_2H$ | O | $CF_2CF_3$ | H | 2 | |
| 2-37 | H | Br | O | $CF_2CF_3$ | H | 0 | |
| 2-38 | H | Br | O | $CF_2CF_3$ | H | 2 | 147-149 |
| 2-39 | Ac | Br | O | $CF_2CF_3$ | H | 0 | |
| 2-40 | Ac | Br | O | $CF_2CF_3$ | H | 2 | NMR |
| 2-41 | H | Et | O | $CF_2CF_3$ | H | 0 | |
| 2-42 | H | Et | O | $CF_2CF_3$ | H | 2 | 115-117 |
| 2-43 | Ac | Et | O | $CF_2CF_3$ | H | 0 | |
| 2-44 | Ac | Et | O | $CF_2CF_3$ | H | 2 | |
| 2-45 | H | $CO_2Me$ | O | t-Bu | H | 0 | 118-120 |
| 2-46 | H | $CO_2Me$ | O | t-Bu | H | 2 | 120-122 |
| 2-47 | Ac | $CO_2Me$ | O | t-Bu | H | 0 | |
| 2-48 | Ac | $CO_2Me$ | O | t-Bu | H | 2 | 66-69 |
| 2-49 | H | $CO_2Me$ | NMe | $CF_2CF_3$ | H | 0 | |
| 2-50 | H | $CO_2Me$ | NMe | $CF_2CF_3$ | H | 2 | 131-134 |

TABLE 2-3

| Compound No. | $R^4$ | $R^5$ | $A^6$ | $R^7$ | $R^8$ | m | Physical property value |
|---|---|---|---|---|---|---|---|
| 2-51 | Ac | $CO_2Me$ | NMe | $CF_2CF_3$ | H | 0 | |
| 2-52 | Ac | $CO_2Me$ | NMe | $CF_2CF_3$ | H | 2 | 60-63 |
| 2-53 | H | $CO_2Me$ | $NCH_2CF_3$ | H | H | 0 | 115-116 |
| 2-54 | H | $CO_2Me$ | $NCH_2CF_3$ | H | H | 2 | 152-155 |
| 2-55 | Ac | $CO_2Me$ | $NCH_2CF_3$ | H | H | 0 | |
| 2-56 | Ac | $CO_2Me$ | $NCH_2CF_3$ | H | H | 2 | 132-135 |

Specific examples of the compound represented by the following general formula [I-4] are shown in the following table.

[Chem. 25]

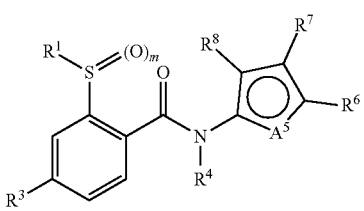

[I-4]

In the formula [I-4] above, $R^3$ represents $CF_3$ and $R^1$ represents Et.

TABLE 3-1

| Compound No. | $R^3$ | $A^5$ | $R^6$ | $R^7$ | $R^8$ | m | Physical property value |
|---|---|---|---|---|---|---|---|
| 3-1 | H | S | $CH(CF_3)_2$ | H | $CO_2Me$ | 0 | 139-140° C. |
| 3-2 | H | S | $CH(CF_3)_2$ | H | $CO_2Me$ | 2 | 187-188° C. |
| 3-3 | Ac | S | $CH(CF_3)_2$ | H | $CO_2Me$ | 0 | 1.431 (23.3° C.) |
| 3-4 | Ac | S | $CH(CF_3)_2$ | H | $CO_2Me$ | 2 | 37-42° C. |

Specific examples of the compound represented by the following general formula [I-5] are shown in the following table.

[Chem. 26]

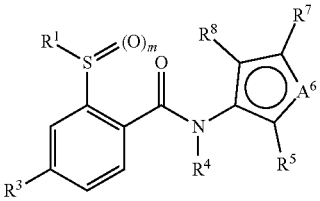

[I-5]

In the formula [I-5] above, $R^3$ represents $CF_3$.

TABLE 4-1

| Compound No. | $R^1$ | $R^4$ | $R^5$ | $A^6$ | $R^7$ | $R^8$ | m | Physical property value |
|---|---|---|---|---|---|---|---|---|
| 4-1 | Et | H | cy-Pr | S | $CF_2CF_3$ | H | 0 | |
| 4-2 | Et | H | cy-Pr | S | $CF_2CF_3$ | H | 2 | NMR |
| 4-3 | Et | Ac | cy-Pr | S | $CF_2CF_3$ | H | 0 | |
| 4-4 | Et | Ac | cy-Pr | S | $CF_2CF_3$ | H | 2 | |
| 4-5 | Et | H | Ph | S | $CF_2CF_3$ | H | 0 | |
| 4-6 | Et | H | Ph | S | $CF_2CF_3$ | H | 2 | 162-163 |
| 4-7 | Et | Ac | Ph | S | $CF_2CF_3$ | H | 0 | |
| 4-8 | Et | Ac | Ph | S | $CF_2CF_3$ | H | 2 | 58-59 |
| 4-9 | Et | H | 3-pyridyl | S | $CF_2CF_3$ | H | 0 | |
| 4-10 | Et | H | 3-pyridyl | S | $CF_2CF_3$ | H | 2 | 240-241 |
| 4-11 | Et | Ac | 3-pyridyl | S | $CF_2CF_3$ | H | 0 | |
| 4-12 | Et | Ac | 3-pyridyl | S | $CF_2CF_3$ | H | 2 | 58-59 |
| 4-13 | Et | H | 3-thienyl | S | $CF_2CF_3$ | H | 0 | |
| 4-14 | Et | H | 3-thienyl | S | $CF_2CF_3$ | H | 2 | 181-182 |
| 4-15 | Et | Ac | 3-thienyl | S | $CF_2CF_3$ | H | 0 | |
| 4-16 | Et | Ac | 3-thienyl | S | $CF_2CF_3$ | H | 2 | 103-104 |
| 4-17 | Et | H | $CO_2Me$ | S | Br | H | 0 | |
| 4-18 | Et | H | $CO_2Me$ | S | Br | H | 2 | 185-186 |
| 4-19 | Et | Ac | $CO_2Me$ | S | Br | H | 0 | |
| 4-20 | Et | Ac | $CO_2Me$ | S | Br | H | 2 | 40-41 |

TABLE 4-2

| Compound No. | $R^1$ | $R^4$ | $R^5$ | $A^6$ | $R^7$ | $R^8$ | m | Physical property value |
|---|---|---|---|---|---|---|---|---|
| 4-21 | Et | H | CO₂Me | S | cy-Pr | H | 0 | |
| 4-22 | Et | H | CO₂Me | S | cy-Pr | H | 2 | 168-169 |
| 4-23 | Et | Ac | CO₂Me | S | cy-Pr | H | 0 | |
| 4-24 | Et | Ac | CO₂Me | S | cy-Pr | H | 2 | 62-63 |
| 4-25 | Et | H | CO₂Me | S | vinyl | H | 0 | |
| 4-26 | Et | H | CO₂Me | S | vinyl | H | 2 | 171-172 |
| 4-27 | Et | Ac | CO₂Me | S | vinyl | H | 0 | |
| 4-28 | Et | Ac | CO₂Me | S | vinyl | H | 2 | 50-51 |
| 4-29 | Et | H | CO₂Me | S | Et | H | 0 | |
| 4-30 | Et | H | CO₂Me | S | Et | H | 2 | |
| 4-31 | Et | Ac | CO₂Me | S | Et | H | 0 | |
| 4-32 | Et | Ac | CO₂Me | S | Et | H | 2 | 48-49 |
| 4-33 | Et | H | CO₂Me | S | i-Pr | H | 0 | |
| 4-34 | Et | H | CO₂Me | S | i-Pr | H | 2 | |
| 4-35 | Et | Ac | CO₂Me | S | i-Pr | H | 0 | |
| 4-36 | Et | Ac | CO₂Me | S | i-Pr | H | 2 | 42-43 |
| 4-37 | Et | H | CO₂Me | S | i-Bu | H | 0 | 89-92 |
| 4-38 | Et | H | CO₂Me | S | i-Bu | H | 2 | 134-135 |
| 4-39 | Et | Ac | CO₂Me | S | i-Bu | H | 0 | |
| 4-40 | Et | Ac | CO₂Me | S | i-Bu | H | 2 | NMR |
| 4-41 | Et | H | CO₂Me | S | i-propenyl | H | 0 | |
| 4-42 | Et | H | CO₂Me | S | i-propenyl | H | 2 | 142-143 |
| 4-43 | Et | Ac | CO₂Me | S | i-propenyl | H | 0 | |
| 4-44 | Et | Ac | CO₂Me | S | i-propenyl | H | 2 | 42-43 |
| 4-45 | Et | H | CO₂Me | S | i-butenyl | H | 0 | 158-161 |
| 4-46 | Et | H | CO₂Me | S | i-butenyl | H | 2 | |
| 4-47 | Et | Ac | CO₂Me | S | i-butenyl | H | 0 | |
| 4-48 | Et | Ac | CO₂Me | S | i-butenyl | H | 2 | |
| 4-49 | Et | H | CO₂Me | S | t-Bu | H | 0 | |
| 4-50 | Et | H | CO₂Me | S | t-Bu | H | 2 | 111-113 |

TABLE 4-3

| Compound No. | $R^1$ | $R^4$ | $R^5$ | $A^6$ | $R^7$ | $R^8$ | m | Physical property value |
|---|---|---|---|---|---|---|---|---|
| 4-51 | Et | Ac | CO₂Me | S | t-Bu | H | 0 | |
| 4-52 | Et | Ac | CO₂Me | S | t-Bu | H | 2 | 58-60 |
| 4-53 | Et | H | CO₂Me | S | Ph | H | 0 | |
| 4-54 | Et | H | CO₂Me | S | Ph | H | 2 | 203-204 |
| 4-55 | Et | Ac | CO₂Me | S | Ph | H | 0 | |
| 4-56 | Et | Ac | CO₂Me | S | Ph | H | 2 | 159-160 |
| 4-57 | Me | H | CO₂Me | O | CF₂CF₃ | H | 0 | |
| 4-58 | Me | H | CO₂Me | O | CF₂CF₃ | H | 2 | 169-173 |
| 4-59 | Me | Ac | CO₂Me | O | CF₂CF₃ | H | 0 | |
| 4-60 | Me | Ac | CO₂Me | O | CF₂CF₃ | H | 2 | NMR |
| 4-61 | Et | COEt | CO₂Me | O | CF₂CF₃ | H | 0 | |
| 4-62 | Et | COEt | CO₂Me | O | CF₂CF₃ | H | 2 | 34-37° C. |
| 4-63 | Et | COi-Pr | CO₂Me | O | CF₂CF₃ | H | 0 | |
| 4-64 | Et | COi-Pr | CO₂Me | O | CF₂CF₃ | H | 2 | 30-35° C. |
| 4-65 | Et | COcy-Pr | CO₂Me | O | CF₂CF₃ | H | 0 | |
| 4-66 | Et | COcy-Pr | CO₂Me | O | CF₂CF₃ | H | 2 | 36-40° C. |
| 4-67 | Et | Cot-Bu | CO₂Me | O | CF₂CF₃ | H | 0 | |
| 4-68 | Et | Cot-Bu | CO₂Me | O | CF₂CF₃ | H | 2 | 36-40° C. |
| 4-69 | Et | CO₂Me | CO₂Me | O | CF₂CF₃ | H | 0 | |
| 4-70 | Et | CO₂Me | CO₂Me | O | CF₂CF₃ | H | 2 | NMR |
| 4-71 | Et | H | CO₂Me | O | CF₂CF₂CF₃ | H | 0 | |
| 4-72 | Et | H | CO₂Me | O | CF₂CF₂CF₃ | H | 2 | 145-147° C. |
| 4-73 | Et | Ac | CO₂Me | O | CF₂CF₂CF₃ | H | 0 | |
| 4-74 | Et | Ac | CO₂Me | O | CF₂CF₂CF₃ | H | 2 | 1.408 (22.7° C.) |
| 4-75 | Et | H | CO₂Me | O | Ph | H | 0 | |
| 4-76 | Et | H | CO₂Me | O | Ph | H | 2 | 228-229 |
| 4-77 | Et | Ac | CO₂Me | O | Ph | H | 0 | |
| 4-78 | Et | Ac | CO₂Me | O | Ph | H | 2 | NMR |
| 4-79 | Et | H | CO₂Me | O | 2-furyl | H | 0 | |
| 4-80 | Et | H | CO₂Me | O | 2-furyl | H | 2 | 224-226 |

TABLE 4-4

| Compound No. | $R^1$ | $R^4$ | $R^5$ | $A^6$ | $R^7$ | $R^8$ | m | Physical property value |
|---|---|---|---|---|---|---|---|---|
| 4-81 | Et | Ac | CO₂Me | O | 2-furyl | H | 0 | |
| 4-82 | Et | Ac | CO₂Me | O | 2-furyl | H | 2 | 67-69 |
| 4-83 | Et | H | CO₂Et | O | CF₂CF₃ | H | 0 | |
| 4-84 | Et | H | CO₂Et | O | CF₂CF₃ | H | 2 | 147-148° C. |
| 4-85 | Et | Ac | CO₂Et | O | CF₂CF₃ | H | 0 | |
| 4-86 | Et | Ac | CO₂Et | O | CF₂CF₃ | H | 2 | 1.474 (22.9° C.) |
| 4-87 | Et | H | CO₂t-Bu | O | CF₂CF₃ | H | 0 | |
| 4-88 | Et | H | CO₂t-Bu | O | CF₂CF₃ | H | 2 | |
| 4-89 | Et | Ac | CO₂t-Bu | O | CF₂CF₃ | H | 0 | |
| 4-90 | Et | Ac | CO₂t-Bu | O | CF₂CF₃ | H | 2 | NMR |
| 4-91 | Et | H | CO₂t-Bu | O | t-Bu | H | 0 | |
| 4-92 | Et | H | CO₂t-Bu | O | t-Bu | H | 2 | NMR |
| 4-93 | Et | Ac | CO₂t-Bu | O | t-Bu | H | 0 | |
| 4-94 | Et | Ac | CO₂t-Bu | O | t-Bu | H | 2 | 116-118° C. |
| 4-95 | Et | H | CO₂Bn | O | t-Bu | H | 0 | |
| 4-96 | Et | H | CO₂Bn | O | t-Bu | H | 2 | 57-59 |
| 4-97 | Et | Ac | CO₂Bn | O | t-Bu | H | 0 | |
| 4-98 | Et | Ac | CO₂Bn | O | t-Bu | H | 2 | 1.5191 (32.3° C.) |
| 4-99 | Et | H | n-Pr | O | CF₂CF₃ | H | 0 | |
| 4-100 | Et | H | n-Pr | O | CF₂CF₃ | H | 2 | |
| 4-101 | Et | Ac | n-Pr | O | CF₂CF₃ | H | 0 | |
| 4-102 | Et | Ac | n-Pr | O | CF₂CF₃ | H | 2 | 1.383 (22.9° C.) |
| 4-103 | Et | H | CON(Me)₂ | O | CF₂CF₃ | H | 0 | |
| 4-104 | Et | H | CON(Me)₂ | O | CF₂CF₃ | H | 2 | 173-174° C. |
| 4-105 | Et | Ac | CON(Me)₂ | O | CF₂CF₃ | H | 0 | |
| 4-106 | Et | Ac | CON(Me)₂ | O | CF₂CF₃ | H | 2 | 30-40° C. |
| 4-107 | Et | H | Ph | O | CF₂CF₃ | H | 0 | |
| 4-108 | Et | H | Ph | O | CF₂CF₃ | H | 2 | 187-197° C. |
| 4-109 | Et | Ac | Ph | O | CF₂CF₃ | H | 0 | |
| 4-110 | Et | Ac | Ph | O | CF₂CF₃ | H | 2 | NMR |

TABLE 4-5

| Compound No. | $R^1$ | $R^4$ | $R^5$ | $A^6$ | $R^7$ | $R^8$ | m | Physical property value |
|---|---|---|---|---|---|---|---|---|
| 4-111 | Et | H | H | O | CF₂CF₃ | H | 0 | |
| 4-112 | Et | H | H | O | CF₂CF₃ | H | 2 | 165-167° C. |
| 4-113 | Et | Ac | H | O | CF₂CF₃ | H | 0 | |
| 4-114 | Et | Ac | H | O | CF₂CF₃ | H | 2 | 1.397 (22.7° C.) |
| 4-115 | Et | H | 3-thienyl | O | CF₂CF₃ | H | 0 | |
| 4-116 | Et | H | 3-thienyl | O | CF₂CF₃ | H | 2 | 198-199 C. |
| 4-117 | Et | Ac | 3-thienyl | O | CF₂CF₃ | H | 0 | |
| 4-118 | Et | Ac | 3-thienyl | O | CF₂CF₃ | H | 2 | NMR |
| 4-119 | Et | H | 3-furyl | O | CF₂CF₃ | H | 0 | |
| 4-120 | Et | H | 3-furyl | O | CF₂CF₃ | H | 2 | |
| 4-121 | Et | Ac | 3-furyl | O | CF₂CF₃ | H | 0 | |
| 4-122 | Et | Ac | 3-furyl | O | CF₂CF₃ | H | 2 | NMR |
| 4-123 | Et | H | SEt | O | CF₂CF₃ | H | 0 | |
| 4-124 | Et | H | SEt | O | CF₂CF₃ | H | 2 | 141-143° C. |
| 4-125 | Et | Ac | SEt | O | CF₂CF₃ | H | 0 | |
| 4-126 | Et | Ac | SEt | O | CF₂CF₃ | H | 2 | NMR |
| 4-127 | Et | H | SO₂Et | O | CF₂CF₃ | H | 0 | |
| 4-128 | Et | H | SO₂Et | O | CF₂CF₃ | H | 2 | 165-167° C. |
| 4-129 | Et | Ac | SO₂Et | O | CF₂CF₃ | H | 0 | |
| 4-130 | Et | Ac | SO₂Et | O | CF₂CF₃ | H | 2 | 1.450 (21.1° C.) |
| 4-131 | Et | H | CO₂Me | NCF₂CF₃ | H | H | 0 | 88-89 |
| 4-132 | Et | H | CO₂Me | NCF₂CF₃ | H | H | 2 | NMR |
| 4-133 | Et | Ac | CO₂Me | NCF₂CF₃ | H | H | 0 | |
| 4-134 | Et | Ac | CO₂Me | NCF₂CF₃ | H | H | 2 | NMR |

[Chem. 27]

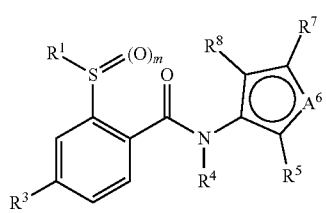

[I-5]

In the formula [I-5] above, $R^3$ represents $CF_3$.

TABLE 5-1

| Compound No. | $R^1$ | $R^4$ | $R^5$ | $A^6$ | $R^7$ | $R^8$ | m | Physical property value |
|---|---|---|---|---|---|---|---|---|
| 5-1 | Et | H | $CO_2Me$ | S | 2,6-diF-Ph | H | 0 | 133-135° C. |
| 5-2 | Et | H | $CO_2Me$ | S | 2,6-diF-Ph | H | 2 | |
| 5-3 | Et | Ac | $CO_2Me$ | S | 2,6-diF-Ph | H | 0 | |
| 5-4 | Et | Ac | $CO_2Me$ | S | 2,6-diF-Ph | H | 2 | |
| 5-5 | Et | H | $CO_2Me$ | S | 2,5-diF-Ph | H | 0 | 152-154° C. |
| 5-6 | Et | H | $CO_2Me$ | S | 2,5-diF-Ph | H | 2 | |
| 5-7 | Et | Ac | $CO_2Me$ | S | 2,5-diF-Ph | H | 0 | |
| 5-8 | Et | Ac | $CO_2Me$ | S | 2,5-diF-Ph | H | 2 | |
| 5-9 | Et | H | $CO_2Me$ | S | 2,3-diF-Ph | H | 0 | 147-149° C. |
| 5-10 | Et | H | $CO_2Me$ | S | 2,3-diF-Ph | H | 2 | 176-177° C. |
| 5-11 | Et | Ac | $CO_2Me$ | S | 2,3-diF-Ph | H | 0 | |
| 5-12 | Et | Ac | $CO_2Me$ | S | 2,3-diF-Ph | H | 2 | |
| 5-13 | Et | H | $CO_2Me$ | S | 3,5-diF-Ph | H | 0 | 157-159° C. |
| 5-14 | Et | H | $CO_2Me$ | S | 3,5-diF-Ph | H | 2 | 122-124° C. |
| 5-15 | Et | Ac | $CO_2Me$ | S | 3,5-diF-Ph | H | 0 | |
| 5-16 | Et | Ac | $CO_2Me$ | S | 3,5-diF-Ph | H | 2 | |
| 5-17 | Et | H | $CO_2Me$ | S | 3,4,5-diF-Ph | H | 0 | 165-166° C. |
| 5-18 | Et | H | $CO_2Me$ | S | 3,4,5-diF-Ph | H | 2 | 184-185° C. |
| 5-19 | Et | Ac | $CO_2Me$ | S | 3,4,5-diF-Ph | H | 0 | |
| 5-20 | Et | Ac | $CO_2Me$ | S | 3,4,5-diF-Ph | H | 2 | |

TABLE 5-2

| Compound No. | $R^1$ | $R^4$ | $R^5$ | $A^6$ | $R^7$ | $R^8$ | m | Physical property value |
|---|---|---|---|---|---|---|---|---|
| 5-21 | Et | H | $CO_2Me$ | S | 2-$CF_3$-Ph | H | 0 | 150-151° C. |
| 5-22 | Et | H | $CO_2Me$ | S | 2-$CF_3$-Ph | H | 2 | 174-176° C. |
| 5-23 | Et | Ac | $CO_2Me$ | S | 2-$CF_3$-Ph | H | 0 | |
| 5-24 | Et | Ac | $CO_2Me$ | S | 2-$CF_3$-Ph | H | 2 | |
| 5-25 | Et | H | $CO_2Me$ | S | 3-$CF_3$-Ph | H | 0 | 154-155° C. |
| 5-26 | Et | H | $CO_2Me$ | S | 3-$CF_3$-Ph | H | 2 | 177-179° C. |
| 5-27 | Et | Ac | $CO_2Me$ | S | 3-$CF_3$-Ph | H | 0 | |
| 5-28 | Et | Ac | $CO_2Me$ | S | 3-$CF_3$-Ph | H | 2 | |
| 5-29 | Et | H | $CO_2Me$ | S | 4-$CF_3$-Ph | H | 0 | 154-155° C. |
| 5-30 | Et | H | $CO_2Me$ | S | 4-$CF_3$-Ph | H | 2 | 133-135° C. |
| 5-31 | Et | Ac | $CO_2Me$ | S | 4-$CF_3$-Ph | H | 0 | |
| 5-32 | Et | Ac | $CO_2Me$ | S | 4-$CF_3$-Ph | H | 2 | |
| 5-33 | Et | H | $CO_2Me$ | S | 3,5-$CF_3$-Ph | H | 0 | 168-169° C. |
| 5-34 | Et | H | $CO_2Me$ | S | 3,5-$CF_3$-Ph | H | 2 | 227-228° C. |
| 5-35 | Et | Ac | $CO_2Me$ | S | 3,5-$CF_3$-Ph | H | 0 | |
| 5-36 | Et | Ac | $CO_2Me$ | S | 3,5-$CF_3$-Ph | H | 2 | |
| 5-37 | Et | H | $CO_2Me$ | S | 3-$OCF_3$-Ph | H | 0 | 130-131° C. |
| 5-38 | Et | H | $CO_2Me$ | S | 3-$OCF_3$-Ph | H | 2 | 171-173° C. |
| 5-39 | Et | Ac | $CO_2Me$ | S | 3-$OCF_3$-Ph | H | 0 | |
| 5-40 | Et | Ac | $CO_2Me$ | S | 3-$OCF_3$-Ph | H | 2 | |
| 5-41 | Et | H | $CO_2Me$ | S | 2-F, 5-$CF_3$-Ph | H | 0 | 166-167° C. |
| 5-42 | Et | H | $CO_2Me$ | S | 2-F, 5-$CF_3$-Ph | H | 2 | 227-228° C. |
| 5-43 | Et | Ac | $CO_2Me$ | S | 2-F, 5-$CF_3$-Ph | H | 0 | |
| 5-44 | Et | Ac | $CO_2Me$ | S | 2-F, 5-$CF_3$-Ph | H | 2 | |
| 5-45 | Et | H | $CO_2Me$ | S | 3,3-dimethyl-1-butynyl | H | 0 | |
| 5-46 | Et | H | $CO_2Me$ | S | 3,3-dimethyl-1-butynyl | H | 2 | 165-167° C. |

TABLE 5-2-continued

| Compound No. | $R^1$ | $R^4$ | $R^5$ | $A^6$ | $R^7$ | $R^8$ | m | Physical property value |
|---|---|---|---|---|---|---|---|---|
| 5-47 | Et | Ac | $CO_2Me$ | S | 3,3-dimethyl-1-butynyl | H | 0 | |
| 5-48 | Et | Ac | $CO_2Me$ | S | 3,3-dimethyl-1-butynyl | H | 2 | |
| 5-49 | Et | H | $CO_2Me$ | S | 3,3,3-trifluoropropyl | H | 0 | |
| 5-50 | Et | H | $CO_2Me$ | S | 3,3,3-trifluoropropyl | H | 2 | 143-146° C. |

TABLE 5-3

| Compound No. | $R^1$ | $R^4$ | $R^5$ | $A^6$ | $R^7$ | $R^8$ | m | Physical property value |
|---|---|---|---|---|---|---|---|---|
| 5-51 | Et | Ac | $CO_2Me$ | S | 3,3,3-trifluoropropyl | H | 0 | |
| 5-52 | Et | Ac | $CO_2Me$ | S | 3,3,3-trifluoropropyl | H | 2 | NMR |
| 5-53 | Et | H | $CO_2Me$ | S | $CO_2$t-Bu | H | 0 | |
| 5-54 | Et | H | $CO_2Me$ | S | $CO_2$t-Bu | H | 2 | 174-176° C. |
| 5-55 | Et | Ac | $CO_2Me$ | S | $CO_2$t-Bu | H | 0 | |
| 5-56 | Et | Ac | $CO_2Me$ | S | $CO_2$t-Bu | H | 2 | |
| 5-57 | Et | H | $CO_2Me$ | S | $CH_2CH_2$t-Bu | H | 0 | |
| 5-58 | Et | H | $CO_2Me$ | S | $CH_2CH_2$t-Bu | H | 2 | 110-112° C. |
| 5-59 | Et | Ac | $CO_2Me$ | S | $CH_2CH_2$t-Bu | H | 0 | |
| 5-60 | Et | Ac | $CO_2Me$ | S | $CH_2CH_2$t-Bu | H | 2 | NMR |
| 5-61 | Et | H | $CO_2Me$ | S | $COCF_2CF_3$ | H | 0 | |
| 5-62 | Et | H | $CO_2Me$ | S | $COCF_2CF_3$ | H | 2 | 167-169° C. |
| 5-63 | Et | Ac | $CO_2Me$ | S | $COCF_2CF_3$ | H | 0 | |
| 5-64 | Et | Ac | $CO_2Me$ | S | $COCF_2CF_3$ | H | 2 | |
| 5-65 | Me | $CO_2Me$ | $CO_2Me$ | O | $CF_2CF_3$ | H | 0 | |
| 5-66 | Me | $CO_2Me$ | $CO_2Me$ | O | $CF_2CF_3$ | H | 2 | 38-39 C. |
| 5-67 | Et | $SO_2Me$ | $CO_2Me$ | O | $CF_2CF_3$ | H | 2 | 153-154° C. |
| 5-68 | Et | $CH_2OCH_3$ | $CO_2Me$ | O | $CF_2CF_3$ | H | 2 | NMR |
| 5-69 | Et | H | $CO_2H$ | O | t-Bu | H | 0 | 182-184° C. |
| 5-70 | Et | H | $CO_2Me$ | O | $CF_2CF_3$ | Br | 0 | |
| 5-71 | Et | H | $CO_2Me$ | O | $CF_2CF_3$ | Br | 2 | 153-155° C. |
| 5-72 | Et | Ac | $CO_2Me$ | O | $CF_2CF_3$ | Br | 0 | |
| 5-73 | Et | Ac | $CO_2Me$ | O | $CF_2CF_3$ | Br | 2 | |

TABLE 6

Appended Table 1 NMR Data

| Compound No. | $^1$H-NMR data ($CDCl_3$) |
|---|---|
| 1-16 | 8.21 (s, 1H), 7.93 (d, 1H), 7.81 (s, 1H), 7.75 (d, 1H), 3.94 (s, 3H), 3.28 (q, 2H), 2.23 (s, 3H), 1.13 (t, 3H) |
| 1-25 | 8.24 (s, 1H), 7.91 (d, 1H), 7.59 (d, 1H), 6.93 (s, 1H), 3.28 (q, 2H), 2.30 (s, 3H), 1.34 (t, 3H) |
| 2-8 | 8.20 (s, 1H), 7.88 (d, 1H), 7.55 (d, 1H), 7.46 (s, 1H), 3.29 (q, 2H), 2.32 (s, 3H), 1.34 (t, 3H) |
| 2-12 | 8.20 (s, 1H), 7.87 (d, 1H), 7.68 (d, 1H), 7.60 (s, 1H), 3.96 (s, 3H), 3.31 (q, 2H), 2.23 (s, 3H), 1.33 (t, 3H) |
| 2-20 | 8.22 (s, 1H), 7.87 (d, 1H), 7.42 (d, 1H), 7.35 (s, 1H), 3.28 (q, 2H), 2.84-2.92 (m, 2H), 2.15 (s, 3H), 1.32-1.41 (m, 6H) |
| 2-22 | 8.48 (s, 1H), 8.06 (m, 2H), 7.15 (d, 1H), 6.70 (m, 1H), 3.69 (q, 2H), 1.45 (t, 3H) |

TABLE 6-continued

Appended Table 1 NMR Data

| Compound No. | $^1$H-NMR data (CDCl$_3$) |
|---|---|
| 2-32 | 8.20 (s, 1H), 7.91 (d, 1H), 7.55 (d, 1H), 7.08 (s, 1H), 3.28 (q, 2H), 2.37 (s, 3H), 1.34 (t, 3H) |
| 2-40 | 8.21 (s, 1H), 7.86 (d, 1H), 7.51 (d, 1H), 6.73 (s, 1H), 4.06 (s, 3H), 3.95 (s, 3H), 3.31 (q, 2H), 2.23 (s, 3H), 1.32 (t, 3H) |

TABLE 7

Appended Table 2 NMR Data

| Compound No. | $^1$H-NMR data (CDCl$_3$) |
|---|---|
| 4-2 | 8.31 (d, 1H), 8.23 (br, 1H), 8.11 (s, 1H), 7.93 (dd, 1H), 7.84 (d, 1H), 3.51 (q, 2H), 1.95 (m, 1H), 1.34 (t, 3H), 1.06 (m, 2H), 0.78 (m, 2H) |
| 4-40 | 8.20 (s, 1H), 7.86 (d, 1H), 7.73 (d, 1H), 6.94 (s, 1H), 3.91 (s, 3H), 3.36 (q, 2H), 2.65 (d, 2H), 2.21 (s, 3H), 1.98 (d, 1H), 1.33 (t, 2H), 0.86 (d, 6H) |
| 4-60 | 8.28 (s, 1H), 7.91 (d, 1H), 7.68 (d, 1H), 7.17 (s, 1H), 4.00 (s, 3H), 3.23 (s, 3H), 2.30 (s, 3H) |
| 4-70 | 8.24 (s, 1H), 7.98 (dd, 1H), 7.84 (d, 1H), 7.15 (s, 1H), 3.95 (s, 3H), 3.67 (s, 3H), 1.34 (t, 3H) |
| 4-78 | 8.21 (s, 1H), 7.92 (d, 1H), 7.78-7.75 (m, 3H), 7.40-7.48 (m, 3H), 6.98 (s, 1H), 3.99 (s, 3H), 3.32 (m, 2H), 2.31 (s, 3H), 1.34 (t, 3H) |
| 4-90 | 8.20 (s, 1H), 7.90 (d, 1H), 7.64 (d, 1H), 7.13 (s, 1H), 3.30 (q, 2H), 2.30(bs, 3H), 1.61 (s, 9H), 1.33 (t, 3H) |
| 4-92 | 9.54 (s, 1H), 8.36 (s, 1H), 8.00 (d, 1H), 7.82 (d, 2H), 7.09 (s, 1H), 3.74 (q, 2H), 1.55 (s, 9H), 1.39-1.31 (m, 12H) |
| 4-110 | 8.20(s, 1H), 7.85-7.79(m, 1H), 7.68(d, 2H), 7.58-7.45(m, 4H), 7.09(s, 1H), 3.27(q, 2H), 2.29(bs, 3H), 1.32(t, 3H) |
| 4-118 | 8.21(d, 1H), 7.86-7.81(m, 1H), 7.75(m, 1H), 7.50(dd, 1H), 7.41(d, 1H), 7.26(s, 1H), 7.05(s, 1H), 3.28(q, 2H), 2.28(bs, 3H), 1.33(t, 3H) |
| 4-122 | 8.21(s, 1H), 7.92(s, 1H), 7.86(d, 1H), 7.57(t, 1H), 7.38(d, 1H), .7.03(s, 1H), 6.72(s, 1H), 3.28(q, 2H), 1.32(t, 3H) |
| 4-126 | 8.20(s, 1H), 7.89(d, 1H), 7.56(d, 1H), 7.04(s, 1H), 3.31(q, 2H), 2.31(s, 3H), 1.34(t, 3H), 1.32(t, 3H) |
| 4-132 | 9.84 (s, 1H), 8.37 (d, 1H), 8.00 (dd, 1H), 7.82 (d, 1H), 7.25 (s, 1H), 6.88 (s, 1H), 5.00 (t, 2H), 3.87 (s, 3H), 3.63 (q, 2H), 1.35 (t, 3H) |
| 4-134 | 8.19 (s, 1H), 7.81 (d, 1H), 7.54 (d, 1H), 6.84 (s, 1H), 6.46 (s, 1H), 5.25-4.89 (m, 2H), 3.93 (s, 3H), 3.33 (q, 2H), 1.32 (t, 3H) |

TABLE 8

Appended Table 3 NMR Data

| Compound No. | $^1$H-NMR data (CDCl$_3$) |
|---|---|
| 5-52 | 8.19 (s, 1H), 7.88 (d, 1H), 7.76 (d, 1H), 7.05 (s, 1H), 3.91 (s, 3H), 3.31 (q, 2H), 3.08 (t, 2H), 2.48 (t, 2H), 2.19 (s, 3H), 1.13 (t, 3H) |
| 5-60 | 8.20 (s, 1H), 7.85-7.92(m, 1H), 7.78-7.82 (m, 1H), 6.96 (s, 1H), 3.90 (s, 3H), 3.32 (q, 2H), 2.78-2.83 (m, 2H), 2.16 (s, 3H), 2.24-2.38 (m, 5H), 0.96 (s, 9H) |
| 5-68 | 8.22 (s, 1H), 7.97-8.04 (m, 1H), 7.75 (dd, 1H), 7.18 (s, 1H), 4.80 (s, 2H), 4.01 (s, 3H), 3.59 (s, 3H), 3.52 (q, 2H), 1.33 (t, 3H) |

Hereinafter, formulation examples are shown, but the present invention is not limited thereto. In the formulation examples, "part(s)" means part(s) by weight.

Formulation Example 1

| | |
|---|---|
| Compound [I] of the present invention | 10 parts |
| Xylene | 70 parts |
| N-methyl pyrrolidone | 10 parts |
| Mixture of polyoxyethylene nonylphenyl ether and calcium alkylbenzene sulfonate | 10 parts |

The above ingredients are uniformly mixed for dissolution to give an emulsifiable concentrate formulation.

Formulation Example 2

| | |
|---|---|
| Compound [I] of the present invention | 3 parts |
| Clay powder | 82 parts |
| Diatomite powder | 15 parts |

The above ingredients are uniformly mixed and then pulverized to give a dust formulation.

Formulation Example 3

| | |
|---|---|
| Compound [I] of the present invention | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granule formulation.

Formulation Example 4

| | |
|---|---|
| Compound [I] of the present invention | 20 parts |
| Kaolinite and synthetic high-dispersion silicic acid | 75 parts |
| Mixture of polyoxyethylene nonylphenyl ether and calcium alkylbenzene sulfonate | 5 parts |

The above ingredients are uniformly mixed and then pulverized to give a wettable powder formulation.

Formulation Example 5

| | |
|---|---|
| Compound [I] of the present invention | 10 parts |
| Mixture of nonionic and anionic surfactants (Sorpol 3105 (manufactured by Toho Chemical Industry Co., Ltd.)) | 5 parts |
| Propylene glycol | 2 parts |
| Xanthan gum | 1 part |
| water | 82 parts |

Preparation Procedure:

The above ingredients other than water are uniformly mixed, and the mixture is dispersed in water to give a flowable formulation.

Hereinafter, test examples in connection with the present invention are shown, but the present invention is not limited thereto.

Test Example 1

Test for Control Efficacy on Wheat Powdery Mildew

Agrochemical formulations prepared from the compounds of the present invention according to Formulation Example 1 were diluted with water to predetermined concentrations. The diluted agrochemical formulations were applied to the foliage of wheat plants (variety: Nourin No. 61) at the one- to two-leaf stage grown in pots of 6 cm in diameter. The application rate was 10 mL per pot. After air-dried, the wheat plants were inoculated by dusting with conidia of the wheat powdery mildew fungus *Blumeria graminis* and kept in a greenhouse. At 7 days after the inoculation, the control efficacy was evaluated according to the criteria shown below.

[Math. 1]

$$\text{Control rate (\%)} = 100 \times (\text{Average percent lesion area in a non-treatment plot} - \text{Average percent lesion area in a treatment plot}) / \text{Average percent lesion area in a non-treatment plot} \quad \text{Equation 1:}$$

Criteria
- 0: the control rate is 9% or less.
- 1: the control rate is 10 to 19%.
- 2: the control rate is 20 to 29%.
- 3: the control rate is 30 to 39%.
- 4: the control rate is 40 to 49%.
- 5: the control rate is 50 to 59%.
- 6: the control rate is 60 to 69%.
- 7: the control rate is 70 to 79%.
- 8: the control rate is 80 to 89%.
- 9: the control rate is 90 to 99%.
- 10: the control rate is 100%.

The results of the test revealed that the compounds 1-8, 1-10, 1-12, 1-16, 2-2, 2-6, 2-8, 2-10, 2-12, 2-18, 2-20, 2-22, 2-26, 2-30, 2-32, 2-34, 2-38, 2-40, 2-45, 2-46, 2-48, 2-50, 2-52, 2-54, 3-2, 3-3, 3-4, 4-2, 4-8, 4-12, 4-16, 4-24, 4-36, 4-38, 4-40, 4-44, 4-50, 4-56, 4-62, 4-64, 4-66, 4-68, 4-72, 4-76, 4-78, 4-84, 4-86, 4-94, 4-98, 4-102, 4-106, 4-110, 4-112, 4-114, 4-130, 4-131, 4-132, 4-134, 5-22, 5-50, 5-52, 5-60, 5-62, 5-66, 5-67, and 5-71 of the present invention at a concentration of 50 ppm or less showed the activity of level 1 or higher.

The compounds 1-8, 1-10, 1-16, 2-2, 2-6, 2-8, 2-10, 2-12, 2-18, 2-20, 2-26, 2-30, 2-32, 2-34, 2-38, 2-40, 2-45, 2-46, 2-48, 2-50, 2-52, 3-2, 3-4, 4-8, 4-16, 4-36, 4-40, 4-50, 4-52, 4-58, 4-60, 4-62, 4-64, 4-66, 4-68, 4-70, 4-72, 4-74, 4-84, 4-86, 4-98, 4-110, 4-116, 4-118, 4-122, 4-124, 4-126, 4-134, 5-50, 5-52, 5-60, 5-66, and 5-67 of the present invention at a concentration of 10 ppm showed the activity of level 1 or higher.

The compounds 2-6, 2-8, 2-10, 2-12, 2-26, 2-30, 2-32, 2-34, 2-40, 2-46, 2-48, 2-50, 2-52, 3-4, 4-16, 4-40, 4-52, 4-58, 4-60, 4-62, 4-64, 4-66, 4-68, 4-70, 4-72, 4-74, 4-84, 4-86, 4-98, 4-110, 4-118, 4-126, 4-134, and 5-67 of the present invention at a concentration of 10 ppm showed the activity of level 10.

Test Example 2

Test for Control Efficacy on Barley Powdery Mildew

Agrochemical formulations prepared from the compounds of the present invention according to Formulation Example 1 were diluted with water to predetermined concentrations. The diluted agrochemical formulations of predetermined concentrations were applied to the foliage of barley plants (variety: Kanto No. 6) at the one-leaf stage grown in pots. The application rate was 50 mL per pot. On the day after the application, the barley plants were inoculated by dusting with spores obtained from barley leaves infected with barley powdery mildew (*Blumeria graminis hordei*) and kept in a greenhouse. At 7 days after the inoculation, the control efficacy was evaluated according to the criteria of Test Example 1.

The results of the test revealed that the compounds 1-8, 1-10, 1-12, 1-16, 2-10, 2-12, 2-30, 2-32, 2-34, 3-2, 3-4, 4-1, 4-8, 4-12, 4-16, 4-20, 4-24, 4-36, 4-38, 4-40, 4-44, 4-50, 4-62, 4-64, 4-66, 4-68, 4-72, 4-78, 4-84, 4-86, 4-98, 4-102, 4-106, 4-110, 4-112, 4-114, 4-130, 4-132, 4-134, 5-46, 5-50, 5-52, 5-60, 5-62, 5-67, and 5-71 of the present invention at a concentration of 50 ppm showed the activity of level 1 or higher.

The compounds 1-8, 2-2, 2-6, 2-8, 2-10, 2-12, 2-18, 2-20, 2-26, 2-30, 2-32, 2-34, 2-38, 2-40, 2-42, 2-45, 2-46, 2-48, 3-2, 3-4, 4-8, 4-16, 4-24, 4-36, 4-38, 4-40, 4-50, 4-52, 4-58, 4-60, 4-62, 4-64, 4-66, 4-68, 4-70, 4-72, 4-74, 4-84, 4-86, 4-98, 4-102, 4-110, 4-114, 4-118, 4-112, 4-124, 4-126, 4-134, 5-50, 5-52, 5-60, 5-66, and 5-67 of the present invention at a concentration of 10 ppm showed the activity of level 1 or higher.

The compounds 2-6, 2-8, 2-10, 2-12, 2-20, 2-26, 2-30, 2-32, 2-34, 2-38, 2-40, 2-46, 2-48, 3-4, 4-16, 4-40, 4-52, 4-58, 4-60, 4-62, 4-64, 4-66, 4-68, 4-70, 4-72, 4-74, 4-86, 4-98, 4-110, 4-114, 4-118, 4-126, 5-52, and 5-66 of the present invention at a concentration of 10 ppm showed the activity of level 10.

Test Example 3

Test for Control Efficacy on Cucumber Powdery Mildew

Agrochemical formulations prepared from the compounds of the present invention according to Formulation Example 1 were diluted with water to a predetermined concentration. The diluted agrochemical formulations of predetermined concentrations were applied to the foliage of cucumber plants (variety: Suyo) at the one-leaf stage grown in pots. The application rate was 50 mL per pot. On the day after the application, the cucumber plants were inoculated with conidia of cucumber powdery mildew (*Sphaerotheca cucurbitae*). At 8 days after the inoculation, the disease severity index was examined, and the control rate was determined according to equation 1 of Test Example 1.

The results of the test revealed that the compounds 1-8, 1-14, 1-16, 2-2, 2-6, 2-8, 2-10, 2-12, 2-18, 2-20, 2-26, 2-30, 2-32, 2-34, 2-38, 2-40, 2-42, 2-46, 2-48, 2-50, 2-52, 3-2, 3-4, 4-2, 4-8, 4-14, 4-16, 4-20, 4-24, 4-36, 4-38, 4-40, 4-44, 4-50, 4-52, 4-56, 4-58, 4-60, 4-62, 4-64, 4-66, 4-68, 4-70, 4-72, 4-74, 4-78, 4-84, 4-86, 4-98, 4-102, 4-110, 4-114, 4-116, 4-118, 4-122, 4-124, 4-126, 4-132, 4-134, 5-46, 5-50, 5-52, 5-60, 5-66, and 5-67 of the present invention at a concentration of 10 ppm showed the activity of level 1 or higher.

The compounds 2-2, 2-6, 2-8, 2-10, 2-12, 2-20, 2-26, 2-30, 2-32, 2-38, 2-40, 2-46, 2-48, 2-50, 2-52, 3-4, 4-2, 4-16, 4-38, 4-40, 4-50, 4-52, 4-58, 4-60, 4-62, 4-64, 4-66, 4-68, 4-70, 4-72, 4-74, 4-84, 4-86, 4-102, 4-110, 4-116, 4-118, 4-124, 4-126, 4-134, 5-66, and 5-67 of the present invention at a concentration of 10 ppm showed the activity of level 10.

INDUSTRIAL APPLICABILITY

The amide compound of the present invention is effective for controlling diseases which may infest cereals, fruit trees, vegetables, other crops, and ornamental flowering plants and is thus a useful agrochemical.

The invention claimed is:
1. An amide compound represented by the following formula [I]:

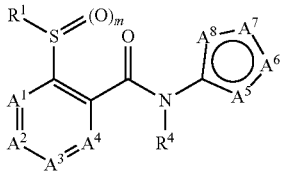

wherein
$R^1$ represents (a1) a $(C_1-C_6)$ alkyl group,
m represents an integer of 0, 1, or 2,
$A^1$, $A^3$, and $A^4$ each represent $C-R^2$,
$R^2$ represents
  (b1) a hydrogen atom;
  (b2) a halogen atom;
  (b3) a $(C_1-C_6)$ alkyl group;
  (b4) a $(C_3-C_6)$ cycloalkyl group; or
  (b5) a halo $(C_1-C_6)$ alkyl group,
$A^2$ represents $C-R^3$,
$R^3$ represents
  (c1) a halogen atom;
  (c2) a $(C_1-C_6)$ alkyl group;
  (c3) a $(C_3-C_6)$ cycloalkyl group;
  (c4) a halo $(C_1-C_6)$ alkyl group;
  (c5) a $(C_1-C_6)$ alkoxy group;
  (c6) a halo $(C_1-C_6)$ alkoxy group;
  (c7) a $(C_1-C_6)$ alkylthio group;
  (c8) a halo $(C_1-C_6)$ alkylthio group;
  (c9) a cyano $(C_1-C_6)$ alkyl group;
  (c10) a cyano $(C_3-C_6)$ cycloalkyl group;
  (c11) a $(C_3-C_6)$ cycloalkyl $(C_1-C_6)$ alkyl group;
  (c12) a $(C_1-C_6)$ alkoxy $(C_1-C_6)$ alkyl group;
  (c13) a $(C_1-C_6)$ alkoxycarbonyl $(C_1-C_6)$ alkyl group;
  (c14) a $(C_1-C_6)$ alkylcarbonyl group;
  (c15) a halo $(C_1-C_6)$ alkylcarbonyl group;
  (c16) a $(C_3-C_6)$ cycloalkylcarbonyl group;
  (c17) a $(C_1-C_6)$ alkoxycarbonyl group;
  (c18) a $(C_1-C_6)$ alkylthio $(C_1-C_6)$ alkyl group;
  (c19) a $(C_1-C_6)$ alkylsulfinyl $(C_1-C_6)$ alkyl group;
  (c20) a $(C_1-C_6)$ alkylsulfonyl $(C_1-C_6)$ alkyl group;
  (c21) a $(C_2-C_6)$ alkenyl group;
  (c22) a $(C_2-C_6)$ alkynyl group;
  (c23) a $(C_1-C_6)$ alkylsulfinyl group;
  (c24) a halo $(C_1-C_6)$ alkylsulfinyl group;
  (c25) a $(C_1-C_6)$ alkylsulfonyl group;
  (c26) a halo $(C_1-C_6)$ alkylsulfonyl group;
  (c27) an R'(R") aminocarbonyl group wherein R' and R" may be the same or different and each represent one group selected from a hydrogen atom, a $(C_1-C_6)$ alkyl group, and a halo $(C_1-C_6)$ alkyl group;
  (c28) an R" carbonyl (R') amino group wherein R' and R" are as defined above; or
  (c29) a group represented by the structural formula (R')C=N—OR" wherein R' and R" are as defined above,
$R^4$ represents
  (d1) a hydrogen atom;
  (d2) a $(C_1-C_6)$ alkyl group;
  (d3) a halo $(C_1-C_6)$ alkyl group;
  (d4) a cyano $(C_1-C_6)$ alkyl group;
  (d5) a $(C_3-C_6)$ cycloalkyl group;
  (d6) a $(C_3-C_6)$ cycloalkyl $(C_1-C_6)$ alkyl group;
  (d7) a $(C_1-C_6)$ alkoxy $(C_1-C_6)$ alkyl group;
  (d8) a $(C_1-C_6)$ alkoxycarbonyl $(C_1-C_6)$ alkyl group;
  (d9) a $(C_1-C_6)$ alkylcarbonyl group;
  (d10) a halo $(C_1-C_6)$ alkylcarbonyl group;
  (d11) a $(C_3-C_6)$ cycloalkylcarbonyl group;
  (d12) a $(C_1-C_6)$ alkoxycarbonyl group;
  (d13) a $(C_1-C_6)$ alkylthio $(C_1-C_6)$ alkyl group;
  (d14) a $(C_1-C_6)$ alkylsulfinyl $(C_1-C_6)$ alkyl group;
  (d15) a $(C_1-C_6)$ alkylsulfonyl $(C_1-C_6)$ alkyl group;
  (d16) a tri-$(C_1-C_3)$ alkylsilyl $(C_1-C_6)$ alkyl group;
  (d17) a $(C_2-C_6)$ alkenyl group;
  (d18) a $(C_2-C_6)$ alkynyl group;
  (d19) a $(C_1-C_6)$ alkylsulfonyl group; or
  (d20) a halo $(C_1-C_6)$ alkylsulfonyl group,
and the heterocyclic ring moiety represented by

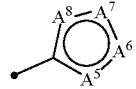

is selected from one of the following groups:

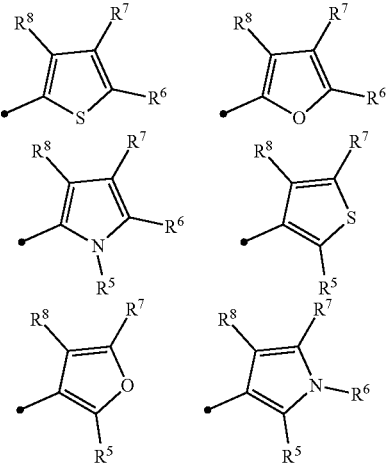

$R^5$ represents
  (e1) a hydrogen atom;
  (e2) a halogen atom;
  (e3) a $(C_1-C_6)$ alkyl group;
  (e4) a halo $(C_1-C_6)$ alkyl group;
  (e5) a $(C_1-C_6)$ alkoxy group;
  (e6) a halo $(C_1-C_6)$ alkoxy group;
  (e7) a $(C_1-C_6)$ alkylthio group;
  (e8) a halo $(C_1-C_6)$ alkylthio group;
  (e9) a cyano $(C_1-C_6)$ alkyl group;
  (e10) a $(C_3-C_6)$ cycloalkyl group;
  (e11) a $(C_3-C_6)$ cycloalkyl $(C_1-C_6)$ alkyl group;
  (e12) a $(C_1-C_6)$ alkoxy $(C_1-C_6)$ alkyl group;
  (e13) a $(C_1-C_6)$ alkoxycarbonyl $(C_1-C_6)$ alkyl group;
  (e14) a $(C_1-C_6)$ alkylcarbonyl group;
  (e15) a halo $(C_1-C_6)$ alkylcarbonyl group;
  (e16) a $(C_3-C_6)$ cycloalkylcarbonyl group;
  (e17) a carboxyl group;
  (e18) a $(C_1-C_6)$ alkoxycarbonyl group;
  (e19) a benzyloxycarbonyl group; or
  (e20) a substituted benzyloxycarbonyl group having, on the ring, 1 to 5 substituents selected from a halogen atom, a nitro group, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_2$-$C_6$) alkenyl group, a halo ($C_2$-$C_6$) alkenyl group, a ($C_2$-$C_6$) alkynyl group, a ($C_3$-$C_6$) cycloalkyl group, a ($C_2$-$C_6$) alkenyloxy group, a halo ($C_2$-$C_6$) alkenyloxy group, a ($C_1$-$C_6$) alkylthio group, a halo ($C_1$-$C_6$) alkylthio group, a ($C_1$-$C_6$) alkylsulfonyloxy group, a halo ($C_1$-$C_6$) alkylsulfonyloxy group, a ($C_1$-$C_6$) alkylsulfinyl group, a halo ($C_1$-$C_6$) alkylsulfinyl group, a ($C_1$-$C_6$) alkylsulfonyl group, a halo ($C_1$-$C_6$) alkylsulfonyl group, a ($C_2$-$C_6$) alkenylthio group, a halo ($C_2$-$C_6$) alkenylthio group, a ($C_2$-$C_6$) alkenylsulfinyl group, a halo ($C_2$-$C_6$) alkenylsulfinyl group, a ($C_2$-$C_6$) alkenylsulfonyl group, a halo ($C_2$-$C_6$) alkenylsulfonyl group, a mono-($C_1$-$C_6$) alkylamino group, a di-($C_1$-$C_6$) alkylamino group (wherein the alkyl groups may be the same or different), a ($C_1$-$C_6$) alkylsulfonylamino group, a halo ($C_1$-$C_6$) alkylsulfonylamino group, a ($C_1$-$C_6$) alkylcarbonyl group, a halo ($C_1$-$C_6$) alkylcarbonyl group, a ($C_1$-$C_6$) alkyloxycarbonyl group, or a phenyl group, wherein, when the number of the substituents is more than one, these substituents may be the same or different;

(e21) a ($C_1$-$C_6$) alkylthio ($C_1$-$C_6$) alkyl group;
(e22) a ($C_1$-$C_6$) alkylsulfinyl ($C_1$-$C_6$) alkyl group;
(e23) a ($C_1$-$C_6$) alkylsulfonyl ($C_1$-$C_6$) alkyl group;
(e24) a ($C_2$-$C_6$) alkenyl group;
(e25) a ($C_2$-$C_6$) alkynyl group;
(e26) a ($C_1$-$C_6$) alkylsulfinyl group;
(e27) a halo ($C_1$-$C_6$) alkylsulfinyl group;
(e28) a ($C_1$-$C_6$) alkylsulfonyl group;
(e29) a halo ($C_1$-$C_6$) alkylsulfonyl group;
(e30) a phenyl group;
(e31) a substituted phenyl group having, on the ring, 1 to 5 substituents selected from a halogen atom, a nitro group, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_2$-$C_6$) alkenyl group, a halo ($C_2$-$C_6$) alkenyl group, a ($C_2$-$C_6$) alkynyl group, a ($C_3$-$C_6$) cycloalkyl group, a ($C_2$-$C_6$) alkenyloxy group, a halo ($C_2$-$C_6$) alkenyloxy group, a ($C_1$-$C_6$) alkylthio group, a halo ($C_1$-$C_6$) alkylthio group, a ($C_1$-$C_6$) alkylsulfonyloxy group, a halo ($C_1$-$C_6$) alkylsulfonyloxy group, a ($C_1$-$C_6$) alkylsulfinyl group, a halo ($C_1$-$C_6$) alkylsulfinyl group, a ($C_1$-$C_6$) alkylsulfonyl group, a halo ($C_1$-$C_6$) alkylsulfonyl group, a ($C_2$-$C_6$) alkenylthio group, a halo ($C_2$-$C_6$) alkenylthio group, a ($C_2$-$C_6$) alkenylsulfinyl group, a halo ($C_2$-$C_6$) alkenylsulfinyl group, a ($C_2$-$C_6$) alkenylsulfonyl group, a halo ($C_2$-$C_6$) alkenylsulfonyl group, a mono-($C_1$-$C_6$) alkylamino group, a di-($C_1$-$C_6$) alkylamino group (wherein the alkyl groups may be the same or different), a ($C_1$-$C_6$) alkylsulfonylamino group, a halo ($C_1$-$C_6$) alkylsulfonylamino group, a ($C_1$-$C_6$) alkylcarbonyl group, a halo ($C_1$-$C_6$) alkylcarbonyl group, a ($C_1$-$C_6$) alkyloxycarbonyl group, or a phenyl group, wherein, when the number of the substituents is more than one, these substituents may be the same or different;

(e32) a heterocyclic group; or
(e33) a heterocyclic group having, on the ring, 1 to 3 substituents selected from the group consisting of a halogen atom, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_1$-$C_6$) alkylthio group, a halo ($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group, and a halo ($C_1$-$C_6$) alkylsulfonyl group, wherein, when the number of the substituents is more than one, these substituents may be the same or different, $R^6$ represents
(f1) a hydrogen atom;
(f2) a halogen atom;
(f3) a ($C_1$-$C_6$) alkyl group;
(f4) a halo ($C_1$-$C_6$) alkyl group;
(f5) a ($C_1$-$C_6$) alkoxy group;
(f6) a halo ($C_1$-$C_6$) alkoxy group;
(f7) a ($C_1$-$C_6$) alkylthio group;
(f8) a halo ($C_1$-$C_6$) alkylthio group;
(f9) a cyano ($C_1$-$C_6$) alkyl group;
(f10) a ($C_3$-$C_6$) cycloalkyl group;
(f11) a ($C_3$-$C_6$) cycloalkyl ($C_1$-$C_6$) alkyl group;
(f12) a ($C_1$-$C_6$) alkoxy ($C_1$-$C_6$) alkyl group;
(f13) a ($C_1$-$C_6$) alkoxycarbonyl ($C_1$-$C_6$) alkyl group;
(f14) a ($C_1$-$C_6$) alkylcarbonyl group;
(f15) a halo ($C_1$-$C_6$) alkylcarbonyl group;
(f16) a ($C_3$-$C_6$) cycloalkylcarbonyl group;
(f17) a ($C_1$-$C_6$) alkoxycarbonyl group;
(f18) a ($C_1$-$C_6$) alkylthio ($C_1$-$C_6$) alkyl group;
(f19) a ($C_1$-$C_6$) alkylsulfinyl ($C_1$-$C_6$) alkyl group;
(f20) a ($C_1$-$C_6$) alkylsulfonyl ($C_1$-$C_6$) alkyl group;
(f21) a ($C_2$-$C_6$) alkenyl group;
(f22) a ($C_2$-$C_6$) alkynyl group;
(f23) a ($C_1$-$C_6$) alkylsulfinyl group;
(f24) a halo ($C_1$-$C_6$) alkylsulfinyl group;
(f25) a ($C_1$-$C_6$) alkylsulfonyl group;
(f26) a halo ($C_1$-$C_6$) alkylsulfonyl group;
(f27) a phenyl group; or
(f28) a substituted phenyl group having, on the ring, 1 to 5 substituents selected from a halogen atom, a nitro group, a cyano group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_2$-$C_6$) alkenyl group, a halo ($C_2$-$C_6$) alkenyl group, a ($C_2$-$C_6$) alkynyl group, a ($C_3$-$C_6$) cycloalkyl group, a ($C_2$-$C_6$) alkenyloxy group, a halo ($C_2$-$C_6$) alkenyloxy group, a ($C_1$-$C_6$) alkylthio group, a halo ($C_1$-$C_6$) alkylthio group, a ($C_1$-$C_6$) alkylsulfonyloxy group, a halo ($C_1$-$C_6$) alkylsulfonyloxy group, a ($C_1$-$C_6$) alkylsulfinyl group, a halo ($C_1$-$C_6$) alkylsulfinyl group, a ($C_1$-$C_6$) alkylsulfonyl group, a halo ($C_1$-$C_6$) alkylsulfonyl group, a ($C_2$-$C_6$) alkenylthio group, a halo ($C_2$-$C_6$) alkenylthio group, a ($C_2$-$C_6$) alkenylsulfinyl group, a halo ($C_2$-$C_6$) alkenylsulfinyl group, a ($C_2$-$C_6$) alkenylsulfonyl group, a halo ($C_2$-$C_6$) alkenylsulfonyl group, a mono-($C_1$-$C_6$) alkylamino group, a di-($C_1$-$C_6$) alkylamino group (wherein the alkyl groups may be the same or different), a ($C_1$-$C_6$) alkylsulfonylamino group, a halo ($C_1$-$C_6$) alkylsulfonylamino group, a ($C_1$-$C_6$) alkylcarbonyl group, a halo ($C_1$-$C_6$) alkylcarbonyl group, a ($C_1$-$C_6$) alkyloxycarbonyl group, or a phenyl group, wherein, when the number of the substituents is more than one, these substituents may be the same or different, $R^7$ represents
(g1) a hydrogen atom;
(g2) a halogen atom;
(g3) a ($C_1$-$C_6$) alkyl group;
(g4) a halo ($C_1$-$C_6$) alkyl group;

(g5) a $(C_1-C_6)$ alkoxy group;
(g6) a halo $(C_1-C_6)$ alkoxy group;
(g7) a $(C_1-C_6)$ alkylthio group;
(g8) a halo $(C_1-C_6)$ alkylthio group;
(g9) a cyano $(C_1-C_6)$ alkyl group;
(g10) a $(C_3-C_6)$ cycloalkyl group;
(g11) a $(C_3-C_6)$ cycloalkyl $(C_1-C_6)$ alkyl group;
(g12) a $(C_1-C_6)$ alkoxy $(C_1-C_6)$ alkyl group;
(g13) a $(C_1-C_6)$ alkoxycarbonyl $(C_1-C_6)$ alkyl group;
(g14) a $(C_1-C_6)$ alkylcarbonyl group;
(g15) a halo $(C_1-C_6)$ alkylcarbonyl group;
(g16) a $(C_3-C_6)$ cycloalkylcarbonyl group;
(g17) a $(C_1-C_6)$ alkoxycarbonyl group;
(g18) a $(C_1-C_6)$ alkylthio $(C_1-C_6)$ alkyl group;
(g19) a $(C_1-C_6)$ alkylsulfinyl $(C_1-C_6)$ alkyl group;
(g20) a $(C_1-C_6)$ alkylsulfonyl $(C_1-C_6)$ alkyl group;
(g21) a $(C_2-C_6)$ alkenyl group;
(g22) a $(C_2-C_6)$ alkynyl group;
(g23) a $(C_1-C_6)$ alkylsulfinyl group;
(g24) a halo $(C_1-C_6)$ alkylsulfinyl group;
(g25) a $(C_1-C_6)$ alkylsulfonyl group;
(g26) a halo $(C_1-C_6)$ alkylsulfonyl group;
(g27) a phenyl group;
(g28) a substituted phenyl group having, on the ring, 1 to 5 substituents selected from a halogen atom, a nitro group, a cyano group, a $(C_1-C_6)$ alkyl group, a halo $(C_1-C_6)$ alkyl group, a $(C_1-C_6)$ alkoxy group, a halo $(C_1-C_6)$ alkoxy group, a $(C_2-C_6)$ alkenyl group, a halo $(C_2-C_6)$ alkenyl group, a $(C_2-C_6)$ alkynyl group, a $(C_3-C_6)$ cycloalkyl group, a $(C_2-C_6)$ alkenyloxy group, a halo $(C_2-C_6)$ alkenyloxy group, a $(C_1-C_6)$ alkylthio group, a halo $(C_1-C_6)$ alkylthio group, a $(C_1-C_6)$ alkylsulfonyloxy group, a halo $(C_1-C_6)$ alkylsulfonyloxy group, a $(C_1-C_6)$ alkylsulfinyl group, a halo $(C_1-C_6)$ alkylsulfinyl group, a $(C_1-C_6)$ alkylsulfonyl group, a halo $(C_1-C_6)$ alkylsulfonyl group, a $(C_2-C_6)$ alkenylthio group, a halo $(C_2-C_6)$ alkenylthio group, a $(C_2-C_6)$ alkenylsulfinyl group, a halo $(C_2-C_6)$ alkenylsulfinyl group, a $(C_2-C_6)$ alkenylsulfonyl group, a halo $(C_2-C_6)$ alkenylsulfonyl group, a mono-$(C_1-C_6)$ alkylamino group, a di-$(C_1-C_6)$ alkylamino group (wherein the alkyl groups may be the same or different), a $(C_1-C_6)$ alkylsulfonylamino group, a halo $(C_1-C_6)$ alkylsulfonylamino group, a $(C_1-C_6)$ alkylcarbonyl group, a halo $(C_1-C_6)$ alkylcarbonyl group, a $(C_1-C_6)$ alkyloxycarbonyl group, or a phenyl group,
wherein, when the number of the substituents is more than one, these substituents may be the same or different;
(g29) a heterocyclic group; or
(g30) a heterocyclic group having, on the ring, 1 to 3 substituents selected from the group consisting of a halogen atom, a $(C_1-C_6)$ alkyl group, a halo $(C_1-C_6)$ alkyl group, a $(C_1-C_6)$ alkoxy group, a halo $(C_1-C_6)$ alkoxy group, a $(C_1-C_6)$ alkylthio group, a halo $(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group, and a halo $(C_1-C_6)$ alkylsulfonyl group,
wherein, when the number of the substituents is more than one, these substituents may be the same or different, and
$R^8$ represents
(h1) a hydrogen atom;
(h2) a halogen atom;
(h3) a $(C_1-C_6)$ alkyl group;
(h4) a halo $(C_1-C_6)$ alkyl group;
(h5) a $(C_1-C_6)$ alkoxy group;
(h6) a halo $(C_1-C_6)$ alkoxy group;
(h7) a $(C_1-C_6)$ alkylthio group;
(h8) a halo $(C_1-C_6)$ alkylthio group;
(h9) a cyano $(C_1-C_6)$ alkyl group;
(h10) a $(C_3-C_6)$ cycloalkyl group;
(h11) a $(C_3-C_6)$ cycloalkyl $(C_1-C_6)$ alkyl group;
(h12) a $(C_1-C_6)$ alkoxy $(C_1-C_6)$ alkyl group;
(h13) a $(C_1-C_6)$ alkoxycarbonyl $(C_1-C_6)$ alkyl group;
(h14) a $(C_1-C_6)$ alkylcarbonyl group;
(h15) a halo $(C_1-C_6)$ alkylcarbonyl group;
(h16) a $(C_3-C_6)$ cycloalkylcarbonyl group;
(h17) a $(C_1-C_6)$ alkoxycarbonyl group;
(h18) a $(C_1-C_6)$ alkylthio $(C_1-C_6)$ alkyl group;
(h19) a $(C_1-C_6)$ alkylsulfinyl $(C_1-C_6)$ alkyl group;
(h20) a $(C_1-C_6)$ alkylsulfonyl $(C_1-C_6)$ alkyl group;
(h21) a $(C_2-C_6)$ alkenyl group;
(h22) a $(C_2-C_6)$ alkynyl group;
(h23) a $(C_1-C_6)$ alkylsulfinyl group;
(h24) a halo $(C_1-C_6)$ alkylsulfinyl group;
(h25) a $(C_1-C_6)$ alkylsulfonyl group; or
(h26) a halo $(C_1-C_6)$ alkylsulfonyl group,
or a salt thereof.

2. The amide compound or the salt thereof according to claim 1, wherein,
$R^2$ represents (b1) a hydrogen atom,
$A^2$ represents C—$R^3$, and
$R^3$ represents (c1) a halogen atom or (c4) a halo $(C_1-C_6)$ alkyl group.

3. The amide compound or the salt thereof according to claim 1, wherein
$R^3$ represents
(c2) a $(C_1-C_6)$ alkyl group or
(c4) a halo $(C_1-C_3)$ alkyl group, and
$R^4$ represents
(d1) a hydrogen atom;
(d2) a $(C_1-C_6)$ alkyl group;
(d7) a $(C_1-C_6)$ alkoxy $(C_1-C_6)$ alkyl group;
(d9) a $(C_1-C_6)$ alkylcarbonyl group;
(d10) a halo $(C_1-C_6)$ alkylcarbonyl group;
(d11) a $(C_3-C_6)$ cycloalkylcarbonyl group;
(d12) a $(C_1-C_6)$ alkoxycarbonyl group;
(d17) a $(C_2-C_6)$ alkenyl group;
(d18) a $(C_2-C_6)$ alkynyl group;
(d19) a $(C_1-C_6)$ alkylsulfonyl group; or
(d20) a halo $(C_1-C_6)$ alkylsulfonyl group.

4. The amide compound or the salt thereof according to claim 1, wherein
$R^2$ represents (b1) a hydrogen atom,
$R^3$ represents (c4) a halo $(C_1-C_3)$ alkyl group,
$R^4$ represents
(d2) a $(C_1-C_6)$ alkyl group;
(d9) a $(C_1-C_6)$ alkylcarbonyl group;
(d10) a halo $(C_1-C_6)$ alkylcarbonyl group; or
(d11) a $(C_3-C_6)$ cycloalkylcarbonyl group,
$R^5$ represents
(e2) a halogen atom;
(e3) a $(C_1-C_6)$ alkyl group;
(e4) a halo $(C_1-C_6)$ alkyl group;
(e10) a $(C_3-C_6)$ cycloalkyl group;
(e14) a $(C_1-C_6)$ alkylcarbonyl group;
(e15) a halo $(C_1-C_6)$ alkylcarbonyl group;
(e16) a $(C_3-C_6)$ cycloalkylcarbonyl group;
(e17) a carboxyl group;
(e18) a $(C_1-C_6)$ alkoxycarbonyl group; or
(e24) a $(C_2-C_6)$ alkenyl group, R⁶ represents
  (f3) a (C₁-C₆) alkyl group or
  (f4) a halo (C₁-C₆) alkyl group,
R⁷ represents
  (g1) a hydrogen atom;
  (g2) a halogen atom;
  (g3) a (C₁-C₆) alkyl group;
  (g4) a halo (C₁-C₆) alkyl group;
  (g5) a (C₁-C₆) alkoxy group;
  (g6) a halo (C₁-C₆) alkoxy group;
  (g7) a (C₁-C₆) alkylthio group;
  (g8) a halo (C₁-C₆) alkylthio group;
  (g10) a (C₃-C₆) cycloalkyl group;
  (g14) a (C₁-C₆) alkylcarbonyl group;
  (g15) a halo (C₁-C₆) alkylcarbonyl group;
  (g16) a (C₃-C₆) cycloalkylcarbonyl group; or
  (g17) a (C₁-C₆) alkoxycarbonyl group, and
R⁸ represents
  (h1) a hydrogen atom;
  (h2) a halogen atom;
  (h3) a (C₁-C₆) alkyl group;
  (h4) a halo (C₁-C₆) alkyl group;
  (h5) a (C₁-C₆) alkoxy group;
  (h6) a halo (C₁-C₆) alkoxy group;
  (h7) a (C₁-C₆) alkylthio group;
  (h8) a halo (C₁-C₆) alkylthio group;
  (h10) a (C₃-C₆) cycloalkyl group;
  (h14) a (C₁-C₆) alkylcarbonyl group;
  (h15) a halo (C₁-C₆) alkylcarbonyl group;
  (h16) a (C₃-C₆) cycloalkylcarbonyl group; or
  (h17) a (C₁-C₆) alkoxycarbonyl group.

5. The amide compound or the salt thereof according to claim 1, wherein
R⁵ represents
  (e2) a halogen atom;
  (e3) a (C₁-C₆) alkyl group;
  (e4) a halo (C₁-C₆) alkyl group;
  (e10) a (C₃-C₆) cycloalkyl group;
  (e17) a carboxyl group;
  (e18) a (C₁-C₃) alkoxycarbonyl group; or
  (e24) a (C₂-C₆) alkenyl group,
R⁶ represents
  (f3) a (C₁-C₃) alkyl group or
  (f4) a halo (C₁-C₃) alkyl group,
R⁷ represents
  (g1) a hydrogen atom;
  (g3) a (C₁-C₆) alkyl group; or
  (g4) a halo (C₁-C₆) alkyl group, and
R⁸ represents (h1) a hydrogen atom.

6. The amide compound or the salt thereof according to claim 1, wherein
R⁵ represents
  (e3) a (C₁-C₆) alkyl group or
  (e4) a halo (C₁-C₆) alkyl group,
R⁶ represents
  (f3) a (C₁-C₃) alkyl group or
  (f4) a halo (C₁-C₃) alkyl group, R⁷ represents
  (g1) a hydrogen atom;
  (g2) a halogen atom;
  (g3) a (C₁-C₆) alkyl group; or
  (g4) a halo (C₁-C₆) alkyl group, and
R⁸ represents
  (h2) a halogen atom;
  (h3) a (C₁-C₆) alkyl group;
  (h4) a halo (C₁-C₆) alkyl group;
  (h5) a (C₁-C₆) alkoxy group;
  (h6) a halo (C₁-C₆) alkoxy group;
  (h7) a (C₁-C₆) alkylthio group;
  (h8) a halo (C₁-C₆) alkylthio group; or
  (h17) a (C₁-C₆) alkoxycarbonyl group.

7. The amide compound or the salt thereof according to claim 1, wherein the halogen atom of the haloalkyl group is fluorine.

8. An agricultural or horticultural microbicide comprising the amide compound or the salt thereof according to claim 1 as an active ingredient.

9. The amide compound or the salt thereof according to claim 1, wherein the heterocyclic ring moiety represented by

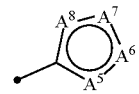

is

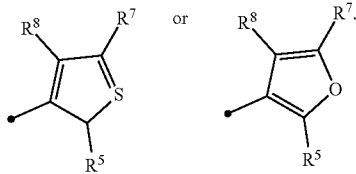

10. The amide compound or the salt thereof according to claim 1, wherein the heterocyclic ring moiety represented by

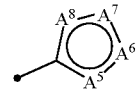

is

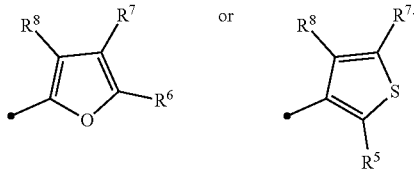

* * * * *

UNITED STATES PATENT AND TRADEMARK OFFICE
CERTIFICATE OF CORRECTION

PATENT NO. : 11,324,219 B2
APPLICATION NO. : 16/976436
DATED : May 10, 2022
INVENTOR(S) : Keiichi Yamada et al.

It is certified that error appears in the above-identified patent and that said Letters Patent is hereby corrected as shown below:

On the Title Page

Column 2, Line 5, Item (56) under Other Publications, delete "Thiophenecarboxylicacid," and insert --Thiophenecarboxylic acid,--.

In the Specification

In Column 19, Line 41, delete "$A^1$," and insert --$A^8$,--.

In Column 21, Line 53, delete "Hemilelia," and insert --Hemimelia,--.

In Column 21, Lines 57-58, delete "Unsinula;" and insert --Uncinula;--.

In Column 21, Line 64, delete "(Cochiobolus" and insert --(Cochliobolus--.

In Column 22, Line 4, delete "cichoracoarum)," and insert --cichoracearum),--.

In Column 22, Line 8, delete "Typhla" and insert --Typhula--.

In Column 22, Line 8, delete "Typhla" and insert --Typhula--.

In Column 22, Line 24, delete "fawcetti)," and insert --fawcettii),--.

In Column 22, Line 53, delete "cichoracoarum)" and insert --cichoracearum)--.

In Column 23, Line 14, delete "ringoneella," and insert --ringoniella,--.

In Column 23, Line 42, delete "Eupoecillia" and insert --Eupoecilia--.

In Column 23, Line 47, delete "Acanthoplusia agnate," and insert --Acantholysis agnatha,--.

Signed and Sealed this
Eighteenth Day of October, 2022

Katherine Kelly Vidal
*Director of the United States Patent and Trademark Office*

In Column 23, Line 64, delete "Aeschynteles" and insert --Aeschynanthus--.

In Column 24, Line 6, delete "Rhopalosophum" and insert --Rhopalosiphum--.

In Column 24, Line 17, delete "longispinis," and insert --longispinus,--.

In Column 24, Line 26, delete "Uroeucon" and insert --Uroleucon--.

In Column 24, Line 31, delete "spinolai," and insert --spinolae,--.

In Column 24, Line 38, delete "Rhopalosophum" and insert --Rhopalosiphum--.

In Column 24, Line 40, delete "Speusotettix" and insert --Speudotettix--.

In Column 24, Line 61, delete "farinose" and insert --farinosa--.

In Column 24, Line 65, delete "ishidai," and insert --ishidae,--.

In Column 26, Line 6, delete "Franklinella" and insert --Frankliniella--.

In Column 26, Line 15, delete "Rhyzoglyphus robini" and insert --Rhizoglyphus rohini--.

In Column 26, Line 33, delete "Tylenchus" and insert --Tylenchulus--.

In Column 28, Line 24, delete "6-" and insert --δ- --.

In Column 33, Line 24, delete "(D-D)," and insert --(DD),--.

In Column 33, Line 35, delete "ethofenprox," and insert --etofenprox,--.

In Column 33, Line 44, delete "chlorphenapyr," and insert --chlorfenapyr,--.

In Column 34, Line 14 (Approx.), delete "flurimfen," and insert --flurofen,--.

In Column 36, Line 8, delete "imazamethapyr," and insert --imazethapyr,--.

In Column 36, Line 15, delete "endothal," and insert --endothall,--.

In Column 37, Line 18, delete "flumezin," and insert --fluomizin,--.

In Column 37, Line 57, delete "radiobactor," and insert --radiobacter,--.

In Column 48, Lines 21-27 (Approx.), delete "  " and insert

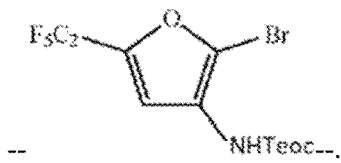

In Column 50, Line 53, delete "(J)" and insert --(J1)--.

In Column 50, Line 54, delete "44)" and insert --44%)--.

In Column 50, Line 65, delete "280)" and insert --28%)--.

In Column 53, Table 2-1, ($A^6$), Line 7, delete "0" and insert --O--.

In Column 53, Table 2-2, ($A^6$), Line 1, delete "0" and insert --O--.

In Column 53, Table 2-2, ($A^6$), Line 2, delete "0" and insert --O--.

In Column 53, Table 2-2, ($A^6$), Line 3, delete "0" and insert --O--.

In Column 53, Table 2-2, ($A^6$), Line 4, delete "0" and insert --O--.

In Column 53, Table 2-2, ($A^6$), Line 5, delete "0" and insert --O--.

In Column 53, Table 2-2, ($A^6$), Line 6, delete "0" and insert --O--.

In Column 53, Table 2-2, ($A^6$), Line 7, delete "0" and insert --O--.

In Column 53, Table 2-2, ($A^6$), Line 8, delete "0" and insert --O--.

In Column 53, Table 2-2, ($A^6$), Line 9, delete "0" and insert --O--.

In Column 53, Table 2-2, ($A^6$), Line 10, delete "0" and insert --O--.

In Column 53, Table 2-2, ($A^6$), Line 11, delete "0" and insert --O--.

In Column 53, Table 2-2, ($A^6$), Line 12, delete "0" and insert --O--.

In Column 53, Table 2-2, ($A^6$), Line 13, delete "0" and insert --O--.

In Column 53, Table 2-2, ($A^6$), Line 14, delete "0" and insert --O--.

In Column 53, Table 2-2, ($A^6$), Line 15, delete "0" and insert --O--.

In Column 53, Table 2-2, ($A^6$), Line 16, delete "0" and insert --O--.

In Column 53, Table 2-2, (A⁶), Line 17, delete "0" and insert --O--.

In Column 53, Table 2-2, (A⁶), Line 18, delete "0" and insert --O--.

In Column 53, Table 2-2, (A⁶), Line 19, delete "0" and insert --O--.

In Column 53, Table 2-2, (A⁶), Line 20, delete "0" and insert --O--.

In Column 53, Table 2-2, (A⁶), Line 21, delete "0" and insert --O--.

In Column 53, Table 2-2, (A⁶), Line 22, delete "0" and insert --O--.

In Column 53, Table 2-2, (A⁶), Line 23, delete "0" and insert --O--.

In Column 56, Table 4-5, (Physical property value), Line 4 (Approx.), delete "199" and insert --199°--.

In Column 58, Table 5-3, (Physical property value), Line 9 (Approx.), delete "39" and insert --39°--.

In the Claims

In Column 70, Lines 31-38 (Approx.), delete " 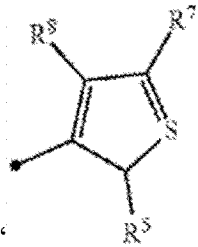 " and insert -- 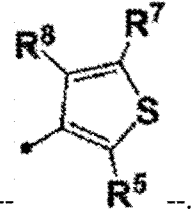 --.

In Column 70, Lines 51-57 (Approx.), delete " 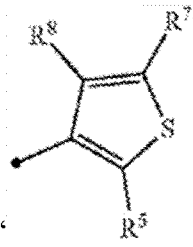 " and insert -- 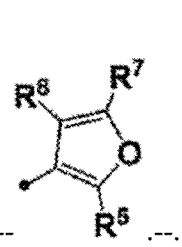 .--.